United States Patent
Hill et al.

(10) Patent No.: US 7,192,717 B2
(45) Date of Patent: Mar. 20, 2007

(54) GASP1: A FOLLISTATIN DOMAIN CONTAINING PROTEIN

(75) Inventors: Jennifer J. Hill, Somerville, MA (US); Neil M. Wolfman, Dover, MA (US)

(73) Assignee: Wyeth, Madison, NJ (US)

(*) Notice: Subject to any disclaimer, the term of this patent is extended or adjusted under 35 U.S.C. 154(b) by 0 days.

(21) Appl. No.: 10/369,736

(22) Filed: Feb. 21, 2003

(65) Prior Publication Data

US 2003/0162714 A1    Aug. 28, 2003

Related U.S. Application Data

(60) Provisional application No. 60/434,644, filed on Dec. 20, 2002, provisional application No. 60/357,845, filed on Feb. 21, 2002.

(51) Int. Cl.
*G01N 33/53*    (2006.01)
*C12Q 1/68*     (2006.01)
*C07K 1/00*     (2006.01)
*A01N 37/18*    (2006.01)

(52) U.S. Cl. .................. 435/7.1; 435/6; 530/350; 514/2

(58) Field of Classification Search ............... 530/350
See application file for complete search history.

(56) References Cited

U.S. PATENT DOCUMENTS

| | | |
|---|---|---|
| 4,179,337 A | 12/1979 | Davis et al. |
| 5,639,638 A | 6/1997 | Wozney et al. |
| 5,700,911 A | 12/1997 | Wozney et al. |
| 5,723,125 A | 3/1998 | Chang et al. |
| 5,756,457 A | 5/1998 | Wang et al. |
| 5,827,733 A | 10/1998 | Lee et al. |
| 5,914,234 A | 6/1999 | Lee et al. |
| 5,942,420 A | 8/1999 | Holtzman |
| 5,994,618 A | 11/1999 | Lee et al. |
| 6,004,937 A | 12/1999 | Wood et al. |
| 6,096,506 A | 8/2000 | Lee et al. |
| 6,340,668 B1 | 1/2002 | Celeste et al. |
| 6,368,597 B1 | 4/2002 | Strassmann et al. |
| 6,369,201 B1 | 4/2002 | Barker et al. |
| 6,372,454 B2 | 4/2002 | Duan et al. |
| 6,437,111 B1 | 8/2002 | Wozney et al. |
| 6,537,966 B1* | 3/2003 | Duan et al. ............ 514/2 |
| 6,656,475 B1 | 12/2003 | Lee et al. |
| 6,696,260 B1 | 2/2004 | Lee et al. |
| 6,835,544 B2 | 12/2004 | Mathews et al. |
| 2002/0150577 A1 | 10/2002 | Lee et al. |
| 2003/0104406 A1 | 6/2003 | Wolfman et al. |
| 2003/0138422 A1 | 7/2003 | Aghajanian et al. |
| 2003/0180306 A1 | 9/2003 | Hill et al. |
| 2004/0077053 A1 | 4/2004 | Lee et al. |
| 2004/0138118 A1 | 7/2004 | Wolfman et al. |
| 2004/0142382 A1 | 7/2004 | Veldman et al. |
| 2004/0181033 A1 | 9/2004 | Han et al. |
| 2004/0223966 A1 | 11/2004 | Wolfman et al. |
| 2005/0043232 A1 | 2/2005 | Lee et al. |

FOREIGN PATENT DOCUMENTS

| | | |
|---|---|---|
| EP | 1 061 940 B1 | 12/2003 |
| EP | 1 444 985 A1 | 8/2004 |
| WO | WO 94/21681 | 9/1994 |
| WO | WO 94-26892 | 11/1994 |
| WO | WO 96-01845 | 1/1996 |
| WO | WO 99/24058 | 5/1999 |
| WO | WO 99/45949 | 9/1999 |
| WO | WO 99/56768 | 11/1999 |
| WO | WO 00/11163 | 3/2000 |
| WO | WO 00/43781 | 7/2000 |
| WO | WO 01/64888 A2 * | 7/2001 |
| WO | WO 02/09641 A2 | 2/2002 |
| WO | WO 02/068650 A2 | 9/2002 |
| WO | WO 03/027248 A2 | 4/2003 |
| WO | WO 04-058988 A2 | 7/2004 |

OTHER PUBLICATIONS

Riley, H. R. et al., Pharmacogenomics, vol. 1(1), p. 39, lines 2-4.*
Sequence Alignments, pp. 1-10.*
Wells 1990. Biochemistry 29:8509-8517.*
Ngo et al. 1994. The Protein Folding Problem and Tertiary Structure Prediction, pp. 492-495.*
Hamrick et al. "Bone Mineral Content and Density in the Humerus of Adult Myostatin-Deficient Mice" *Calcified Tissue International*, 71(1):63-68 (2002).
Hayette et al. "FLRG (Follistatin-Related Ggene), A New Target of Chromosomal Rearrangement in Malignant Blood Disorders" *Onconogene*, 16:2949-2954 (1998).
Lee et al. "Regulation of Myostatin Activity and Muscle Growth" *PNAS*, 98(16):9306-9311 (2001).
Maguer-Satta et al. "During Hematopoiesis, Expression of FLRG, a Novel Activin A Ligand, is regulated by TGF-β" *Exp. Hematol.*, 29:301-308 (2001).
McPherron et al. "Double Muscling in Cattle Due to Mutations in the Myostatin Gene" *PNAS*, 94:12457-12461 (1997).
Schneyer et al. "Follistatin-Related Protein (FSRP): A New Member of the Follistatin Gene Family" *Mol. Cell. Endocrinol.*, 180:33-38 (2001).
Thies et al. "GDF-8 Propeptide Binds to GDF-8 and Antagonizes Biological Activity by Inhibiting GDF-8 Receptor Binding" *Growth Factors*, 18:251-259 (2000).

(Continued)

*Primary Examiner*—Lorraine Spector
*Assistant Examiner*—Shulamith H Shafer
(74) *Attorney, Agent, or Firm*—Finnegan, Henderson, Farabow, Garrett, & Dunner, L.L.P.

(57) ABSTRACT

The present invention relates to the use of a protein, GASP1, comprising at least one follistatin domain to modulate the level or activity of growth and differentiation factor-8 (GDF-8). More particularly, the invention relates to the use of GASP1 for treating disorders that are related to modulation of the level or activity of GDF-8. The invention is useful for treating muscular diseases and disorders, particularly those in which an increase in muscle tissue would be therapeutically beneficial. The invention is also useful for treating diseases and disorders related to metabolism, adipose tissue, and bone degeneration.

25 Claims, 27 Drawing Sheets

OTHER PUBLICATIONS

Tsuchida et al. "Identification and Characterization of a Novel Follistatin-like Protein as a Binding Protein for the TGF-β Family" *J. Biol. Chem.*, 275:40788-40796 (2000).

Tsuchida et al. "Intracellular and Extracellular Control of Activin Function by Novel Regulatory Molecules" *Mol. Cell. Endocrin.*, 180:25-31 (2001).

Zhu et al. "Dominant Negative Myostatin Produces Hypertrophy without Hyperplasia in Muscle" *FEBS Letters*, 474(1):71-75 (2000).

Zwusen et al. "Characterization of a Rat $C_6$ Glioma-Secreted Follistain-Related Protein (FRP)" *Eur. J. Biochem.*, 225:937-946 (1994).

Alliel et al., "Testican, a Multidomain Testicular Proteoglycan Resembling Modulators of Cell Social Behaviour," *Eur. J. Biochem.* 214:347-350 (1993).

Amthor et al., "The Expression and Regulation of Follistatin and a Follistatin-like Gene During Avian Somite Compartmentalization and Myogenesis," *Dev. Biol.* 178:343-362 (1996).

Ashmore et al., "Comparative Aspects of Muscle Fiber Types in Fetuses of the Normal and 'Double-Muscled' Cattle," *Growth* 38:501-506 (1974).

Bakker et al., Duchenne and Becker Muscular Dystrophies. In *Diagnostic Criteria for Neuromuscular Disorders*, 2nd ed., Emery, ed., Royal Society of Medicine Press, 1998; pp. 1-4.

Bartholin et al., "FLRG, an Activin-Binding Protein, is a New Target of TGFβ Transcription Activation Through Smad Proteins," *Oncogene* 20:5409-5419 (2001).

Bogdanovich et al., "Functional Improvement of Dystrophic Muscle by Myostatin Blockade," *Nature* 420:418-421 (2002).

Brown et al., "Physicochemical Activation of Recombinant Latent Transforming Growth Factor-Beta's 1, 2, and 3," *Growth Factors* 3:35-43 (1990).

Bulfield et al., "X Chromosome-Linked Muscular Dystrophy (*mdx*) in the Mouse," *Proc. Natl. Acad. Sci. U.S.A.* 81:1189-1192 (1984).

Derynck et al., "Human Transforming Growth Factor-β Complementary DNA Sequence and Expression in Normal and Transformed Cells," *Nature* 316:701-705 (1985).

Emery, "The Muscular Dystrophies," *Lancet* 359:687-695 (2002).

Escolar et al., "Pharmacologic and Genetic Therapy for Childhood Muscular Dystrophies," *Current Neurology and Neuroscience Reports* 1:168-174 (2001).

Gamer et al., "A Novel BMP Expressed in Developing Mouse Limb, Spinal Cord, and Tail Bud Is a Potent Mesoderm Inducer in *Xenopus* Embryos," *Dev. Biol.* 208:222-232 (1999).

Gentry et al., "The Pro Domain of Pre-Pro-Transforming Growth Factor β1 When Independently Expressed Is a Functional Binding Protein for the Mature Growth Factor," *Biochemistry* 29:6851-6857 (1990).

Gillis, "Multivariate Evaluation of the Functional Recovery Obtained by the Overexpression of Utrophin in Skeletal Muscles of the *mdx* Mouse," *Neuromuscular Disorders* 12:S90-S94 (2002).

Girard et al., "Modulation of Endothelial Cell Adhesion by Hevin, an Acidic Protein Associated with High Endothelial Venules," *J. Biol. Chem.* 271:4511-4517 (1996).

Gonzalez-Cadavid et al., "Organization of the Human Myostatin Gene and Expression in Healthy Men and HIV-Infected Men With Muscle Wasting," *Proc. Natl. Acad. Sci. U.S.A.*, 95:14938-14943 (1998).

Grady et al., "Skeletal and Cardiac Myopathies in Mice Lacking Utrophin and Dystrophin: A Model for Duchenne Muscular Dystrophy," *Cell* 90:729-738 (1997).

Hamrick et al., "Femoral Morphology and Cross-Sectional Geometry of Adult Myostatin-Deficient Mice," *Bone* 27:343-349 (2000).

Hill et al., "Regulation of Myostatin *in Vivo* by Growth and Differentiation Factor-Associated Serum Protein-1: A Novel Protein with Protease Inhibitor and Follistatin Domains," *Mol. Endocrinol.* 17:1144-1154 (2003).

Hill et al., "The Myostatin Propeptide and the Follistatin-Related Gene are Inhibitory Binding Proteins of Myostatin in Normal Serum," *J. Biol. Chem.* 277:40735-40741 (2002).

Hoffman et al., "Conservation of the Duchenne Muscular Dystrophy Gene in Mice and Humans," *Science* 238:347-350 (1987).

Kambadur et al., "Mutations in *myostatin* (GDF8) In Double-Muscled Belgian Blue and Piedmontese Cattle," *Genome Res.* 7:910-915 (1997).

Kato, "A Secreted Tumor-Suppressor, mac25, with Activin-Binding Activity," *Mol. Med.* 6:126-135 (2000).

Khurana et al., "Pharmacological Strategies for Muscular Dystrophy," *Nat. Rev. Drug Disc.* 2:379-386 (2003).

Kim et al., "Inhibition of Preadipocyte Differentiation by Myostatin Treatment in 3T3-L1 Cultures," *Biochem. Biophys. Res. Commun.* 281:902-906 (2001).

Massagué, "The Transforming Growth Factor-β Family," *Annu. Rev. Cell Biol.* 6:597-641 (1990).

Matsuda et al., "Visualization of Dystrophic Muscle Fibers in Mdx Mouse by Vital Staining with Evans Blue: Evidence of Apoptosis in Dystrophin-Deficient Muscle," *J. Biochem.* 118:959-964 (1995).

McPherron et al., "Regulation of Skeletal Muscle Mass in Mice by a New TGF-β Superfamily Member," *Nature* 387:83-90 (1997).

McPherron et al., "Suppression of Body Fat Accumulation in Myostatin-Deficient Mice," *J. Clin. Invest.* 109:595-601 (2002).

Miyazono et al., "Latent High Molecular Weight Complex of Transforming Growth Factor β1," *J. Biol. Chem.* 263:6407-6415 (1988).

Morrison et al., "T-Cell-Dependent Fibrosis in the mdx Dystrophic Mouse," *Lab. Invest.* 80:881-891 (2000).

Motamed, "Moleclues in Focus, SPARC (Osteonectin/BM-40)," *Int. J. Biochem. Cell. Biol.* 31:1363-1366 (1999).

Patel et al., "Cloning and Early Dorsal Axial Expression of Flik, a Chick Follistatin-Related Gene: Evidence for Involvement in Dorsalization/Neural Induction," *Dev. Biol.* 178: 327-342 (1996).

Patthy et al., "Functions of Agrin and Agrin-Related Proteins," *Trends Neurosci.* 16:76-81 (1993).

Phillips et al., "Follistatin: A Multifunctional Regulatory Protein," *Front. Neuroendocrin.* 19:287-322 (1998).

Schäcke et al., "Mechanisms Involved in the Side Effects of Glucocorticoids," *Pharmacol. Ther.* 96:23-43 (2002).

Shibanuma et al., "Cloning From a Mouse Osteoblastic Cell Line of a Set of Transforming-Growth-Factor-β1-Regulated Genes, One of Which Seems to Encode a Follistatin-Related Polypeptide," *Eur. J. Biochem.* 217:13-19 (1993).

Swatland et al., "Fetal Development of the Double Muscled Condition in Cattle," *J. Anim. Sci.* 38:752-757 (1974).

Torres et al., "The Mutant mdx: Inherited Myopathy in the Mouse," *Brain* 110:269-299 (1987).

Trexler et al. "Distinct Expression Pattern of Two Related Human Proteins Containing Multiple Types of Protease-Inhibitory Modules," *Biol. Chem.* 383:223-228 (2002).

Trexler et al., "A Human Protein Containing Multiple Types of Protease-Inhibitory Modules," *Proc. Natl. Acad. Sci. U.S.A.* 98:3705-3709 (2001).

Umland et al., "Review of the Molecular and Cellular Mechanisms of Action of Glucocorticoids for Use in Asthma," *Pulmonary Pharmacology & Therapeutics* 15:35-50 (2002).

Wagner et al., "Loss of Mysostatin Attenuates Severity of Muscular Dystrophy in *mdx* Mice," *Ann. Neurol.* 52:832-836 (2002).

Wakefield et al., "Latent Transforming Growth Factor-β From Human Platelets," *J. Biol. Chem.* 263:7646-7654(1988).

Whittemore et al., "Inhibition of Myostatin in Adult Mice Increases Skeletal Muscle Mass and Strength," *Biochem. Biophys. Res. Commun.* 300:965-971 (2003).

Zimmers et al., "Induction of Cachexia in Mice by Systemically Adminstered Myostatin," *Science* 296:1486-1488 (2002).

Access. No. XP_137872 [gi:20914039].

Access. No. AAL77058 [gi: 18652308].

Alexander et al., "Human Parathyroid Hormone 1-34 Reverses Bone Loss In Ovariectomized Mice," *J. Bone Miner. Res.* 16:1665-1673 (2001).

Andersson et al., "Repeated *In Vivo* Determinations of Bone Mineral Density During Parathyroid Hormone Treatment in Ovariectomized Mice," *J. Endocrinol.* 170:529-537 (2001).

Attisano et al., "Activation of Signalling by the Activin Receptor Complex," *Mol. Cell. Biol.* 16:1066-1073 (1996).

D'Angelo et al., "Authentic Matrix Vesicles Contain Active Metalloproteases (MMP)," *J. Biol. Chem.* 276:11347-11353 (2001).

Donoghue et al., "Rostrocaudal Gradient of Transgene Expression in Adult Skeletal Muscle," *Proc. Natl. Acad. Sci. U.S.A.* 88:5847-5851 (1991).

Gamer et al., "Gdf11 is a Negative Regulator of Chondrogenesis and Myogenesis in the Developing Chick Limb," *Dev. Biol.* 229:407-420 (2001).

Granchelli et al., "Pre-Clinical Screening of Drugs Using the *mdx* Mouse," *Neuromuscular Disorders* 10:235-239 (2000).

Hoodless et al., "Mechanisms and Function of Signaling by the TGFβ Superfamily," *Curr. Top. Microbiol. Immunol.* 228:236-272 (1998).

Huet et al., "Skeletal Muscle Cell Hypertrophy Induced by Inhibitors of Metalloproteases; Myostatin as a Potential Mediator," *Am. J. Physiol. Cell. Physiol.* 281:C1624-C1634 (2001).

Jiang et al., "Characterization and Identification of the Inhibitory Domain of GDF-8 Propeptide," *Biochem. Biophys. Res. Commun.* 315:525-531 (2004).

Kessler et al., "Bone Morphogenetic Protein-1: The Type I Procollagen C-Proteinase," *Science* 271:360-362 (1996).

Kingsley, D.M., "The TGF-β Superfamily: New Members, New Receptors, and New Genetic Tests of Function in Different Organisms," *Genes Dev.* 8:133-146 (1994).

Lang et al., "Regulation of Myostatin by Glucocorticoids After Thermal Injury," *FASEB J.* 15:1807-1809 (2001).

Lee et al., "Analysis of Site-Directed Mutations in Human Pro-a2(I) Collagen Which Block Cleavage by the C-Proteinase," *J. Biol. Chem.* 265:21992-21996 (1990).

Li et al., "The C-Proteinase that Processes Procollagens to Fibrillar Collagens is Identical to the Protein Previously Identified as Bone Morphogenic Protein-1," *Proc. Natl. Acad. Sci. U.S.A.* 93:5127-5130 (1996).

Lin et al., "Expression Cloning of the TGF-β Type II Receptor, a Functional Transmembrane Serine/Threonine Kinase," *Cell* 68:775-785 (1992).

Liu et al., "Assigning the Positional Identity of Spinal Motor Neurons: Rostrocaudal Patterning of Hox-c Expression by FGFs, Gdf11, and Retinoids," *Neuron* 32:997-1012 (2001).

Lyons et al., "Proteolytic Activation of Latent Transforming Growth Factor-β from Fibroblast-Conditioned Medium," *J. Cell Biol.* 106:1659-1665 (1988).

Maeda et al., "Activation of Latent Transforming Growth Factor β1 by Stromelysin 1 in Extracts of Growth Plate Chondrocyte-Derived Matrix Vesicles," *J. Bone Miner. Res.* 16:1281-1290 (2001).

Marques et al., "Production of a DPP Activity Gradient in the Early Drosophilia Embryo through the Opposing Actions of the SOG and TLD Proteins," *Cell* 91:417-426 (1997).

Massagué et al., "Receptors for the TGF-β Family," *Cell* 69:1067-1070 (1992).

Massagué et al., "The TGF-β Family and its Composite Receptors," *Trends Cell Biol.* 4:172-178 (1994).

Massagué, "How Cells Read TGF-β Signals," *Nature Rev. Mol. Cell. Biol.* 1:169-178 (2000).

McPherron et al., "Regulation of Anterior/Posterior Patterning of the Axial Skeleton by Growth/Differentiation Factor 11," *Nature Genet.* 22:260-264 (1999).

Moustakas et al., "Smad Regulation in TGF-β Signal Transduction," *J. Cell Sci.* 114:4359-4369 (2001).

Nakamura et al., "Follistatin, an Activin-Binding Protein, Associates with Heparan Sulfate Chains of Proteoglycans on Follicular Granulosa Cells," *J. Biol. Chem.* 266:19432-19437 (1991).

Nakamura et al., "Isolation and Characterization of Activin Receptor from Mouse Embryonal Carcinoma Cells," *J. Biol. Chem.* 267:18924-18928 (1992).

Nakashima et al., "Expression of Growth/Differentiation Factor 11, A New Member of the BMP/TGF β Superfamily During Mouse Embryogenesis," *Mech. Dev.* 80:185-189 (1999).

Ngo et al., In *The Protein Folding Problems and Tertiary Structure Prediction*, Merz et al., eds., *Brickhauser*, Springer Verlag, Boston, pp. 433-434 & 492-495 (1994).

Pappano et al., "Use of BMP1-TlI1 Doubly Homozygous Null Mice and Proteomics to Identify and Validate In Vivo Substrates of Bone Morphogenetic Protein 1/Tolloid-Like Metalloproteinases," *Mol. Cell. Biol.* 23:4428-4438 (2003).

Piccolo et al., "Cleavage of Chordin by Xolloid Metalloprotease Suggests a Role for Proteolytic Processing in the Regulation of Spemann Organizer Activity," *Cell* 91:407-416 (1997).

R&D Systems, Inc., "Recombinant Human Activin Receptor IIB-Fc Chimera: Specifications and Use," Cat. No. 339-RB (2002).

Sato et al., "Inhibition of Endothelial Cell Movement by Pericytes and Smooth Muscle Cells: Activation of a Latent Transforming Growth Factor-β1-Like Molecule by Plasmin During Co-Culture," *J. Cell Biol.* 109:309-315 (1989).

Scott et al., "Bone Morphogenetic Protein-1 Processes Probiglycan," *J. Biol. Chem.* 275:30504-30511 (2000).

Scott et al., "Mammalian BMP-1-Tolloid-Related Metalloproteinases, Including Novel Family Member Mammalian Tolloid-Like 2, Have Differential Enzymatic Activities and Distributions of Expression Relevant to Patterning and Skeletogenesis," *Dev. Biol.* 213:283-300 (1999).

Sternberg et al., "Identification of Upstream and Intragenic Regulatory Elements that Confer Cell-Type-Restricted and Differentiation-Specific Expression on the Muscle Creatine Kinase Gene," *Mol. Cell. Biol.* 8:2896-2909 (1988).

Takahara et al., "Bone Morphogenetic Protein-1 and a Mammalian Tolloid Homologue (mTld) Are Encoded by Alternatively Spliced Transcripts Which Are Differentially Expressed in Some Tissues," *J. Biol. Chem.* 269:32572-32578 (1994).

Takahara et al., "Characterization of a Novel Gene Product (Mammalian Tolloid-like) with High Sequence Similarity to Mammalian Tolloid/Bone Morphogenetic Protein-1," *Genomics* 34:157-165 (1996).

Uzel et al., "Multiple Bone Morphogenetic Protein 1-Related Mammalian Metalloproteinases Process Pro-Lysyl Oxidase at the Correct Physiological Site and Control Lysyl Oxidase Activation in Mouse Embryo Fibroblast Cultures," *J. Biol. Chem.* 276:22537-22543 (2001).

Wolfman et al., "Activation of Latent Myostatin by the BMP-1/Tolloid Family of Metalloproteinases," *Proc. Natl. Acad. Sci. U.S.A.* 100:15842-15846 (2003).

Wu et al., "Autoregulation of Neurogenesis by GDF-11," *Neuron* 37:197-207 (2003).

Wuytens et al., "Identification of Two Amino Acids in Activin A That Are Important for Biological Activity and Binding to the Activin Type II Receptors," *J. Biol. Chem.* 274:9821-9827 (1999).

Yu et al., "Cell Surface-Localized Matrix Metalloproteinase-9 Proteolytically Activates TGF-β and Promotes Tumor Invasion and Angiogenesis," *Genes Dev.* 14:163-176 (2000).

International Search Report in PCY/US03/05150 dated Oct. 20, 2006.

Syed et al. "Potent Antithrombin Activity and Delayed Clearance From the Circulation Characterized Recombinant Hirudin Genetically Fused to Albumin" *Blood* 89(9):3243-3252.

\* cited by examiner

PREDICTED MOUSE GASP1 NUCLEOTIDE SEQUENCE
SEQ ID NO:1

```
   1 atgtgtgccc cagggtatca tcggttctgg tttcactggg ggctgctgtt gctgctgctc
  61 ctcgaggctc cccttcgagg cctagcactg ccacccatcc gatactccca tgcgggcatc
 121 tgccccaacg acatgaaccc caacctctgg gtggatgccc agagcacctg caagcgagag
 181 tgtgaaacag accaggaatg tgagacctat gagaaatgct gccccaatgt gtgtgggacc
 241 aagagctgtg tggcagcccg ctacatggat gtgaaaggga agaagggccc tgtgggcatg
 301 cccaaggagg ccacatgtga ccatttcatg tgcctgcagc agggctctga gtgtgacatc
 361 tgggacggcc agcccgtgtg taagtgcaaa gatcgctgtg agaaggagcc cagcttcacc
 421 tgtgcctctg atggccttac ctactacaac cgttgcttca tggacgccga agcctgctcc
 481 aagggcatca cactgtctgt ggtcacctgt cgttatcact tcacctggcc taacaccagc
 541 cctccaccgc ctgagaccac ggtgcatccc accaccgcct ctccggagac tctcgggctg
 601 gacatggcag ccccggccct gctcaaccac cctgtccatc agtcagtcac cgtgggtgag
 661 actgtgagtt tcctctgtga cgtggtaggc cggcctcggc cagagctcac ttgggagaaa
 721 cagctggagg accgagaaaa tgttgtcatg aggcccaacc acgtgcgcgg taatgtggtg
 781 gtcactaaca ttgcccagct ggtcatctac aacgtccagc cccaggatgc tggcatatac
 841 acctgtacag ctcgaaatgt cgctggtgtc ctgagggctg acttcccgtt gtcggtggtc
 901 aggggtggtc aggccagggc cacttcagag agcagtctca atggcacagc ttttccagca
 961 acagagtgcc tgaagccccc agacagtgag gactgtggag aggagcagac acgctggcac
1021 ttcgacgccc aggctaacaa ctgcctcact ttcacctttg ccactgccca ccacaatctc
1081 aaccactttg agacctacga ggcctgtatg ctggcttgta tgagtgggcc attggccacc
1141 tgcagcctgc ctgccctgca agggccttgc aaagcttatg tcccacgctg ggcctacaac
1201 agccagacag cctatgccag tccttcgtc tatggcggct gtgagggcaa cggtaacaac
1261 tttgaaagcc gtgaggcttg tgaggagtcg tgtcccttcc gaggggtaa ccagcactgc
1321 cgggcctgca gccccggca aaacttgtt accagcttct gtcggagtga ctttgtcatc
1381 ctgggcaggg tctctgagct gaccgaagag caagactcag gccgtgccct ggtgaccgtg
1441 gatgaggtct aaaagatga aagatgggc ctcaagtttc tgggccggga gcctctggaa
1501 gtcaccctgc ttcatgtaga ctggacctgt ccttgcccca acgtgacagt gggtgagaca
1561 ccactcatca tcatggggga ggtcgacggc ggcatggcca tgctgagacc cgatagcttt
1621 gtgggggcat cgagcacacg gcgggtcagg aagctccgtg aggtcatgta caagaaaacc
1681 tgtgacgtcc tcaaggactt cctgggcttg caatga
```

FIG. 6A

PREDICTED MOUSE GASP1 ALTERNATIVE NUCLEOTIDE SEQUENCE
SEQ ID NO:2

```
   1 atgtgtgccc cagggtatca tcggttctgg tttcactggg ggctgctgtt
  51 gctgctgctc ctcgaggctc cccttcgagg cctagcactg ccacccatcc
 101 gatactccca tgcgggcatc tgccccaacg acatgaaccc caacctctgg
 151 gtggatgccc agagcacctg caagcgagag tgtgaaacag accaggaatg
 201 tgagacctat gagaaatgct gccccaatgt gtgtgggacc aagagctgtg
 251 tggcagcccg ctacatggat gtgaaaggga agaaggggcc tgtaggcatg
 301 cccaaggagg ccacatgtga ccatttcatg tgcctgcagc agggctctga
 351 gtgtgacatc tgggacggcc agcccgtgtg taagtgcaaa gatcgctgtg
 401 agaaggagcc cagcttcacc tgtgcctctg atggccttac ctactacaac
 451 cgttgcttca tggacgccga agcctgctcc aagggcatca cactgtctgt
 501 ggtcacctgt cgttatcact tcacctggcc taacaccagc cctccaccgc
 551 ctgagaccac ggtgcatccc accaccgcct ctccggagac tctcgggctg
 601 gacatggcag ccccagccct gctcaaccac cctgtccatc agtcagtcac
 651 cgtgggtgag actgtgagtt cctctgtga cgtggtaggc cggcctcggc
 701 cagagctcac ttgggagaaa cagctggagg accgagagaa tgttgtcatg
 751 aggcccaacc acgtgcgtgg taatgtggtg gtcactaaca ttgcccagct
 801 ggtcatctac aacgtccagc ccaggatgc tggcatatac acctgtacag
 851 ctcgaaatgt cgctggtgtc ctgagggctg acttcccgtt gtcggtggtc
 901 aggggtggtc aggccagggc cacttcagag agcagtctca atggcacagc
 951 ttttccagca acagagtgcc tgaagccccc agacagtgag gactgtggag
1001 aggagcagac acgctggcac ttcgacgccc aggctaacaa ctgcctcact
1051 ttcacctttg ccactgccca ccacaatctc aaccactttg agacctacga
1101 ggcctgtatg ctggcttgta tgagtgggcc attggccacc tgcagcctgc
1151 ctgccctgca agggccttgc aaagcttatg tcccacgctg gcctacaac
1201 agccagacag gcctatgcca gtccttcgtc tatggcggct gtgagggcaa
1251 cggtaacaac tttgaaagcc gtgaggcttg tgaggagtcg tgtcccttcc
1301 cgaggggtaa ccagcactgc cgggcctgca gccccggca aaaacttgtt
1351 accagcttct gtcggagtga ctttgtcatc ctgggcaggg tctctgagct
1401 gaccgaggag caagactcgg ccgtgccct ggtgaccgtg gatgaggtct
1451 taaaagatga aagatgggc ctcaagtttc tgggccggga gcctctggaa
1501 gtcaccctgc ttcatgtaga ctggacctgt ccttgcccca acgtgacagt
1551 gggtgagaca ccactcatca tcatggggga ggtggacggc ggcatggcca
1601 tgctgagacc cgatagcttt gtgggggcat cgagcacacg gcgggtcagg
1651 aagctccgtg aggtcatgta caagaaaacc tgtgacgtcc tcaaggactt
1701 cctgggcttg caatga
```

FIG. 6B

PREDICTED MOUSE GASP1 AMINO ACID SEQUENCE
SEQ ID NO:3

```
  1 MCAPGYHRFW FHWGLLLLLL LEAPLRGLAL PPIRYSHAGI CPNDMNPNLW VDAQSTCKRE
 61 CETDQECETY EKCCPNVCGT KSCVAARYMD VKGKKGPVGM PKEATCDHFM CLQQGSECDI
121 WDGQPVCKCK DRCEKEPSFT CASDGLTYYN RCFMDAEACS KGITLSVVTC RYHFTWPNTS
181 PPPPETTVHP TTASPETLGL DMAAPALLNH PVHQSVTVGE TVSFLCDVVG RPRPELTWEK
241 QLEDRENVVM RPNHVRGNVV VTNIAQLVIY NVQPQDAGIY TCTARNVAGV LRADFPLSVV
301 RGGQARATSE SSLNGTAFPA TECLKPPDSE DCGEEQTRWH FDAQANNCLT FTFGHCHHNL
361 NHFETYEACM LACMSGPLAT CSLPALQGPC KAYVPRWAYN SQTGLCQSFV YGGCEGNGNN
421 FESREACEES CPFPRGNQHC RACKPRQKLV TSFCRSDFVI LGRVSELTEE QDSGRALVTV
481 DEVLKDEKMG LKFLGREPLE VTLLHVDWTC PCPNVTVGET PLIIMGEVDG GMAMLRPDSF
541 VGASSTRRVR KLREVMYKKT CDVLKDFLGL Q
```

FIG. 6C

PREDICTED HUMAN GASP1 NUCLEOTIDE SEQUENCE
SEQ ID NO:4

```
   1 atgaatccca acctctgggt ggacgcacag agcacctgca ggcgggagtg tgagacggac
  61 caggagtgtg agatggacca ggtgagtggg atccagaagc cacagtgtga ggcagaccag
 121 gtgaatgggg tccagaagcc gcaatgtgag atggaccaga agtgggagtg tgaggttgac
 181 caggtgagtg gggtccagaa gccggtgtgt gaggcggacc aggtgagtgg ggtccagaag
 241 ccacagtgtg agatggacca ggtgagtggg atccagaagc tggagtgtga ggcggaccag
 301 aagtgggagt atgaggtgga ccaggtgagt ggggtccaga agccacagtg tgagatggac
 361 caggtgagtg ggatccagaa gctggagtgt gaggcggacc aggagtgtga gacctatgag
 421 aagtgctgcc ccaacgtatg tgggaccaag agctgcgtgg cggcccgcta catggacgtg
 481 aaagggaaga agggcccagt gggcatgccc aaggaggcca catgtgacca cttcatgtgt
 541 ctgcagcagg gctctgagtg tgacatctgg gatggccagc ccgtgtgtaa gtgcaaagac
 601 cgctgtgaga aggagcccag ctttacctgc gcctcggacg cctcaccta ctataaccgc
 661 tgctacatgg atgccgaggc ctgctccaaa ggcatcacac tggccgttgt aacctgccgc
 721 tatcacttca cntggcccaa caccagcccc ccaccacctg agaccaccat gcaccccacc
 781 acagcctccc cagagacccc tgagctggac atggcggccc ctgcgctgct caacaaccct
 841 gtgcaccagt cggtcaccat gggtgagaca gtgagcttcc tctgtgatgt ggtgggccgg
 901 ccccggcctg agatcacctg ggagaagcag ttggaggatc gggagaatgt ggtcatgcgg
 961 cccaaccatg tgcgtggcaa cgtggtggtc accaacattg cccagctggt catctataac
1021 gcccagctgc aggatgctgg gatctacacc tgcacggccc ggaacgtggc tggggtcctg
1081 agggctgatt tcccgctgtc ggtggtcagg ggtcatcagg ctgcagccac ctcagagagc
1141 agccccaatg gcacggcttt cccggcggcc gagtgcctga gcccccaga cagtgaggac
1201 tgtggcgaag agcagacccg ctggcacttc gatgcccagg ccaacaactg cctgaccttc
1261 accttcggcc actgccaccg taacctcaac cactttgaga cctatgaggc ctgcatgctg
1321 gcctgcatga gcgggccgct ggccgcgtgc agcctgcccg ccctgcaggg gccctgcaaa
1381 gcctacgcgc tcgctgggc ttacaacagc cagacgggcc agtgccagtc ctttgtctat
1441 ggtggctgcg agggcaatgg caacaacttt gagagccgtg aggcctgtga ggagtcgtgc
1501 cccttcccca gggggaacca gcgctgtcgg gcctgcaagc ctcggcagaa gctcgttacc
1561 agcttctgtc gcagcgactt tgtcatcctg gccgagtct ctgagctgac cgaggagcct
1621 gactcgggcc gcgccctggt gactgtggat gaggtcctaa aggatgagaa aatgggcctc
1681 aagttcctgg ccaggagcc attggaggtc actctgcttc acgtggactg ggcatgcccc
1741 tgccccaacg tgaccgtgag cgagatgccg ctcatcatca tgggggaggt ggacggcggc
1801 atggccatgc tgcgccccga tagctttgtg ggcgcatcga gtgcccgccg ggtcaggaag
1861 cttcgtgagg tcatgcacaa gaagacctgt gacgtcctca aggagtttct tggcttgcac
1921 tga
```

*FIG. 7A*

PREDICTED AMINO ACID SEQUENCE OF HUMAN GASP1

SEQ ID NO:5

```
  1 MNPNLWVDAQ STCRRECETD QECEMDQVSG IQKPQCEADQ VNGVQKPQCE MDQKWECEVD
 61 QVSGVQKPVC EADQVSGVQK PQCEMDQVSG IQKLECEADQ KWEYEVDQVS GVQKPQCEMD
121 QVSGIQKLEC EADQECETYE KCCPNVCGTK SCVAARYMDV KGKKGPVGMP KEATCDHFMC
181 LQQGSECDIW DGQPVCKCKD RCEKEPSFTC ASDGLTYYNR CYMDAEACSK GITLAVVTCR
241 YHFTWPNTSP PPPETTMHPT TASPETPELD MAAPALLNNP VHQSVTMGET VSFLCDVVGR
301 PRPEITWEKQ LEDRENVVMR PNHVRGNVVV TNIAQLVIYN AQLQDAGIYT CTARNVAGVL
361 RADFPLSVVR GHQAAATSES SPNGTAFPAA ECLKPPDSED CGEEQTRWHF DAQANNCLTF
421 TFGHCHRNLN HFETYEACML ACMSGPLAAC SLPALQGPCK AYAPRWAYNS QTGQCQSFVY
481 GGCEGNGNNF ESREACEESC PFPRGNQRCR ACKPRQKLVT SFCRSDFVIL GRVSELTEEP
541 DSGRALVTVD EVLKDEKMGL KFLGQEPLEV TLLHVDWACP CPNVTVSEMP LIIMGEVDGG
601 MAMLRPDSFV GASSARRVRK LREVMHKKTC DVLKEFLGLH
```

FIG. 7B

PREDICTED NUCLEOTIDE SEQUENCE OF HUMAN GASP1 USING AN ALTERNATIVE START SITE

SEQ ID NO:6

```
   1 atgtgggccc caaggtgtcg ccggttctgg tctcgctggg agcaggtggc agcgctgctg
  61 ctgctgctgc tactgctcgg ggtgccccccg cgaagcctgg cgctgccgcc catccgctat
 121 tcccacgccg gcatctgccc caacgacatg aatcccaacc tctgggtgga cgcacagagc
 181 acctgcaggc gggagtgtga cacggaccag gagtgtgaga cctatgagaa gtgctgcccc
 241 aacgtatgtg ggaccaagag ctgcgtggcg gcccgctaca tggacgtgaa agggaagaag
 301 ggcccagtgg gcatgcccaa ggaggccaca tgtgaccact tcatgtgtct gcagcagggc
 361 tctgagtgtg acatctggga tggccagccc gtgtgtaagt gcaaagaccg ctgtgagaag
 421 gagcccagct ttacctgcgc ctcggacggc ctcacctact ataaccgctg ctacatggat
 481 gccgaggcct gctccaaagg catcacactg gccgttgtaa cctgccgcta tcacttcacc
 541 tggcccaaca ccagccccccc accacctgag accaccatgc accccaccac agcctcccca
 601 gagacccctg agctggacat ggcggcccct gcgctgctca acaaccctgt gcaccagtcg
 661 gtcaccatgg gtgagacagt gagtttcctc tgtgatgtgg tgggccggcc ccggcctgag
 721 atcacctggg agaagcagtt ggaggatcgg gagaatgtgg tcatgcggcc caaccatgtg
 781 cgtggcaacg tggtggtcac caacattgcc cagctggtca tctataacgc ccagctgcag
 841 gatgctggga tctacacctg cacggcccgg aacgtggctg gggtcctgag ggctgatttc
 901 ccgctgtcgg tggtcagggg tcatcaggct gcagccacct cagagagcag ccccaatggc
 961 acggctttcc cggcggccga gtgcctgaag cccccagaca gtgaggactg tggcgaagag
1021 cagacccgct ggcacttcga tgcccaggcc aacaactgcc tgaccttcac cttcggccac
1081 tgccaccgta acctcaacca ctttgagacc tatgaggcct gcatgctggc ctgcatgagc
1141 gggccgctgg ccgcgtgcag cctgcccgcc ctgcaggggc cctgcaaagc ctacgcgcct
1201 cgctgggctt acaacagcca gacgggccag tgccagtcct tgtctatgg tggctgcgag
1261 ggcaatggca caactttga gagccgtgag gcctgtgagg agtcgtgccc cttccccagg
1321 gggaaccagc gctgtcgggc ctgcaagcct cggcagaagc tcgttaccag cttctgtcgc
1381 agcgactttg tcatcctggg ccgagtctct gagctgaccg aggagcctga ctcgggccgc
1441 gccctggtga ctgtggatga ggtcctaaag gatgagaaaa tgggcctcaa gttcctgggc
1501 caggagccat tggaggtcac tctgcttcac gtggactggg catgccccctg ccccaacgtg
1561 accgtgagcg agatgccgct catcatcatg ggggaggtgg acggcggcat ggccatgctg
1621 cgccccgata gctttgtggg cgcatcgagt gcccgccggg tcaggaagct tcgtgaggtc
1681 atgcacaaga agacctgtga cgtcctcaag gagtttcttg cttgcactg a
```

FIG. 7C

PREDICTED AMINO ACID SEQUENCE OF HUMAN GASP1 USING AN ALTERNATIVE START SITE

SEQ ID NO:7

```
  1 MWAPRCRRFW SRWEQVAALL LLLLLLGVPP RSLALPPIRY SHAGICPNDM NPNLWVDAQS
 61 TCRRECETDQ ECETYEKCCP NVCGTKSCVA ARYMDVKGKK GPVGMPKEAT CDHFMCLQQG
121 SECDIWDGQP VCKCKDRCEK EPSFTCASDG LTYYNRCYMD AEACSKGITL AVVTCRYHFT
181 WPNTSPPPPE TTMHPTTASP ETPELDMAAP ALLNNPVHQS VTMGETVSFL CDVVGRPRPE
241 ITWEKQLEDR ENVVMRPNHV RGNVVVTNIA QLVIYNAQLQ DAGIYTCTAR NVAGVLRADF
301 PLSVVRGHQA AATSESSPNG TAFPAAECLK PPDSEDCGEE QTRWHFDAQA NNCLTFTFGH
361 CHRNLNHFET YEACMLACMS GPLAACSLPA LQGPCKAYAP RWAYNSQTGQ CQSFVYGGCE
421 GNGNNFESRE ACEESCPFPR GNQRCRACKP RQKLVTSFCR SDFVILGRVS ELTEEPDSGR
481 ALVTVDEVLK DEKMGLKFLG QEPLEVTLLH VDWACPCPNV TVSEMPLIIM GEVDGGMAML
541 RPDSFVGASS ARRVRKLREV MHKKTCDVLK EFLGLH*
```

FIG. 7D

PREDICTED MOUSE GASP2 NUCLEOTIDE SEQUENCE
SEQ ID NO:8

```
   1 atgcctgccc cacagccatt cctgcctctg ctctttgtct tcgtgctcat ccatctgacc
  61 tcggagacca acctgctgcc agatcccgga agccatcctg gcatgtgccc caacgagctc
 121 agcccccacc tgtgggtcga cgcccagagc acctgtgagc gtgagtgtac cggggaccag
 181 gactgtgcgg catccgagaa gtgctgcacc aatgtgtgtg ggctgcagag ctgcgtggct
 241 gcccgctttc ccagtggtgg cccagctgta cctgagacag cagcctcctg tgaaggcttc
 301 caatgcccac aacagggttc tgactgtgac atctgggatg gcagccagt tgtcgctgc
 361 cgtgaccgct gtgaaaaaga acccagcttc acatgtgctt ctgatggcct tacctattac
 421 aaccgctgct acatggacgc agaagcctgc ctgcggggtc tccacctgca cgttgtaccc
 481 tgtaagcaca ttctcagttg gccgcccagc agcccgggac cacccgagac cactgctcgc
 541 ccaaccccctg gggctgctcc catgccacct gcctgtaca acagcccctc accacaggca
 601 gtgcatgttg gggggacagc cagcctccac tgtgatgtta gtggccgtcc accacctgct
 661 gtgacctggg agaagcagag ccatcagcgg gagaacctga tcatgcgccc tgaccaaatg
 721 tatggcaacg tggttgtcac cagtatcgga cagctagtcc tctacaatgc tcagttggag
 781 gatgcgggcc tgtatacctg cactgcacga aacgctgccg gcctgctgcg ggccgacttt
 841 ccccttccg ttttacagcg ggcaactact caggacaggg acccaggtat cccagccttg
 901 gctgagtgcc aggccgacac acaagcctgt gttgggccac tactccccca tcatgtcctt
 961 tggcgctttg acccacagag aggcagctgc atgacattcc agccctcag atgtgatggg
1021 gctgcccggg gctttgagac ctatgaggca tgccagcagg cctgtgttcg tggccccggg
1081 gatgtctgtg cactgcctgc agttcagggg ccctgccagg gctgggagcc acgctgggcc
1141 tacagcccac tgctacagca gtgccacccc tttgtataca gtggctgtga aggaaacagc
1201 aataactttg agacccggga gagctgtgag gatgcttgcc ctgtaccacg cacaccaccc
1261 tgtcgtgcct gccgcctcaa gagcaagctg gctctgagct tgtgccgcag tgactttgcc
1321 atcgtgggga gactcacaga ggtcctggag gagcccgagg ctgcaggcgg catagctcgt
1381 gtggccttgg atgatgtgct aaaggacgac aagatgggcc tcaagttctt gggcaccaaa
1441 tacctggagg tgacattgag tggcatggac tgggcctgcc catgccccaa cgtgacagct
1501 gtcgatgggc cactggtcat catgggtgag gttcgtgaag gtgtggctgt gttggacgcc
1561 aacagctatg tccgtgctgc cagcgagaag cgagtcaaga agattgtgga actgctcgag
1621 aagaaggctt gtgaactgct caaccgcttc caagactag
```

*FIG. 8A*

PREDICTED MOUSE GASP2 AMINO ACID SEQUENCE
SEQ ID NO:9

```
  1 MPAPQPFLPL LFVFVLIHLT SETNLLPDPG SHPGMCPNEL SPHLWVDAQS TCERECTGDQ
 61 DCAASEKCCT NVCGLQSCVA ARFPSGGPAV PETAASCEGF QCPQQGSDCD IWDGQPVCRC
121 RDRCEKEPSF TCASDGLTYY NRCYMDAEAC LRGLHLHVVP CKHILSWPPS SPGPPETTAR
181 PTPGAAPMPP ALYNSPSPQA VHVGGTASLH CDVSGRPPPA VTWEKQSHQR ENLIMRPDQM
241 YGNVVVTSIG QLVLYNAQLE DAGLYTCTAR NAAGLLRADF PLSVLQRATT QDRDPGIPAL
301 AECQADTQAC VGPPTPHHVL WRFDPQRGSC MTFPALRCDG AARGFETYEA CQQACVRGPG
361 DVCALPAVQG PCQGWEPRWA YSPLLQQCHP FVYSGCEGNS NNFETRESCE DACPVPRTPP
421 CRACRLKSKL ALSLCRSDFA IVGRLTEVLE EPEAAGGIAR VALDDVLKDD KMGLKFLGTK
481 YLEVTLSGMD WACPCPNVTA VDGPLVIMGE VREGVAVLDA NSYVRAASEK RVKKIVELLE
541 KKACELLNRF QD
```

FIG. 8B

PREDICTED NUCLEOTIDE SEQUENCE OF HUMAN GASP2

SEQ ID NO:10

```
   1 atgcccgccc tacgtccact cctgccgctc ctgctcctcc tccggctgac ctcgggggct
  61 ggcttgctgc cagggctggg gagccacccg ggcgtgtgcc ccaaccagct cagccccaac
 121 ctgtgggtgg acgcccagag cacctgtgag cgcgagtgta gcagggacca ggactgtgcg
 181 gctgctgaga agtgctgcat caacgtgtgt ggactgcaca gctgcgtggc agcacgcttc
 241 cccggcagcc cagctgcgcc gacgacagcg gcctcctgcg agggctttgt gtgcccacag
 301 cagggctcgg actgcgacat ctgggacggg cagcccgtgt gccgctgccg cgaccgctgt
 361 gagaaggagc ccagcttcac ctgcgcctcg gacggcctca cctactacaa ccgctgctat
 421 atggacgccg aggcctgcct gcggggcctg cacctccaca tcgtgccctg caagcacgtg
 481 ctcagctggc cgcccagcag cccggggccg ccggagacca ctgcccgccc cacacctggg
 541 gccgcgcccg tgcctcctgc cctgtacagc agcccctccc cacaggcggt gcaggttggg
 601 ggtacggcca gcctccactg cgacgtcagc ggccgcccgc cgcctgctgt gacctgggag
 661 aagcagagtc accagcgaga gaacctgatc atgcgccctg atcagatgta tggcaacgtg
 721 gtggtcacca gcatcgggca gctggtgctc tacaacgcgc ggcccgaaga cgccggcctg
 781 tacacctgca ccgcgcgcaa cgctgctggg ctgctgcggg ctgacttccc actctctgtg
 841 gtccagcgag agccggccag ggacgcagcc cccagcatcc agccccggc cgagtgcctg
 901 ccggatgtgc aggcctgcac gggcccccact tccccacacc ttgtcctctg gcactacgac
 961 ccgcagcggg gcggctgcat gaccttcccg gccgtggct gtgatggggc ggcccgcggc
1021 tttgagacct acgaggcatg ccagcaggcc tgtgcccgcg gccccggcga cgcctgcgtg
1081 ctgcctgccg tgcagggccc ctgccggggc tgggagccgc gctgggccta cagcccgctg
1141 ctgcagcagt gccatcccctt cgtgtacggt ggctgcgagg caacggcaa caacttccac
1201 agccgcgaga gctgcgagga tgcctgcccc gtgccgcgca caccgccctg ccgcgcctgc
1261 cgcctccgga gcaagctggc gctgagcctg tgccgcagcg acttcgccat cgtggggcgg
1321 ctcacggagg tgctggagga gcccgaggcc gccggcggca tcgcccgcgt ggcgctcgag
1381 gacgtgctca aggatgacaa gatgggcctc aagttcttgg gcaccaagta cctggaggtg
1441 acgctgagtg gcatggactg ggcctgcccc tgccccaaca tgacggcggg cgacgggccg
1501 ctggtcatca tgggtgaggt gcgcgatggc gtggccgtgc tggacgccgg cagctacgtc
1561 cgcgccgcca gcgagaagcg cgtcaagaag atcttggagc tgctggagaa gcaggcctgc
1621 gagctgctca accgcttcca ggactagccc ccgcaggggc ctgcgccacc ccgtcctggt
1681 gaataaacgc actcc
```

*FIG. 9A*

PREDICTED AMINO ACID SEQUENCE OF HUMAN GASP-2

SEQ ID NO:11

```
  1 MPALRPLLPL LLLLRLTSGA GLLPGLGSHP GVCPNQLSPN LWVDAQSTCE RECSRDQDCA
 61 AAEKCCINVC GLHSCVAARF PGSPAAPTTA ASCEGFVCPQ QGSDCDIWDG QPVCRCRDRC
121 EKEPSFTCAS DGLTYYNRCY MDAEACLRGL HLHIVPCKHV LSWPPSSPGP PETTARPTPG
181 AAPVPPALYS SPSPQAVQVG GTASLHCDVS GRPPPAVTWE KQSHQRENLI MRPDQMYGNV
241 VVTSIGQLVL YNARPEDAGL YTCTARNAAG LLRADFPLSV VQREPARDAA PSIPAPAECL
301 PDVQACTGPT SPHLVLWHYD PQRGGCMTFP ARGCDGAARG FETYEACQQA CARGPGDACV
361 LPAVQGPCRG WEPRWAYSPL LQQCHPFVYG GCEGNGNNFH SRESCEDACP VPRTPPCRAC
421 RLRSKLALSL CRSDFAIVGR LTEVLEEPEA AGGIARVALE DVLKDDKMGL KFLGTKYLEV
481 TLSGMDWACP CPNMTAGDGP LVIMGEVRDG VAVLDAGSYV RAASEKRVKK ILELLEKQAC
541 ELLNRFQD
```

FIG. 9B

CLONED MOUSE GASP1 NUCLEOTIDE AND AMINO ACID SEQUENCES
SEQ ID NO: 48

```
        M   C   A   P   G       Y   H   R   F   W       F   H   W   G   L       L   L   L   L   L       L   E   A   P   L
   1  ATGTGTGCCCCAGGG TATCATCGGTTCTGG TTTCACTGGGGGCTG CTGTTGCTGCTGCTC CTCGAGGCTCCCCTT
        R   G   L   A   L       P   P   I   R   Y       S   H   A   G   I       C   P   N   D   M       N   P   N   L   W
  76  CGAGGCCTAGCACTG CCACCCATCCGATAC TCCCATGCGGGCATC TGCCCCAACGACATG AACCCCAACCTCTGG
        V   D   A   Q   S       T   C   K   R   E       C   E   T   D   Q       E   C   E   T   Y       E   K   C   C   P
 151  GTGGATGCCCAGAGC ACCTGCAAGCGAGAG TGTGAAACAGACCAG GAATGTGAGACCTAT GAGAAATGCTGCCCC
        N   V   C   G   T       K   S   C   V   A       A   R   Y   M   D       V   K   G   K   K       G   P   V   G   M
 226  AATGTGTGTGGGACC AAGAGCTGTGTGGCA GCCCGCTACATGGAT GTGAAAGGGAAGAAG GGGCCTGTAGGCATG
        P   K   E   A   T       C   D   H   F   M       C   L   Q   Q   G       S   E   C   D   I       W   D   G   Q   P
 301  CCCAAGGAGGCCACA TGTGACCATTTCATG TGCCTGCAGCAGGGC TCTGAGTGTGACATC TGGGACGGCCAGCCC
        V   C   K   C   K       D   R   C   E   K       E   P   S   F   T       C   A   S   D   G       L   T   Y   Y   N
 376  GTGTGTAAGTGCAAA GATCGCTGTGAGAAG GAGCCCAGCTTCACC TGTGCCTCTGATGGC CTTACCTACTACAAC
        R   C   F   M   D       A   E   A   C   S       K   G   I   T   L       S   V   V   T   C       R   Y   H   F   T
 451  CGTTGCTTCATGGAC GCCGAAGCCTGCTCC AAGGGCATCACACTG TCTGTGGTCACCTGT CGTTATCACTTCACC
        W   P   N   T   S       P   P   P   P   E       T   T   V   H   P       T   T   A   S   P       E   T   L   G   L
 526  TGGCCTAACACCAGC CCTCCACCGCCTGAG ACCACGGTGCATCCC ACCACCGCCTCTCCG GAGACTCTCGGGCTG
        D   M   A   A   P       A   L   L   N   H       P   V   H   Q   S       V   T   V   G   E       T   V   S   F   L
 601  GACATGGCAGCCCCA GCCCTGCTCAACCAC CCTGTCCATCAGTCA GTCACCGTGGGTGAG ACTGTGAGTTTCCTC
        C   D   V   V   G       R   P   R   P   E       L   T   W   E   K       Q   L   E   D   R       E   N   V   V   M
 676  TGTGACGTGGTAGGC CGGCCTCGGCCAGAG CTCACTTGGGAGAAA CAGCTGGAGGACCGA GAGAATGTTGTCATG
        R   P   N   H   V       R   G   N   V   V       V   T   N   I   A       Q   L   V   I   Y       N   V   Q   P   Q
 751  AGGCCCAACCACGTG CGTGGTAATGTGGTG GTCACTAACATTGCC CAGCTGGTCATCTAC AACGTCCAGCCCCAG
        D   A   G   I   Y       T   C   T   A   R       N   V   A   G   V       L   R   A   D   F       P   L   S   V   V
 826  GATGCTGGCATATAC ACCTGTACAGCTCGA AATGTCGCTGGTGTC CTGAGGGCTGACTTC CCGTTGTCGGTGGTC
        R   G   G   Q   A       R   A   T   S   E       S   S   L   N   G       T   A   F   P   A       T   E   C   L   K
 901  AGGGGTGGTCAGGCC AGGGCCACTTCAGAG AGCAGTCTCAATGGC ACAGCTTTTCCAGCA ACAGAGTGCCTGAAG
        P   P   D   S   E       D   C   G   E   E       Q   T   R   W   H       F   D   A   Q   A       N   N   C   L   T
 976  CCCCCAGACAGTGAG GACTGTGGAGAGGAG CAGACACGCTGGCAC TTCGACGCCCAGGCT AACAACTGCCTCACT
        F   T   F   G   H       C   H   H   N   L       N   H   F   E   T       Y   E   A   C   M       L   A   C   M   S
1051  TTCACCTTTGGCCAC TGCCACCACAATCTC AACCACTTTGAGACC TACGAGGCCTGTATG CTGGCTTGTATGAGT
        G   P   L   A   T       C   S   L   P   A       L   Q   G   P   C       K   A   Y   V   P       R   W   A   Y   N
1126  GGGCCATTGGCCACC TGCAGCCTGCCTGCC CTGCAAGGGCCTTGC AAAGCTTATGTCCCA CGCTGGGCCTACAAC
        S   Q   T   G   L       C   Q   S   F   V       Y   G   G   C   E       G   N   G   N   N       F   E   S   R   E
1201  AGCCAGACAGGCCTA TGCCAGTCCTTCGTC TATGGCGGCTGTGAG GGCAACGGTAACAAC TTTGAAAGCCGTGAG
        A   C   E   E   S       C   P   F   P   R       G   N   Q   H   C       R   A   C   K   P       R   Q   K   L   V
1276  GCTTGTGAGGAGTCG TGTCCCTTCCCGAGG GGTAACCAGCACTGC CGGGCCTGCAAGCCC CGGCAAAAACTTGTT
        T   S   F   C   R       S   D   F   V   I       L   G   R   V   S       E   L   T   E   E       Q   D   S   G   R
1351  ACCAGCTTCTGTCGG AGTGACTTTGTCATC CTGGGCAGGGTCTCT GAGCTGACCGAGGAG CAAGACTCGGGCCGT
        A   L   V   T   V       D   E   V   L   K       D   E   K   M   G       L   K   F   L   G       R   E   P   L   E
1426  GCCCTGGTGACCGTG GATGAGGTCTTAAAA GATGAGAAGATGGGC CTCAAGTTTCTGGGC CGGGAGCCTCTGGAA
        V   T   L   L   H       V   D   W   T   C       P   C   P   N   V       T   V   G   E   T       P   L   I   I   M
1501  GTCACCCTGCTTCAT GTAGACTGGACCTGT CCTTGCCCCAACGTG ACAGTGGGTGAGACA CCACTCATCATCATG
        G   E   V   D   G       G   M   A   M   L       R   P   D   S   F       V   G   A   S   S       T   R   R   V   R
1576  GGGGAGGTGGACGGC GGCATGGCCATGCTG AGACCCGATAGCTTT GTGGGGGCATCGAGC ACACGGCGGGTCAGG
        K   L   R   E   V       M   Y   K   K   T       C   D   V   L   K       D   F   L   G   L       Q   *
1651  AAGCTCCGTGAGGTC ATGTACAAGAAAACC TGTGACGTCCTCAAG GACTTCCTGGGCTTG CAATGA
```

*FIG. 13*

GASP1: A FOLLISTATIN DOMAIN CONTAINING PROTEIN

This application claims the benefit of U.S. Provisional Application No. 60/357,845, filed Feb. 21, 2002, and U.S. Provisional Application No. 60/434,644, filed Dec. 20, 2002.

FIELD OF THE INVENTION

The present invention relates to the use of proteins comprising at least one follistatin domain to modulate the level or activity of growth and differentiation factor-8 (GDF-8). More particularly, the invention relates to the use of proteins comprising at least one follistatin domain, excluding follistatin itself, for treating disorders that are related to modulation of the level or activity of GDF-8. The invention is useful for treating muscular diseases and disorders, particularly those in which an increase in muscle tissue would be therapeutically beneficial. The invention is also useful for treating diseases and disorders related to metabolism, adipose tissue, and bone degeneration.

BACKGROUND OF THE INVENTION

Growth and differentiation factor-8 (GDF-8), also known as myostatin, is a member of the transforming growth factor-beta (TGF-$\beta$) superfamily of structurally related growth factors, all of which possess important physiological growth-regulatory and morphogenetic properties (Kingsley et al. (1994) *Genes Dev.*, 8: 133–46; Hoodless et al. (1998) *Curr. Topics Microbiol. Immunol.*, 228: 235–72). GDF-8 is a negative regulator of skeletal muscle mass, and there is considerable interest in identifying factors which regulate its biological activity. For example, GDF-8 is highly expressed in the developing and adult skeletal muscle. The GDF-8 null mutation in transgenic mice is characterized by a marked hypertrophy and hyperplasia of the skeletal muscle (McPherron et al. (1997) *Nature*, 387: 83–90). Similar increases in skeletal muscle mass are evident in naturally occurring mutations of GDF-8 in cattle (Ashmore et al. (1974) *Growth*, 38: 501–507; Swatland and Kieffer (1994) *J. Anim. Sci.*, 38: 752–757; McPherron and Lee (1997) *Proc. Nat. Acad. Sci. U.S.A.*, 94: 12457–12461; and Kambadur et al. (1997) *Genome Res.*, 7: 910–915). Recent studies have also shown that muscle wasting associated with HIV-infection in humans is accompanied by increases in GDF-8 protein expression (Gonzalez-Cadavid et al. (1998) *Proc. Natl. Acad. Sci. U.S.A.*, 95: 14938–43). In addition, GDF-8 can modulate the production of muscle-specific enzymes (e.g., creatine kinase) and modulate myoblast cell proliferation (WO 00/43781).

A number of human and animal disorders are associated with loss of or functionally impaired muscle tissue. To date, very few reliable or effective therapies exist for these disorders. However, the terrible symptoms associated with these disorders may be substantially reduced by employing therapies that increase the amount of muscle tissue in patients suffering from the disorders. While not curing the conditions, such therapies would significantly improve the quality of life for these patients and could ameliorate some of the effects of these diseases. Thus, there is a need in the art to identify new therapies that may contribute to an overall increase in muscle tissue in patients suffering from these disorders.

In addition to its growth-regulatory and morphogenetic properties in skeletal muscle, GDF-8 may also be involved in a number of other physiological processes (e.g., glucose homeostasis), as well as abnormal conditions, such as in the development of type 2 diabetes and adipose tissue disorders, such as obesity. For example, GDF-8 modulates preadipocyte differentiation to adipocytes (Kim et al. (2001) *B.B.R.C.* 281: 902–906). Thus, modulation of GDF-8 may be useful for treating these diseases, as well.

The GDF-8 protein is synthesized as a precursor protein consisting of an amino-terminal propeptide and a carboxy-terminal mature domain (McPherron and Lee, (1997) *Proc. Nat. Acad. Sci. U.S.A.*, 94: 12457–12461). Before cleavage, the precursor GDF-8 protein forms a homodimer. The amino-terminal propeptide is then cleaved from the mature domain. The cleaved propeptide may remain noncovalently bound to the mature domain dimer, inactivating its biological activity (Miyazono et al. (1988) *J. Biol. Chem.*, 263: 6407–6415; Wakefield et al. (1988) *J. Biol. Chem.*, 263: 7646–7654; and Brown et al. (1990) *Growth Factors*, 3: 35–43). It is believed that two GDF-8 propeptides bind to the GDF-8 mature dimer (Thies et al. (2001) *Growth Factors*, 18: 251–259). Due to this inactivating property, the propeptide is known as the "latency-associated peptide" (LAP), and the complex of mature domain and propeptide is commonly referred to as the "small latent complex" (Gentry and Nash (1990) *Biochemistry*, 29:6851–6857; Derynck et al. (1995) *Nature*, 316:701–705; and Massague (1990) *Ann. Rev. Cell Biol.*, 12: 597–641). Other proteins are also known to bind to GDF-8 or structurally related proteins and inhibit their biological activity. Such inhibitory proteins include follistatin (Gamer et al. (1999) *Dev. Biol.*, 208: 222–232). The mature domain of GDF-8 is believed to be active as a homodimer when the propeptide is removed.

Clearly, GDF-8 is involved in the regulation of many critical biological processes. Due to its key function in these processes, GDF-8 may be a desirable target for therapeutic intervention. In particular, therapeutic agents that inhibit the activity of GDF-8 may be used to treat human or animal disorders in which an increase in muscle tissue would be therapeutically beneficial.

Known proteins comprising at least one follistatin domain play roles in many biological processes, particularly in the regulation of TGF-$\beta$ superfamily signaling and the regulation of extracellular matrix-mediated processes such as cell adhesion. Follistatin, follistatin related gene (FLRG, FSRP), and follistatin-related protein (FRP) have all been linked to TGF-$\beta$ signaling, either through transcriptional regulation by TGF-$\beta$ (Bartholin et al. (2001) *Oncogene*, 20: 5409–5419; Shibanuma et al. (1993) *Eur. J. Biochem.* 217: 13–19) or by their ability to antagonize TGF-$\beta$ signaling pathways (Phillips and de Kretser (1998) *Front. Neuroendocrin.*, 19: 287–322; Tsuchida et al. (2000) *J. Biol. Chem.*, 275: 40788–40796; Patel et al. (1996) *Dev. Biol*, 178: 327–342; Amthor et al. (1996) *Dev. Biol.*, 178: 343–362). Protein names in parentheses are alternative names.

Insulin growth factor binding protein 7 (IGFBP7, mac25), which comprise at least one follistatin domain, binds to insulin and blocks subsequent interaction with the insulin receptor. In addition, IGFBP7 has been shown to bind to activin, a TGF-$\beta$ family member (Kato (2000) *Mol. Med.*, 6:126–135).

Agrins and agrin related proteins contain upwards of nine follistatin domains and are secreted from nerve cells to promote the aggregation of acetylcholine receptors and other molecules involved in the formation of synapses. It has been suggested that the follistatin domains may serve to localize growth factors to the synapse (Patthy et al. (1993) *Trends Neurosci.*, 16: 76–81).

Osteonectin (SPARC, BM40) and hevin (SC1, mast9, QR1) are closely related proteins that interact with extracellular matrix proteins and regulate cell growth and adhesion (Motamed (1999) *Int. J. Biochem. Cell. Biol.*, 31: 1363–1366; Girard and Springer (1996) *J. Biol. Chem.*, 271: 4511–4517). These proteins comprise at least one follistatin domain.

Other follistatin domain proteins have been described or uncovered from the NCBI database (National Center for Biotechnology Information, Bethesda, Md., USA), however their functions are presently unknown. These proteins include U19878 (G01639, very similar to tomoregulin-1), T46914, human GASP1 (GDF-associated serum protein 1; described herein; FIG. 7), human GASP2 (WFIKKN; Trexier et al. (2001) *Proc. Natl. Acad. Sci. U.S.A.*, 98: 3705–3709; FIG. 9), and the proteoglycan family of testican (SPOCK) proteins (Alliel et al.(1993) *Eur. J. Biochem.*, 214: 347–350). Amino acid and nucleotide sequences for mouse GASP1 (FIG. 6) and mouse GASP2 (FIG. 8) were also determined from the Celera database (Rockville, Md.). As described herein, the nucleotide sequence of cloned mouse GASP1 matched the predicted Celera sequence, with the exception of some base substitutions in wobble codons that did not change the predicted amino acid sequence (see FIG. 13).

SUMMARY OF THE INVENTION

Accordingly, the invention relates to proteins, other than follistatin, comprising a unique structural feature, namely, the presence of at least one follistatin domain. Follistatin itself is not encompassed by the invention. The proteins comprising at least one follistatin domain are specifically reactive with a mature GDF-8 protein or a fragment thereof, whether the GDF-8 protein is in monomeric form, a dimeric active form, or complexed in the GDF-8 latent complex. Proteins comprising at least one follistatin domain may bind to an epitope on the mature GDF-8 protein that results in a reduction in one or more of the biological activities associated with GDF-8, relative to a mature GDF-8 protein that is not bound by the same protein.

The present invention provides methods for modulating the effects of GDF-8 on cells. Such methods comprise administering an effective amount of a protein comprising at least one follistatin domain. The present invention also encompasses methods for expressing a protein in a cell by administering a DNA molecule encoding a protein comprising at least one follistatin domain.

According to the invention, proteins comprising at least one follistatin domain may be administered to a patient, in a therapeutically effective dose, to treat or prevent medical conditions in which an increase in muscle tissue would be therapeutically beneficial. Embodiments include treatment of diseases, disorders, and injuries involving cells and tissue that are associated with the production, metabolism, or activity of GDF-8.

Proteins comprising at least one follistatin domain may be prepared in a pharmaceutical preparation. The pharmaceutical preparation may contain other components that aid in the binding of the mature GDF-8 protein or fragments thereof, whether it is in monomeric form, dimeric active form, or complexed in the GDF-8 latent complex.

In addition, proteins comprising at least one follistatin domain may be used as a diagnostic tool to quantitatively or qualitatively detect mature GDF-8 protein or fragments thereof, whether it is in monomeric form, dimeric active form, or complexed in the GDF-8 latent complex. For example, proteins comprising at least one follistatin domain may be used to detect the presence, absence, or amount of GDF-8 protein in a cell, bodily fluid, tissue, or organism. The presence or amount of mature GDF-8 protein detected may be correlated with one or more of the medical conditions listed herein.

Proteins comprising at least one follistatin domain may be provided in a diagnostic kit to detect mature GDF-8 protein or fragments thereof, whether it is in monomeric form, dimeric active form, or complexed in the GDF-8 latent complex, and help correlate the results with one or more of the medical conditions described herein. Such a kit may comprise at least one protein comprising at least one follistatin domain, whether it is labeled or unlabeled, and at least one agent that bind to this proteins, such as a labeled antibody. The kit may also include the appropriate biological standards and control samples to which one could compare the results of the experimental detection. It may also include buffers or washing solutions and instructions for using the kit. Structural components may be included on which one may carry out the experiment, such as sticks, beads, papers, columns, vials, or gels.

BRIEF DESCRIPTION OF THE FIGURES

FIG. 2 shows the identification of mature and unprocessed GDF-8 in affinity purified samples from normal mouse serum.

FIG. 6A shows the predicted nucleotide sequence to mouse GASP1. FIG. 6B shows a predicted alternative nucleotide sequence to mouse GASP1. FIG. 6C shows the predicted amino acid sequence encoded by the nucleotide sequences shown in FIGS. 6A and 6B. The protein sequences encoded by the two nucleotide sequences are identical because the nucleotide differences are all in wobble codon positions. The follistatin domain is shown in bold and underlined.

FIG. 7A shows the predicted nucleotide sequence of human GASP1. FIG. 7B shows the corresponding predicted amino acid sequence. The follistatin domain is shown in bold and underlined. FIG. 7C shows the predicted nucleotide sequence of human GASP1 using an alternative start site. FIG. 7D shows the corresponding predicted amino acid sequence. The follistatin domain is shown in bold and underlined. The end of the sequence is denoted by the asterisk.

FIG. 8A shows the predicted nucleotide sequence to mouse GASP2, while FIG. 8B shows the corresponding predicted amino acid sequence. The follistatin domain is shown in bold and underlined.

FIG. 9A shows the predicted nucleotide sequence to human GASP2, while FIG. 9B shows the corresponding predicted amino acid sequence. The follistatin domain is shown in bold and underlined.

FIG. 11 shows proteins isolated from human serum. Proteins from a JA16 immunoprecipitate or a control sample (0) were eluted in a mock PBS elution, a competing peptide elution, or a SDS elution. The proteins in the indicated regions of the gel were digested with trypsin and analyzed by LS-MS/MS and database searching. The proteins present in the JA16 sample but not in the control sample were mature GDF-8 (band 16), GDF-8 propeptide and FLRG (band 11), and human GASP1 (band 4).

FIG. 13 shows the nucleotide (SEQ ID NO:48) and amino acid (SEQ ID NO:49) sequences of cloned mouse GASP1. The peptides identified by mass spectrometry in JA16 affinity-purified samples are underlined. The end of the sequence is denoted by the asterisk.

DEFINITIONS

Figure 1:
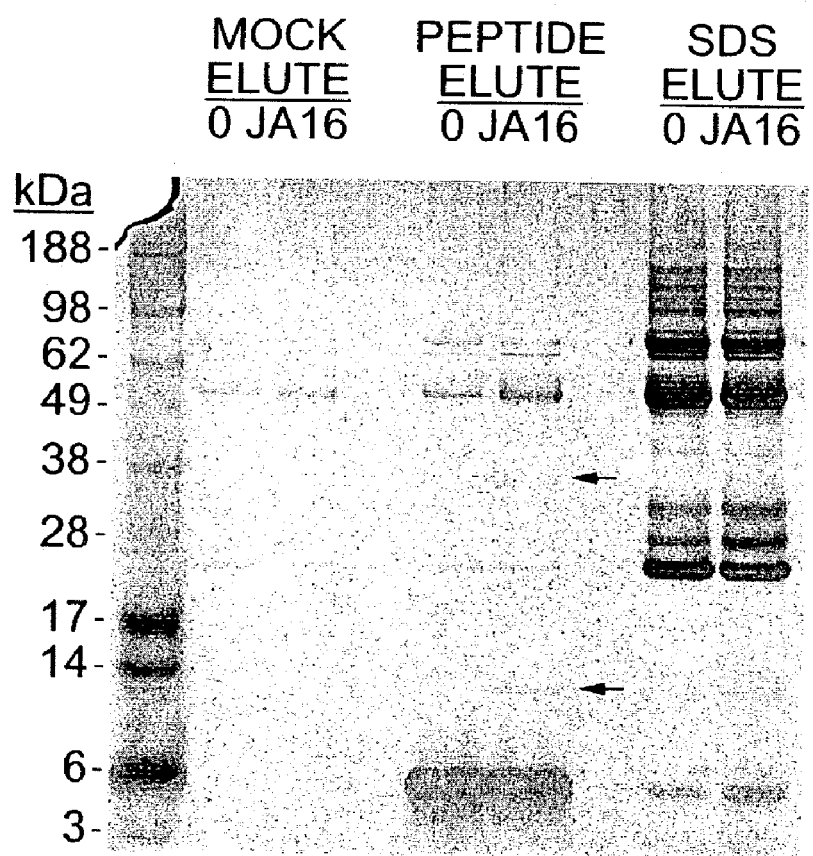
FIG. 1 shows antibody purification of the GDF-8 complex from wild-type mouse serum. A silver stained reducing gel shows proteins purified from wild type mouse serum using the JA16 monoclonal antibody covalently coupled to agarose beads. A control purification (0) with mock-coupled beads was performed in parallel. Subsequent elutions with buffer (mock elute), a competing peptide, and SDS sample buffer revealed two visible protein bands which were specifically eluted with peptide from the JA16-conjugated beads (indicated by arrows).

The term "follistatin domain" refers to an amino acid domain or a nucleotide domain encoding for an amino acid domain, characterized by cysteine rich repeats. A follistatin domain typically encompasses a 65–90 amino acid span and contains 10 conserved cysteine residues and a region similar to Kazal serine protease inhibitor domains. In general, the loop regions between the cysteine residues exhibit sequence variability in follistatin domains, but some conservation is evident. The loop between the fourth and fifth cysteines is usually small, containing only 1 or 2 amino acids. The amino acids in the loop between the seventh and eighth cysteines are generally the most highly conserved containing a consensus sequence of (G,A)-(S,N)-(S,N,T)-(D,N)-(G,N) followed by a (T,S)-Y motif. The region between the ninth and tenth cysteines generally contains a motif containing two hydrophobic residues (specifically V, I, or L) separated by another amino acid.

The term "protein comprising at least one follistatin domain" refers to proteins comprising at least one, but possibly more than one follistatin domain. The term also refers to any variants of such proteins (including fragments; proteins with substitution, addition or deletion mutations; and fusion proteins) that maintain the known biological activities associated with the native proteins, especially those pertaining to GDF-8 binding activity, including sequences that have been modified with conservative or non-conservative changes to the amino acid sequence. These proteins may be derived from any source, natural or synthetic. The protein may be human or derived from animal sources, including bovine, chicken, murine, rat, porcine, ovine, turkey, baboon, and fish. Follistatin itself is not encompassed by the invention.

The terms "GDF-8" or "GDF-8 protein" refer to a specific growth and differentiation factor. The terms include the full length unprocessed precursor form of the protein, as well as the mature and propeptide forms resulting from post-translational cleavage. The terms also refer to any fragments of GDF-8 that maintain the known biological activities associated with the protein, including sequences that have been modified with conservative or non-conservative changes to the amino acid sequence. These GDF-8 molecules may be derived from any source, natural or synthetic. The protein may be human or derived from animal sources, including bovine, chicken, murine, rat, porcine, ovine, turkey, baboon, and fish. Various GDF-8 molecules have been described in McPherron et al. (1997) *Proc. Natl. Acad. Sci. USA,* 94: 12457–12461.

"Mature GDF-8" refers to the protein that is cleaved from the carboxy-terminal domain of the GDF-8 precursor protein. The mature GDF-8 may be present as a monomer, homodimer, or in a GDF-8 latent complex. Depending on the in vivo or in vitro conditions, mature GDF-8 may establish an equilibrium between any or all of these different forms. It is believed to be biologically active as homodimer. In its biologically active form, the mature GDF-8 is also referred to as "active GDF-8."

"GDF-8 propeptide" refers to the polypeptide that is cleaved from the amino-terminal domain of the GDF-8 precursor protein. The GDF-8 propeptide is capable of binding to the propeptide binding domain on the mature GDF-8.

"GDF-8 latent complex" refers to the complex of proteins formed between the mature GDF-8 homodimer and the GDF-8 propeptide. It is believed that two GDF-8 propeptides associate with the two molecules of mature GDF-8 in the homodimer to form an inactive tetrameric complex. The latent complex may include other GDF inhibitors in place of or in addition to one or more of the GDF-8 propeptides.

The phrase "GDF-8 activity" refers to one or more of physiologically growth-regulatory or morphogenetic activities associated with active GDF-8 protein. For example, active GDF-8 is a negative regulator of skeletal muscle. Active GDF-8 can also modulate the production of muscle-specific enzymes (e.g., creatine kinase), stimulate myoblast cell proliferation, and modulate preadipocyte differentiation to adipocytes. GDF-8 is also believed to increase sensitivity to insulin and glucose uptake in peripheral tissues, particularly in skeletal muscle or adipocytes. Accordingly, GDF-8 biological activities include but are not limited to inhibition of muscle formation, inhibition of muscle cell growth, inhibition of muscle development, decrease in muscle mass, regulation of muscle-specific enzymes, inhibition of myoblast cell proliferation, modulation of preadipocyte differentiation to adipocytes, increasing sensitivity to insulin, regulations of glucose uptake, glucose hemostasis, and modulate neuronal cell development and maintenance.

The terms "isolated" or "purified" refer to a molecule that is substantially free of its natural environment. For instance, an isolated protein is substantially free of cellular material or other contaminating proteins from the cell or tissue source from which it is derived. The phrase "substantially free of cellular material" refers to preparations where the isolated protein is at least 70% to 80% (w/w) pure, at least 80%–89% (w/w) pure, at least 90–95% pure, or at least 96%, 97%, 98%, 99% or 100% (w/w) pure.

The term "LC-MS/MS" refers to liquid chromatography in line with a mass spectrometer programmed to isolate a molecular ion of particular mass/charge ratio, fragment this ion, and record the mass/charge ratio of the fragment ions. When analyzing peptide samples this technique allows upstream separation of complex samples through liquid chromatography, followed by the recording of fragment ion masses and subsequent determination of the peptide sequence.

The term "MS/MS" refers to the process of using a mass spectrometer to isolate a molecular ion of a particular mass/charge ratio, fragment this ion, and record the mass/charge ratio of the resulting fragment ions. The fragment ions provide information about the sequence of a peptide.

The term "treating" or "treatment" refers to both therapeutic treatment and prophylactic or preventative measures. Those in need of treatment may include individuals already having a particular medical disorder as well as those who may ultimately acquire the disorder (i.e., those needing preventative measures). The term treatment includes both measures that address the underlying cause of a disorder and measures that reduce symptoms of a medical disorder without necessarily affecting its cause. Thus, improvement of quality of life and amelioration of symptoms are considered treatment, as are measures that counteract the cause of a disorder.

The term "medical disorder" refers to disorders of muscle, bone, or glucose homeostasis, and include disorders associated with GDF-8 and/or other members of the TGF-β superfamily (e.g., BMP-11). Examples of such disorders include, but are not limited to, metabolic diseases and disorders such as insulin-dependent (type 1) diabetes mellitus, noninsulin-dependent (type 2) diabetes mellitus, hyperglycemia, impaired glucose tolerance, metabolic syndrome (e.g., syndrome X), and insulin resistance induced by trauma (e.g., burns or nitrogen imbalance), and adipose tissue disorders (e.g., obesity); muscle and neuromuscular disorders such as muscular dystrophy (including but not limited to severe or benign X-linked muscular dystrophy, limb-girdle dystrophy, facioscapulohumeral dystrophy, myotinic dystrophy, distal muscular dystrophy, progressive dystrophic ophthalmoplegia, oculopharyngeal dystrophy, Duchenne's muscular dystrophy, and Fakuyama-type congenital muscular dystophy); amyotrophic lateral sclerosis (ALS); muscle atrophy; organ atrophy; frailty; carpal tunnel syndrome; congestive obstructive pulmonary disease; congenital myopathy; myotonia congenital; familial periodic paralysis; paroxysmal myoglobinuria; myasthenia gravis; Eaton-Lambert syndrome; secondary myasthenia; denervation atrophy; paroxymal muscle atrophy; and sarcopenia, cachexia and other muscle wasting syndromes. Other examples include osteoporosis, especially in the elderly and/or postmenopausal women; glucocorticoid-induced osteoporosis; osteopenia; osteoarthritis; osteoporosis-related fractures; and traumatic or chronic injury to muscle tissue. Yet further examples include low bone mass due to chronic glucocorticoid therapy, premature gonadal failure, androgen suppression, vitamin D deficiency, secondary hyperparathyroidism, nutritional deficiencies, and anorexia nervosa.

The term "increase in mass" refers to the presence of a greater amount of muscle after treatment with proteins comprising at least one follistatin domain relative to the amount of muscle mass present before the treatment.

The term "therapeutic benefit" refers to an improvement of symptoms of a disorder, a slowing of the progression of a disorder, or a cessation in the progression of a disorder. The therapeutic benefit is determined by comparing an aspect of a disorder, such as the amount of muscle mass, before and after at least one protein comprising at last one follistatin domain is administered.

The term "modulating" refers to varying a property of a protein by increasing, decreasing, or inhibiting the activity, behavior, or amount of the protein. For example, proteins comprising at least one follistatin domain may modulate GDF-8 by inhibiting its activity.

The term "stabilizing modification" is any modification known in the art or set forth herein capable of stabilizing a protein, enhancing the in vitro half life of a protein, enhancing circulatory half life of a protein and/or reducing proteolytic degradation of a protein. Such stabilizing modifications include but are not limited to fusion proteins (including, for example, fusion proteins comprising a protein comprising at least one follistatin domain and a second protein), modification of a glycosylation site (including, for example, addition of a glycosylation site to a protein comprising at least one follistatin domain), and modification of carbohydrate moiety (including, for example, removal of carbohydrate moieties from a protein comprising at least one follistatin domain). In the case of a stabilizing modification which comprises a fusion protein (e.g., such that a second protein is fused to a protein comprising at least one follistatin domain), the second protein may be referred to as a "stabilizer portion" or "stabilizer protein." For example, a protein a human protein comprising at least one follistatin domain may be fused with an IgG molecule, wherein IgG acts as the stabilizer protein or stabilizer portion. As used herein, in addition to referring to a second protein of a fusion protein, a "stabilizer portion" also includes nonproteinaceous modifications such as a carbohydrate moiety, or nonproteinaceous polymer.

The term "Fc region of an IgG molecule" refers to the Fc domain of an immunoglobulin of the isotype IgG, as is well known to those skilled in the art. The Fc region of an IgG molecule is that portion of IgG molecule (IgG1, IgG2, IgG3, and IgG4) that is responsible for increasing the in vivo serum half-life of the IgG molecule.

"In vitro half life" refers to the stability of a protein measured outside the context of a living organism. Assays to measure in vitro half life are well known in the art and include but are not limited to SDS-PAGE, ELISA, cell-based assays, pulse-chase, western blotting, northern blotting, etc. These and other useful assays are well known in the art.

"In vivo half life" refers to the stability of a protein in an organism. In vivo half life may be measured by a number of methods known in the art including but not limited to in vivo serum half life, circulatory half life, and assays set forth in the examples herein.

"in vivo serum half life" refers to the half-life of a protein circulating in the blood of an organism. Methods known in the art may be used to measure in vivo serum half life. For example, radioactive protein can be administered to an animal and the amount of labeled protein in the serum can be monitored over time.

To assist in the identification of the sequences listed in the specification and figures, the following table is provided, which lists the SEQ ID NO, the figure location, and a description of the sequence.

| SEQ ID NO: | REFERENCE | DESCRIPTION |
|---|---|---|
| 1 | FIG. 6A | predicted mouse GASP1 nucleotide sequence |
| 2 | FIG. 6B | predicted mouse GASP1 alternative nucleotide sequence |
| 3 | FIG. 6C | predicted mouse GASP1 amino acid sequence encoded by both SEQ ID NOS: 1 and 2 |
| 4 | FIG. 7A | predicted human GASP1 nucleotide sequence |
| 5 | FIG. 7B | predicted human GASP1 amino acid sequence |
| 6 | FIG. 7C | predicted human GASP1 nucleotide sequence, alternative start site |
| 7 | FIG. 7D | predicted human GASP1 amino acid sequence, alternative start site encoded by SEQ ID NO:6 |
| 8 | FIG. 8A | predicted mouse GASP2 nucleotide sequence |
| 9 | FIG. 8B | predicted mouse GASP2 amino acid sequence encoded by SEQ ID NO:8 |
| 10 | FIG. 9A | predicted human GASP2 nucleotide sequence |
| 11 | FIG. 9B | predicted human GASP2 amino acid sequence encoded by SEQ ID NO:10 |
| 12 | Example 2 | competing peptide |
| 13–20 | Table 1, Examples 5, 6 | mouse GDF-8 peptides |
| 21–27 | Table 1, Examples 5, 6 | mouse GDF-8 propeptide peptides |
| 28–30 | Table 1, Example 5 | mouse FLRG peptides |
| 31–35 | Table 1, Examples 5, 7 | mouse GASP1 peptides |
| 36–37 | Table 1, Example 8 | human GDF-8 peptides |
| 38–39 | Table 1, Example 8 | human GDF-8 propeptide peptides |
| 40–42 | Table 1, Example 8 | human FLRG peptides |
| 43–45 | Table 1, Example 8 | human GASP1 peptides |
| 46 | Example 7 | forward primer |
| 47 | Example 7 | reverse primer |
| 48 | FIG. 13 | cloned mouse GASP1 nucleotide sequence |
| 49 | FIG. 13 | cloned mouse GASP1 amino acid sequence encoded by SEQ ID NO:48 |
| 50 | Example 9 | forward primer |
| 51 | Example 9 | reverse primer |
| 52 | Example 9 | illustrative N-terminal peptide sequence |
| 53 | Example 11 | synthetic oligonucleotide |

DETAILED DESCRIPTION OF THE INVENTION

Proteins Comprising at Least One Follistatin Domain

The present invention relates to proteins, other than follistatin, having a unique structural feature, namely, that they comprise at least one follistatin domain. Follistatin itself is not encompassed by the invention. It is believed that proteins containing at least one follistatin domain will bind and inhibit GDF-8. Examples of proteins having at least one follistatin domain include, but are not limited to follistatin-like related gene (FLRG), FRP (flik, tsc 36), agrins, osteonectin (SPARC, BM40), hevin (SC1, mast9, QR1), IGFBP7 (mac25), and U19878. GASP1, comprising the nucleotide and amino acid sequences provided in FIGS. 6 and 7, and GASP2, comprising the nucleotide and amino acid sequences provided in FIGS. 8 and 9, are other examples of proteins comprising at least one follistatin domain.

A follistatin domain, as stated above, is defined as an amino acid domain or a nucleotide domain encoding for an amino acid domain, characterized by cysteine rich repeats. A follistatin domain typically encompasses a 65–90 amino acid span and contains 10 conserved cysteine residues and a region similar to Kazal serine protease inhibitor domains. In general, the loop regions between the cysteine residues exhibit sequence variability in follistatin domains, but some conservation is evident. The loop between the fourth and fifth cysteines is usually small, containing only 1 or 2 amino acids. The amino acids in the loop between the seventh and eighth cysteines are generally the most highly conserved containing a consensus sequence of (G,A)-(S,N)-(S,N,T)-(D,N)-(G,N) followed by a (T,S)-Y motif. The region between the ninth and tenth cysteines generally contains a motif containing two hydrophobic residues (specifically V, I, or L) separated by another amino acid.

Proteins comprising at least one follistatin domain, which may bind GDF-8, may be isolated using a variety of methods. For example, one may use affinity purification using GDF-8, as exemplified in the present invention. In addition, one may use a low stringency screening of a cDNA library, or use degenerate PCR techniques using a probe directed toward a follistatin domain. As more genomic data becomes available, similarity searching using a number of sequence profiling and analysis programs, such as MotifSearch (Genetics Computer Group, Madison, Wis.), ProfileSearch (GCG), and BLAST (NCBI) could be used to find novel proteins containing significant homology with known follistatin domains.

One of skill in the art will recognize that both GDF-8 or proteins comprising at least one follistatin domain may contain any number of conservative changes to their respective amino acid sequences without altering their biological properties. Such conservative amino acid modifications are based on the relative similarity of the amino acid side-chain substituents, for example, their hydrophobicity, hydrophilicity, charge, size, and the like. Exemplary conservative substitutions which take various of the foregoing characteristics into consideration are well known to those of skill in the art and include: arginine and lysine; glutamate and aspartate; serine and threonine; glutamine and asparagine; and valine, leucine, and isoleucine. Furthermore, proteins comprising at least one follistatin domain may be used to generate functional fragments comprising at least one follistatin domain. It is expected that such fragments would bind and inhibit GDF-8. In an embodiment of the invention, proteins comprising at least one follistatin domain specifically bind to mature GDF-8 or a fragment thereof, whether it is in monomeric form, active dimer form, or complexed in a GDF-8 latent complex, with an affinity of between 0.001 and 100 nM, or between 0.01 and 10 nM, or between 0.1 and 1 nM.

Nucleotide and Protein Sequences

While not always necessary, if desired, one of ordinary skill in the art may determine the amino acid or nucleic acid sequences of a novel proteins comprising at least one follistatin domain. For example, the present invention provides the amino acid and nucleotide sequences for GASP1 and GASP2, as shown in FIGS. 6–9.

The present invention also include variants, homologues, and fragments of such nucleic and amino acid sequences. For example, the nucleic or amino acid sequence may comprise a sequence at least 70% to 79% identical to the nucleic or amino acid sequence of the native protein, or at least 80% to 89% identical, or at least 90% to 95% identical, or at least 96% to 100% identical. One of skill in the art will recognize that the region that binds GDF-8 can tolerate less sequence variation than the other portions of the protein not involved in binding. Thus, these non-binding regions of the protein may contain substantial variations without significantly altering the binding properties of the protein. However, one of skill in the art will also recognize that many changes can be made to specifically increase the affinity of the protein for its target. Such affinity-increasing changes are typically determined empirically by altering the protein, which may be in the binding region, and testing the ability to bind GDF-8 or the strength of the binding. All such alterations, whether within or outside the binding region, are included in the scope of the present invention.

Relative sequence similarity or identity may be determined using the "Best Fit" or "Gap" programs of the Sequence Analysis Software Package™ (Version 10; Genetics Computer Group, Inc., University of Wisconsin Biotechnology Center, Madison, Wis.). "Gap" utilizes the algorithm of Needleman and Wunsch (Needleman and Wunsch, 1970) to find the alignment of two sequences that maximizes the number of matches and minimizes the number of gaps. "BestFit" performs an optimal alignment of the best segment of similarity between two sequences. Optimal alignments are found by inserting gaps to maximize the number of matches using the local homology algorithm of Smith and Waterman (Smith and Waterman, 1981; Smith, et al., 1983).

The Sequence Analysis Software Package described above contains a number of other useful sequence analysis tools for identifying homologues of the presently disclosed nucleotide and amino acid sequences. For example, the "BLAST" program (Altschul, et al., 1990) searches for sequences similar to a query sequence (either peptide or nucleic acid) in a specified database (e.g., sequence databases maintained at the NCBI; "FastA" (Lipman and Pearson, 1985; see also Pearson and Lipman, 1988; Pearson, et al., 1990) performs a Pearson and Lipman search for similarity between a query sequence and a group of sequences of the same type (nucleic acid or protein); "TfastA" performs a Pearson and Lipman search for similarity between a protein query sequence and any group of nucleotide sequences (it translates the nucleotide sequences in all six reading frames before performing the comparison); "FastX" performs a Pearson and Lipman search for similarity between a nucleotide query sequence and a group of protein sequences, taking frameshifts into account. "TfastX" performs a Pearson and Lipman search for similarity between a protein query sequence and any group of nucleotide sequences, taking frameshifts into account (it translates both strands of the nucleic sequence before performing the comparison).

Modified Proteins

The invention encompasses fragments of proteins comprising at least one follistatin domain. Such fragments will likely include all or a part of the follistatin domain. Fragments may include all, a part, or none of the sequences between the follistatin domain and the N-terminus and/or between the follistatin domain and the C-terminus.

It is understood by one of ordinary skill in the art that certain amino acids may be substituted for other amino acids in a protein structure without adversely affecting the activity of the protein, e.g., binding characteristics of a protein comprising at least one follistatin domain. It is thus contemplated by the inventors that various changes may be made in the amino acid sequences of proteins comprising at least one follistatin domain, or DNA sequences encoding the proteins, without appreciable loss of their biological utility or activity. Such changes may include deletions, insertions, truncations, substitutions, fusions, shuffling of motif sequences, and the like.

In making such changes, the hydropathic index of amino acids may be considered. The importance of the hydropathic amino acid index in conferring interactive biological function on a protein is generally understood in the art (Kyte and Doolittle (1982) *J. Mol. Biol.*, 157: 105–132). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle, 1982); these are isoleucine (+4.5), valine (+4.2), leucine (+3.8), phenylalanine (+2.8), cysteine/cystine (+2.5), methionine (+1.9), alanine (+1.8), glycine (−0.4), threonine (−0.7), serine (−0.8), tryptophan (−0.9), tyrosine (−1.3), proline (−1.6), histidine (−3.2), glutamate (−3.5), glutamine (−3.5), aspartate (−3.5), asparagine (−3.5), lysine (−3.9), and arginine (−4.5). In making such changes, the substitution of amino acids whose hydropathic indices may be within ±2, within ±1, and within ±0.5.

It is also understood in the art that the substitution of like amino acids can be made effectively on the basis of hydrophilicity. U.S. Pat. No. 4,554,101 states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0), lysine (+3.0), aspartate (+3.0±1), glutamate (+3.0±1), serine (+0.3), asparagine (+0.2), glutamine (+0.2), glycine (0), threonine (−0.4), proline (−0.5±1), alanine (−0.5), histidine (−0.5), cysteine (−1.0), methionine (−1.3), valine (−1.5), leucine (−1.8), isoleucine (−1.8), tyrosine (−2.3), phenylalanine (−2.5), and tryptophan (−3.4). In making such changes, the substitution of amino acids whose hydrophilicity values may be within ±2, within ±1, and within ±0.5.

The modifications may be conservative such that the structure or biological function of the protein is not affected by the change. Such conservative amino acid modifications are based on the relative similarity of the amino acid side-chain substituents, for example, their hydrophobicity, hydrophilicity, charge, size, and the like. Exemplary conservative substitutions which take various of the foregoing characteristics into consideration are well known to those of skill in the art and include: arginine and lysine; glutamate and aspartate; serine and threonine; glutamine and asparagine; and valine, leucine, and isoleucine. The amino acid sequence of proteins comprising at least one follistatin domain may be modified to have any number of conservative changes, so long as the binding of the protein to its target antigen is not adversely affected. Such changes may be introduced inside or outside of the binding portion of the protein comprising at least one follistatin domain. For example, changes introduced inside of the antigen binding portion of the protein may be designed to increase the affinity of the protein for its target.

Stabilizing Modification

Stabilizing modifications are capable of stabilizing a protein, enhancing the in vitro and/or in vivo half life of a protein, enhancing circulatory half life of a protein and/or reducing proteolytic degradation of a protein. Such stabilizing modifications include but are not limited to fusion proteins, modification of a glycosylation site, and modification of carbohydrate moiety. A stabilizer protein may be any protein which enhances the overall stability of the modified GDF propeptide. As will be recognized by one of ordinary skill in the art, such fusion protein may optionally comprise a linker peptide between the propeptide portion and the stabilizing portion. As is well known in the art, fusion proteins are prepared such that the second protein is fused in frame with the first protein such that the resulting translated protein comprises both the first and second proteins. For example, in the present invention, a fusion protein may be prepared such that a protein comprising at least one follistatin domain is fused to a second protein (e.g. a stabilizer protein portion.) Such fusion protein is prepared such that the resulting translated protein contains both the propeptide portion and the stabilizer portion.

Proteins comprising at least one follistatin domain can be glycosylated or linked to albumin or a nonproteineous polymer. For instance, proteins comprising at least one follistatin domain may be linked to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337. Proteins are chemically modified by covalent conjugation to a polymer to increase their circulating half-life, for example. Polymers, and methods to attach them to peptides, are also shown in U.S. Pat. Nos. 4,766,106; 4,179,337; 4,495,285; and 4,609,546.

Proteins comprising at least one follistatin domain may be pegylated. Pegylation is a process whereby polyethylene glycol (PEG) is attached to a protein in order to extend the half-life of the protein in the body. Pegylation of proteins comprising at least one follistatin domain may decrease the dose or frequency of administration of the proteins needed for an optimal inhibition of GDF-8. Reviews of the technique are provided in Bhadra et al. (2002) *Pharmazie*, 57: 5–29, and in Harris et al. (2001) *Clin. Pharmacokinet.*, 40: 539–551.

Proteins comprising at least one follistatin domain can be linked to an Fc region of an IgG molecule. Proteins comprising at least one follistatin domain may be fused adjacent to the Fc region of the IgG molecule, or attached to the Fc region of the molecule via a linker peptide. Use of such linker peptides is well known in the protein biochemistry art. The Fc region may me derived from IgG1 or IgG4, for example.

Proteins comprising at least one follistatin domain may be modified to have an altered glycosylation pattern (i.e., altered from the original or native glycosylation pattern). As used herein, "altered" means having one or more carbohydrate moieties deleted, and/or having one or more glycosylation sites added to the original protein.

Glycosylation of proteins is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to proteins comprising at least one follistatin domain is conveniently accomplished by altering the amino acid sequence such that it contains one or more of the above-described tripeptide sequences (for N-linked glycosylation sites). The alteration may also be made by the addition of, or substitution by, one or more serine orthreonine residues to the sequence of the original protein (for O-linked glycosylation sites). For ease, the protein amino acid sequence may be altered through changes at the DNA level.

Another means of increasing the number of carbohydrate moieties on proteins is by chemical or enzymatic coupling of glycosides to the amino acid residues of the protein. These procedures are advantageous in that they do not require production of the GDF peptide inhibitor in a host cell that has glycosylation capabilities for N- or O-linked glycosylation. Depending on the coupling mode used, the sugars may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330, and in Aplin and Wriston (1981) *CRC Crit. Rev. Biochem.,* 22: 259–306.

Removal of any carbohydrate moieties present on proteins comprising at least one follistatin domain may be accomplished chemically or enzymatically. Chemical deglycosylation requires exposure of the protein to trifluoromethanesulfonic acid, or an equivalent compound. This treatment results in the cleavage of most or all sugars except the linking sugar (N-acetylglucosamine or N-acetylgalactosamine), while leaving the amino acid sequence intact.

Chemical deglycosylation is described by Hakimuddin et al. (1987) *Arch. Biochem. Biophys.,* 259: 52; and Edge et al. (1981) *Anal. Biochem.,* 118: 131. Enzymatic cleavage of carbohydrate moieties on GDF peptide inhibitors can be achieved by the use of a variety of endo- and exo-glycosidases as described by Thotakura et al. (1987) *Meth. Enzymol.,* 138: 350.

Proteins comprising at least one follistatin domain may be linked to the protein albumin or a derivative of albumin. Methods for linking proteins and polypeptides to albumin or albumin derivatives are well known in the art. See, for example, U.S. Pat. No. 5,116,944.

Pharmaceutical Compositions

The present invention provides compositions containing proteins comprising at least one follistatin domain. Such compositions may be suitable for pharmaceutical use and administration to patients. The compositions typically contain one or more proteins comprising at least one follistatin domain and a pharmaceutically acceptable excipient. As used herein, the phrase “pharmaceutically acceptable excipient” includes any and all solvents, dispersion media, coatings, antibacterial and antifungal agents, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions. The pharmaceutical compositions may also be included in a container, pack, or dispenser together with instructions for administration.

A pharmaceutical composition of the invention is formulated to be compatible with its intended route of administration. Methods to accomplish the administration are known to those of ordinary skill in the art. The administration may, for example, be intravenous, intramuscular, or subcutaneous.

Solutions or suspensions used for subcutaneous application typically include one or more of the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetra acetic acid; buffers such as acetates, citrates or phosphates; and agents for the adjustment of tonicity such as sodium chloride or dextrose. The pH can be adjusted with acids or bases, such as hydrochloric acid or sodium hydroxide. Such preparations may be enclosed in ampoules, disposable syringes or multiple dose vials made of glass or plastic.

Pharmaceutical compositions suitable for injection include sterile aqueous solutions or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, one may include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

In one embodiment, proteins comprising at least one follistatin domain are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Ind. Liposomal suspensions containing proteins comprising at least one follistatin domain can also be used as pharmaceutically acceptable carriers. These can be prepared according to methods known to those skilled in the art, for example, as described in U.S. Pat. No. 4,522,811.

Therapeutically useful agents, such as growth factors (e.g., BMPs, TGF-β, FGF, IGF), cytokines (e.g., interleukins and CDFs), antibiotics, and any other therapeutic agent beneficial for the condition being treated may optionally be included in or administered simultaneously or sequentially with, proteins comprising at least one follistatin domain.

It is especially advantageous to formulate compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Treatment Indications

Proteins comprising at least one follistatin domain are useful to prevent, diagnose, or treat various medical disorders in humans or animals. Accordingly, the present invention provides a method for treating diseases and disorders related to muscle cells and tissue, by administering to a subject a composition comprising at least one protein comprising at least one follistatin domain in an amount sufficient to ameliorate the symptoms of the disease. Such disorders include muscular dystrophies, including, but not limited to severe or benign X-linked muscular dystrophy, limb-girdle dystrophy, facioscapulohumeral dystrophy, myotinic dystrophy, distal muscular dystrophy, progressive dystrophic ophthalmoplegia, oculopharyngeal dystrophy, Duchenne's muscular dystrophy, and Fakuyama-type congenital muscular dystophy); amyotrophic lateral sclerosis (ALS); muscle atrophy; organ atrophy; frailty; carpal tunnel syndrome; congestive obstructive pulmonary disease; congenital myopathy; myotonia congenital; familial periodic paralysis; paroxysmal myoglobinuria; myasthenia gravis; Eaton-Lambert syndrome; secondary myasthenia; denervation atrophy; paroxymal muscle atrophy; and sarcopenia, cachexia and other muscle wasting syndromes. The invention also relates to traumatic or chronic injury to muscle tissue.

In addition to providing therapy for muscle diseases and disorders, the present invention also provides for methods for preventing or treating metabolic diseases or disorders resulting from abnormal glucose homeostasis. Such diseases or disorders include metabolic diseases and disorders (such as insulin-dependent (type 1) diabetes mellitus, noninsulin-dependent (type 2) diabetes mellitus), hyperglycemia, impaired glucose tolerance, metabolic syndrome (e.g., syndrome X), obesity and insulin resistance induced by trauma (e.g., burns or nitrogen imbalance), adipose tissue disorders (such as obesity), or bone degenerative diseases (such as osteoporosis, especially in the elderly and/or postmenopausal women; glucocorticoid-induced osteoporosis; osteopenia; osteoarthritis; and osteoporosis-related fractures). Yet further examples include low bone mass due to chronic glucocorticoid therapy, premature gonadal failure, androgen suppression, vitamin D deficiency, secondary hyperparathyroidism, nutritional deficiencies, and anorexia nervosa.

Normal glucose homeostasis requires the finely tuned orchestration of insulin secretion by pancreatic beta cells in response to subtle changes in blood glucose levels. One of the fundamental actions of insulin is to stimulate uptake of glucose from the blood into tissues, especially muscle and fat.

Accordingly, the present invention provides a method for treating diabetes mellitus and related disorders, such as obesity or hyperglycemia, by administering to a subject a composition comprising at least one protein comprising at least one follistatin domain in an amount sufficient to ameliorate the symptoms of the disease. Type 2 or noninsulin-dependent diabetes mellitus (NIDDM), in particular, is characterized by a triad of (1) resistance to insulin action on glucose uptake in peripheral tissues, especially skeletal muscle and adipocytes, (2) impaired insulin action to inhibit hepatic glucose production, and (3) dysregulated insulin secretion (DeFronzo (1997) *Diabetes Rev.* 5: 177–269). Therefore, subjects suffering from type 2 diabetes can be treated according to the present invention by administration of protein comprising at least one follistatin domain, which increases sensitivity to insulin and glucose uptake by cells.

Similarly, other diseases and metabolic disorders characterized by insulin dysfunction (e.g., resistance, inactivity, or deficiency) and/or insufficient glucose transport into cells also can be treated according to the present invention by administration of a protein comprising at least one follistatin domain, which increases sensitivity to insulin and glucose uptake by cells.

Methods of Treatment Using Proteins

Proteins comprising at least one follistatin domain may be used to inhibit or reduce one or more activities associated with the GDF-8 protein (whether in monomeric form, dimeric active form, or complexed in a GDF-8 latent complex), relative to a GDF-8 protein not bound by the same protein. In an embodiment, the activity of the mature GDF-8 protein, when bound by a protein comprising at least one follistatin domain, is inhibited at least 50%, or at least 60, 62, 64, 66, 68, 70, 72, 72, 76, 78, 80, 82, 84, 86, or 88%, or at least 90, 91, 92, 93, or 94%, or at least 95% to 100% relative to a mature GDF-8 protein that is not bound by a protein having a follistatin domain.

Pharmaceutical preparations comprising proteins comprising at least one follistatin domain are administered in therapeutically effective amounts. As used herein, an "effective amount" of the protein is a dosage which is sufficient to reduce the activity of GDF-8 to achieve a desired biological outcome. The desired biological outcome may be any therapeutic benefit including an increase in muscle mass, an increase in muscle strength, improved metabolism, decreased adiposity, or improved glucose homeostasis. Such improvements may be measured by a variety of methods including those that measure lean and fat body mass (such as duel x-ray scanning analysis), muscle strength, serum lipids, serum leptin, serum glucose, glycated hemoglobin, glucose tolerance, and improvement in the secondary complication of diabetes.

Generally, a therapeutically effective amount may vary with the subject's age, condition, and sex, as well as the severity of the medical condition in the subject. The dosage may be determined by an physician and adjusted, as necessary, to suit observed effects of the treatment. Appropriate dosages for administering at least one protein comprising at least one follistatin domain may range from 5 mg to 100 mg, from 15 mg to 85 mg, from 30 mg to 70 mg, or from 40 mg to 60 mg. Proteins can be administered in one dose, or at intervals such as once daily, once weekly, and once monthly. Dosage schedules can be adjusted depending on the affinity of the protein for GDF-8, the half life of the protein, or the severity of the patient's condition. Generally, the compositions are administered as a bolus dose, to maximize the circulating levels of proteins comprising at least one follistatin domain for the greatest length of time after the dose. Continuous infusion may also be used after the bolus dose.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Proteins comprising at least one follistatin domain which exhibit large therapeutic indices may be used.

Data obtained from the cell culture assays and animal studies can be used in evaluating a range of dosage for use in humans. The dosage of such compounds may lie within a range of circulating concentrations that include the $ED_{50}$ with little or no toxicity. The dosage may vary within this range depending upon the dosage form employed and the route of administration utilized. For any protein comprising at least one follistatin domain used in the present invention, the therapeutically effective dose can be estimated initially from cell culture assays. A dose may be formulated in animal models to achieve a circulating plasma concentration range that includes the $IC_{50}$ (i.e., the concentration of the test protein which achieves a half-maximal inhibition of symptoms) as determined in cell culture. Levels in plasma may be measured, for example, by high performance liquid chromatography. The effects of any particular dosage can be monitored by a suitable bioassay. Examples of suitable bioassays include GDF-8 protein/receptor binding assays, creatine kinase assays, assays based on glucose uptake in adipocytes, and immunological assays.

Methods of Administering DNA

The present invention also provides gene therapy for the in vivo production of proteins comprising at least one follistatin domain. Such therapy would achieve its therapeutic effect by introduction of the polynucleotide sequences into cells or tissues having the disorders as listed herein.

Delivery of polynucleotide sequences of proteins comprising at least one follistatin domain can be achieved using a recombinant expression vector such as a chimeric virus or a colloidal dispersion system. Target liposomes may be used for therapeutic delivery of the polynucleotide sequences. Various viral vectors which can be utilized for gene therapy include adenovirus, herpes virus, vaccinia, or an RNA virus such as a retrovirus. The retroviral vector may be a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous sarcoma virus (RSV). A number of additional retroviral vectors can incorporate multiple genes. All of these vectors can transfer or incorporate a gene for a selectable marker so that transduced cells can be identified and generated. By inserting a GDF propeptide polynucleotide sequence of interest into the viral vector, along with another gene which encodes the ligand for a receptor on a specific target cell, for example, the vector is now target specific.

Retroviral vectors can be made target specific by attaching, for example, a sugar, a glycolipid, or a protein. Targeting may be accomplished by using an antibody. Those of skill in the art will recognize that specific polynucleotide sequences can be inserted into the retroviral genome or attached to a viral envelope to allow target specific delivery of the retroviral vector containing the polynucleotide of proteins comprising at least one follistatin domain. In one embodiment, the vector is targeted to muscle cells or muscle tissue.

Since recombinant retroviruses are defective, they require helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include, but are not limited to PSI.2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for a polynucleotide of a protein comprising at least one follistatin domain is a colloidal dispersion system. Colloidal dispersion systems include macromolecule complexes, nanocapsules, microspheres, beads, and lipid-based systems including oil-in-water emulsions, micelles, mixed micelles, and liposomes. Liposomes are artificial membrane vesicles which are useful as delivery vehicles in vitro and in vivo. RNA, DNA and intact virions can be encapsulated within the aqueous interior and be delivered to cells in a biologically active form (see, for example, Fraley, et al. (1981) *Trends Biochem. Sci.*, 6: 77). Methods for efficient gene transfer using a liposome vehicle, are known in the art (see, for example, Mannino, et a. (1988) *Biotechniques*, 6: 682. The composition of the liposome is usually a combination of phospholipids, usually in combination with steroids, especially cholesterol. Other phospholipids or other lipids may also be used. The physical characteristics of liposomes depend on pH, ionic strength; and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Illustrative phospholipids include egg phosphatidylcholine, dipalmitoylphosphatidylcholine and distearoylphosphatidylcholine. The targeting of liposomes is also possible based on, for example, organ-specificity, cell-specificity, and organelle-specificity and is known in the art.

There is a wide range of methods which can be used to deliver the cells expressing proteins comprising at least one follistatin domain to a site for use in modulating a GDF-8 response. In one embodiment of the invention, the cells expressing follistatin protein can be delivered by direct application, for example, direct injection of a sample of such cells into the site of tissue damage. These cells can be purified. The such cells can be delivered in a medium or matrix which partially impedes their mobility so as to localize the cells to a site of injury. Such a medium or matrix could be semi-solid, such as a paste or gel, including a gel-like polymer. Alternatively, the medium or matrix could be in the form of a solid, a porous solid which will allow the migration of cells into the solid matrix, and hold them there while allowing proliferation of the cells.

Methods of Detection and Isolation of GDF-8

Proteins comprising at least one follistatin domain may be used to detect the presence or level of GDF-8, in vivo or in vitro. By correlating the presence or level of these proteins with a medical condition, one of skill in the art can diagnose the associated medical condition. The medical conditions that may be diagnosed by the proteins comprising at least one follistatin domain are set forth herein.

Such detection methods are well known in the art and include ELISA, radioimmunoassay, immunoblot, western blot, immunofluorescence, immunoprecipitation, and other comparable techniques. Proteins comprising at least one follistatin domain may further be provided in a diagnostic kit that incorporates one or more of these techniques to detect GDF-8. Such a kit may contain other components, packaging, instructions, or other material to aid the detection of the protein and use of the kit.

Where proteins comprising at least one follistatin domain are intended for diagnostic purposes, it may be desirable to modify them, for example with a ligand group (such as biotin) or a detectable marker group (such as a fluorescent group, a radioisotope or an enzyme). If desired, the proteins may be labeled using conventional techniques. Suitable labels include fluorophores, chromophores, radioactive atoms, electron-dense reagents, enzymes, and ligands having specific binding partners. Enzymes are typically detected by their activity. For example, horseradish peroxidase is usually detected by its ability to convert 3,3',5,5'-tetramethylbenzidine (TMB) to a blue pigment, quantifiable with a spectrophotometer. Other suitable binding partners include biotin and avidin or streptavidin, IgG and protein A, and the numerous receptor-ligand couples known in the art. Other permutations and possibilities will be readily apparent to those of ordinary skill in the art, and are considered as equivalents within the scope of the instant invention.

Proteins comprising at least one follistatin domain or fragments thereof may also be useful for isolating GDF-8 in a purification process. In one type of process, proteins may be immobilized, for example, through incorporation into a column or resin. The proteins are used to bind GDF-8, and then subject to conditions which result in the release of the bound GDF-8. Such processes may be used for the commercial production of GDF-8.

The following examples provide embodiments of the invention. One of ordinary skill in the art will recognize the numerous modifications and variations that may be performed without altering the spirit or scope of the present invention. Such modifications and variations are believed to be encompassed within the scope of the invention. The examples do not in any way limit the invention. It is understood that all of the numbers in the specification and claims are modified by the term about, as small changes in dosages, for example, would be considered to be within the scope of the invention.

EXAMPLES

Example 1

Purification of JA16-Conjugated Beads

N-hydroxysuccinimidyl-activated beads (4% beaded agarose, Sigma H-8635, St Louis Mo.) were washed in MilliQ-H$_2$O and incubated for 4 hours at 4° C. with the anti-GDF-8 JA16 monoclonal antibody (3–4 µg/µl in 100 mM MOPS, pH 7.5) at a ratio to allow a final concentration of 10 mg JA16/ml resin. Beads were washed extensively with 100 mM MOPS pH 7.5 and phosphate-buffered saline (PBS) (Ausubel et al, (1999) *Current Protocols in Molecular Biology*, John Wiley & Sons) and stored at 4° C. in PBS until use. Control beads were prepared identically without JA16 antibody.

Example 2

Affinity Purification

A total of 40 µl of packed JA16-conjugated or control beads were incubated with 15 ml normal Balb/C mouse serum (Golden West Biologicals, Temecula Calif.) or 30 ml pooled normal human serum (ICN Biomedical, Aurora Ohio) for 3 hours at 4° C. Beads were washed twice in ~10 ml of cold 1% Triton X-100/PBS, twice in ~10 ml of cold 0.1% Triton X-100/PBS, and twice in ~1 ml of cold PBS. Proteins were eluted from the beads in three subsequent steps. First, the beads were treated to a 'mock elution', where 100 µl of PBS was added to the beads and incubated at 4° C. for 30 minutes. The supernatant was collected and combined with 30 µl 4× LDS sample buffer (Invitrogen, Carlsbad Calif.). Second, the beads were subject to a 'peptide elution', 100 µl of 1 µg/µl competing peptide (sequence: DFGLDSDEHSTESRSSRYPLTVDFEAFGWD-COOH (SEQ ID NO:12)) in PBS was added to the beads and again incubated at 4° C. for 30 minutes. The supernatant was collected as before. Third, the beads were treated with an 'SDS elution' technique, where 30 µl of 4×LDS buffer (Invitrogen) and 100 µl of PBS was added to the beads and heated to 80° C. for 10 minutes before transferring the supernatant to a fresh tube.

A silver stained gel of the proteins released in each of the elution steps is shown in FIG. 1. Two protein bands in the silver-stained gel shown in FIG. 1 of approximately 12 and 36 kDa were specifically eluted from JA16-conjugated beads, but not from unconjugated control beads.

Example 3

Mass Spectrometry

Samples were reduced with NuPage 10×reducing agent (Invitrogen) for 10 minutes at 80° C. and alkylated with 110 µM iodoacetamide for 30 minutes at 22° C. in the dark. Samples were run immediately on 10% NuPage Bis-Tris gels in an MES buffer system according to manufacturer's recommendations (Invitrogen) and silver stained using a gluteraldehyde-free system (Shevchenko, et al., (1996) *Anal. Chem.*, 68: 850–858). Bands were excised and digested with Sequencing Grade Modified Trypsin (Promega, Madison Wis.) in an Abimed Digest Pro (Langenfeld, Germany) or ProGest Investigator (Genomics Solutions, Ann Arbor Mich.). The volume of digested samples was reduced by evaporation and supplemented with 1% acetic acid to a final volume of ~20 µl. Samples (5–10 µl) were loaded onto a 10 cm×75 µm inner diameter $C_{18}$ reverse phase column packed in a Picofrit needle (New Objectives, Woburn Mass.). MS/MS data was collected using an LCQ Deca or LCQ Deca XP (Finnigan, San Jose Calif.) mass spectrometer and searched against the NCBI non-redundant database using the Sequest program (Finnigan). Unless otherwise noted, all peptide sequences listed in this paper corresponded to MS/MS spectra that were deemed high quality by manual inspection and produced $X_{corr}$ scores>2.5 in the Sequest scoring system.

Example 4

Western Blots

Proteins were transferred to a 0.45 µm nitrocellulose membrane (Invitrogen) and blocked with blocking buffer (5% non-fat dry milk in Tris-buffered saline (TBS: 10 mM Tris-Cl, pH 7.5, 150 mM NaCl)) at 4° C. overnight. Blots were then probed with primary antibody diluted 1:1000 in blocking buffer for 1–3 hours at room temperature, washed 5×with TBS, probed with horseradish peroxidase-conjugated secondary antibody in blocking buffer for 1–3 hours at room temperature, and washed as before. Signals were detected by autoradiography using the West Pico Substrate (Pierce).

Example 5

Isolation of GDF-8

Figure 2A:
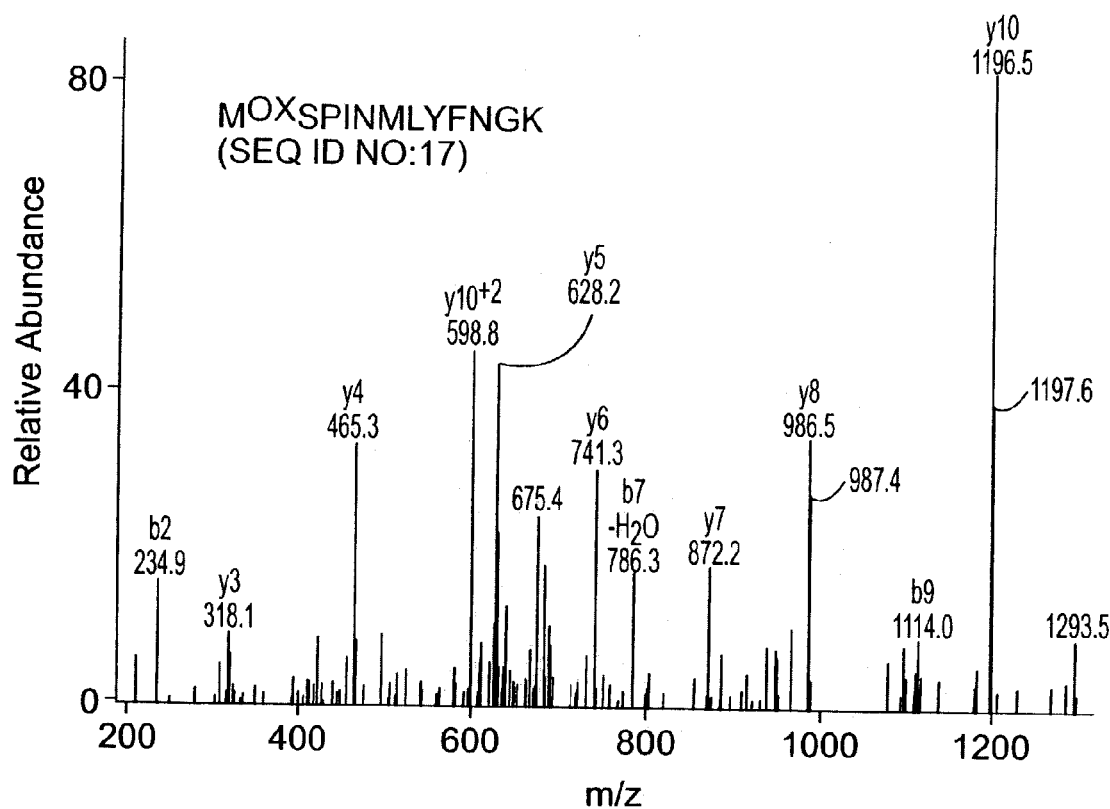
FIG. 2A shows a representative MS/MS spectrum of a GDF-8 derived peptide (SEQ ID NO:19) identified from the 12 kDa band visible in the affinity purified sample. Both N-terminal fragment ions (b ions) and C-terminal fragment ions (y ions) are visible. Notably, the most intense y fragment ions result from fragmentation before the proline residue, a common characteristic of proline containing peptides.

An experiment using the methods described in the previous Examples resulted in the isolation of GDF-8. Since GDF-8 in its reduced form is 12 kDa, we speculated that the protein in the lower band from the silver-stained gel shown in FIG. 1 was mature GDF-8. To confirm this hypothesis, we excised this band, digested it with trypsin, and obtained MS/MS spectra of the resulting peptides by LC-MS/MS. MS/MS spectra corresponding to six tryptic peptides confirmed that mature GDF-8 was isolated from this region of the gel, as shown in FIG. 2A and Table 1.

Table 1 lists peptides derived from GDF-8 (SEQ ID NO:13–20), GDF-8 propeptide (SEQ ID NO:21–27), FLRG (SEQ ID NO:28–30), and GASP1 (SEQ ID NO:31–35) that were found in JA16 immunoprecipitates from mouse and human serum. The immediately preceding amino acid in the protein sequence is shown in parentheses for each peptide and the charge state of the peptide (z) and the Sequest program correlation coefficient ($X_{corr}$, a measure of confidence) are listed. The sequence listing numbers in the table refer only to the isolated peptides and their sequences. The preceding amino acids in parentheses are not included in the peptides, but are provided only for reference. All spectra were confirmed by manual inspection.

Figure 2B:
FIG. 2B shows a western blot probed with a polyclonal antibody that recognizes the mature region of GDF-8, confirming the presence of GDF-8 in the affinity purified samples. Both the mature and unprocessed forms of GDF-8 are visible.

Interestingly, the western blot also contained a band corresponding to unprocessed full-length GDF-8 (43 kDa), implying that some portion of this molecule is secreted into serum without undergoing proteolytic processing (FIG. 2B). The presence of unprocessed GDF-8 was confirmed my mass spectrometry (data not shown). Thus, the affinity purification method effectively isolated GDF-8 from normal mouse serum.

Although the JA16 antibody recognizes both GDF-8 and the highly related protein BMP/GDF-11, we saw no evidence of BMP-11 peptides in our affinity purified samples by mass spectrometry.

TABLE 1

Peptides Identified in JA16 Immunoprecipitates

| | | z | $X_{corr}$ |
|---|---|---|---|
| mouse serum | | | |
| GDF-8 (mature) | (K) ANYCSGECEFVFLQK (SEQ ID NO:13) | 3+ | 4.63 |
| | (K) MSPINMLYFNGK (SEQ ID NO:14) | 2+ | 3.81 |
| | (R) DFGLDCDEHSTESR (SEQ ID NO:15) | 2+ | 3.47 |
| | (K) ANYCSGECEFVFLQK (SEQ ID NO:16) | 2+ | 3.31 |
| | (K) M*SPINMLYFNGK (SEQ ID NO:17) | 3+ | 2.95 |
| | (R) YPLTVDFEAFGWDWIIAPK (SEQ ID NO:18) | 2+ | 2.86 |
| | (K) M*SPINM*LYFNGK (SEQ ID NO:19) | 2+ | 2.51 |
| | (R) GSAGPCCTPTK (SEQ ID NO:20) | 2+ | 2.43 |
| GDF-8 (pro-peptide) | (K) LDM*SPGTGIWQSIDVK (SEQ ID NO:21) | 2+ | 3.82 |
| | (K) ALDENGHDLAVTFPGPGEDGLNPFLEVK (SEQ ID NO: 22) | 3+ | 3.17 |
| | (K) LDMSPGTGIWQSIDVK (SEQ ID NO:23) | 2+ | 2.98 |
| | (R) ELIDQYDVQR (SEQ ID NO:24) | 2+ | 2.97 |
| | (K) TPTTVFVQILR (SEQ ID NO:25) | 2+ | 2.91 |
| | (K) AQLWIYLRPVK (SEQ ID NO:26) | 2+ | 2.77 |
| | (K) EGLCNACAWR (SEQ ID NO:27) | 2+ | 2.75 |
| follistatin-like related gene (FLRG) | (R) PQSCLVDQTGSAHCVVCR (SEQ ID NO:28) | 3+ | 3.34 |
| | (K) DSCDGVECGPGK (SEQ ID NO:29) | 2+ | 2.99 |
| | (K) SCAQVVCPR (SEQ ID NO:30) | 2+ | 2.59 |
| novel multi-domain protease inhibitor (GASP1) | (R) ECETDQECETYEK (SEQ ID NO:31) | 2+ | 2.98 |
| | (R) ADFPLSVVR (SEQ ID NO:32) | 2+ | 2.56 |
| | (R) EACEESCPFPR (SEQ ID NO:33) | 2+ | 2.95 |
| | (R) SDFVILGR (SEQ ID NO:34) | 2+ | 2.73 |
| | (R) VSELTEEQDSGR (SEQ ID NO:35) | 2+ | 3.88 |
| human serum | | | |
| GDF-8 mature | (K) ANYCSGECEFVFLQK (SEQ ID NO:36) | 2+ | 4.21 |
| | (R) DFGLDCDEHSTESR (SEQ ID NO:37) | 3+ | 2.08 |
| GDF-8 (pro-peptide) | (K) ALDENGHDLAVTFPGPGEDGLNPFLEVK (SEQ ID NO:38) | 3+ | 3.71 |
| | (R) ELIDQYDVQR (SEQ ID NO:39) | 2+ | 3.01 |
| follistatin-like related gene (FLRG) | (R) PQSCVVDQTGSAHCVVCR (SEQ ID NO:40) | 3+ | 3.37 |
| | (R) CECAPDCSGLPAR (SEQ ID NO:41) | 2+ | 3.21 |
| | (R) LQVCGSDGATYR (SEQ ID NO:42) | 2+ | 3.06 |
| multi-domain protease inhibitor (GASP1) | (R) VSELTEEPDSGR (SEQ ID NO:43) | 2+ | 2.44 |
| | (R) CYMDAEACSK (SEQ ID NO:44) | 2+ | 2.69 |
| | (K) GITLAVVTCR (SEQ ID NO:45) | 2+ | 2.42 |

M* = oxidized methionine

Example 6

Isolation of Proteins Bound to GDF-8

Figure 3A:
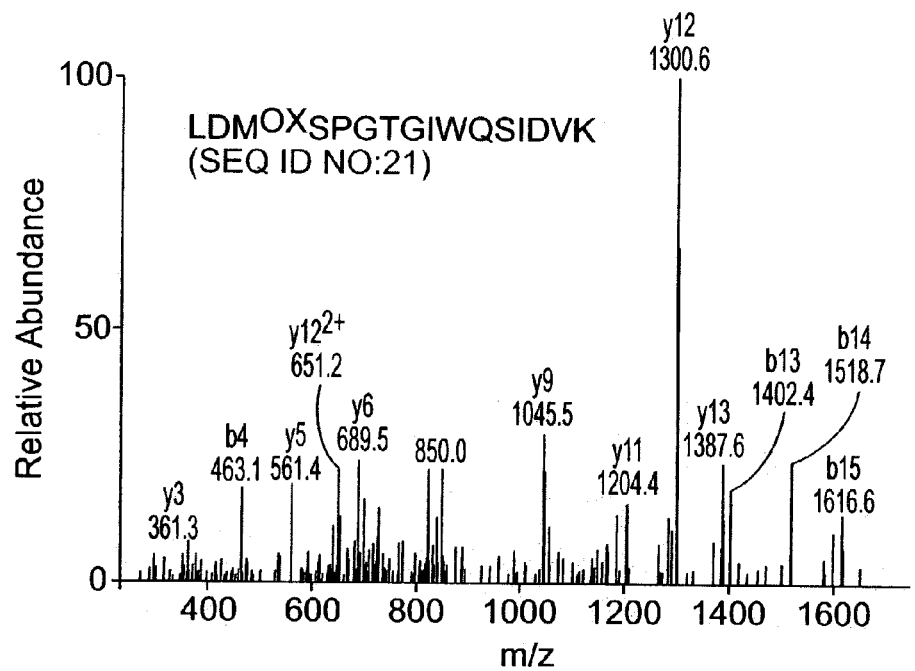
FIG. 3 shows the GDF-8 propeptide and follistatin-like related gene (FLRG) bind to circulating GDF-8 isolated from normal mouse serum. Representative MS/MS spectra from GDF-8 propeptide (SEQ ID NO:23) (FIG. 3A) and FLRG (SEQ ID NO:30) (FIG. 3C) derived peptides identified in the 36 kDa band are shown.
FIG. 3B shows a western blot of affinity purified GDF-8 complex probed with a polyclonal antibody that specifically recognizes the propeptide region of GDF-8, confirming the mass spectrometric identification of this protein in the GDF-8 complex. Both the clipped propeptide and unprocessed GDF-8 are visible—at longer exposures, unprocessed can also be seen in the SDS eluted sample.
FIG. 3D shows a western blot of affinity purified GDF-8 complex probed with a monoclonal antibody to FLRG.
Figure 3B:
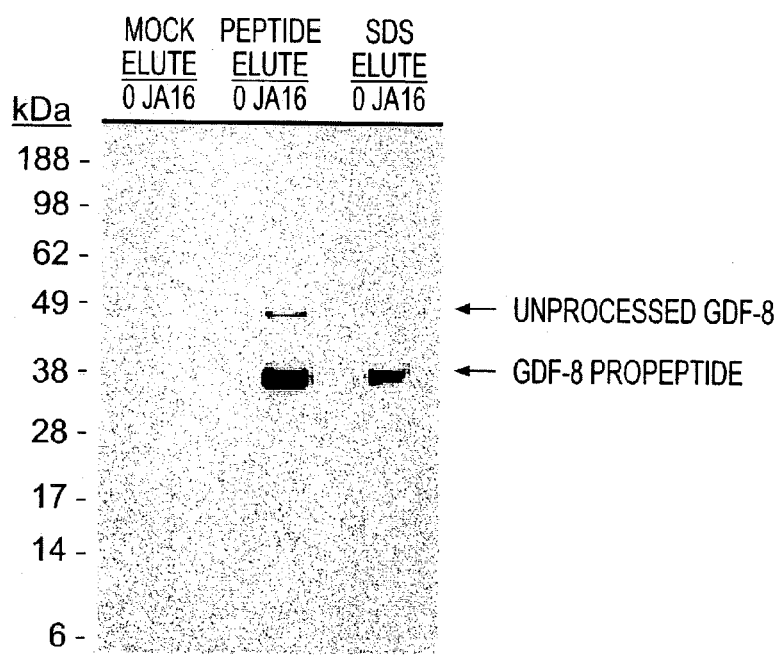
Figure 3C:
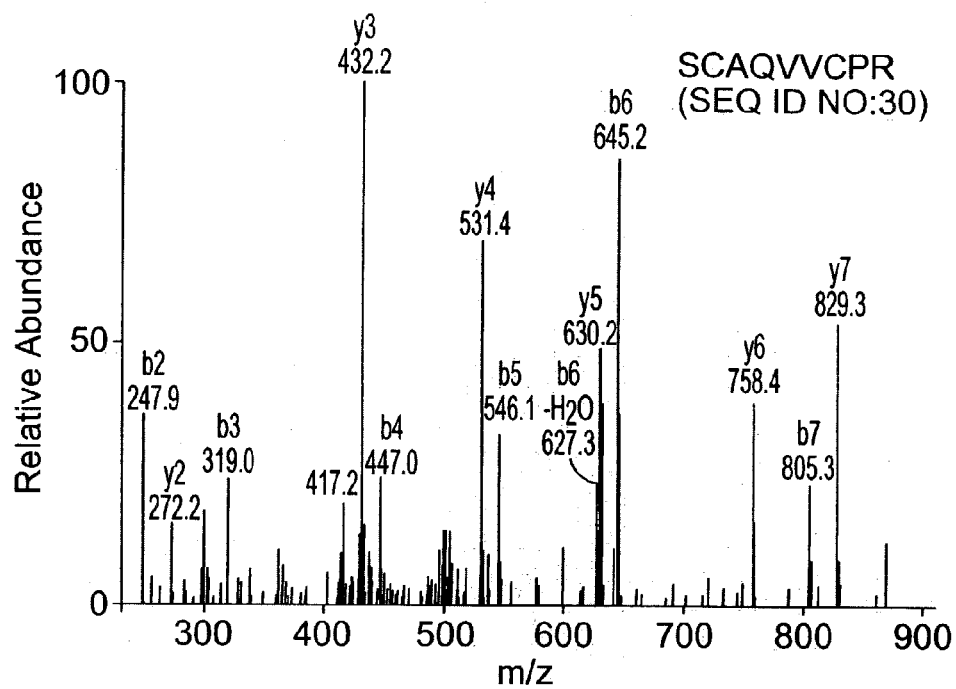
Figure 3D:
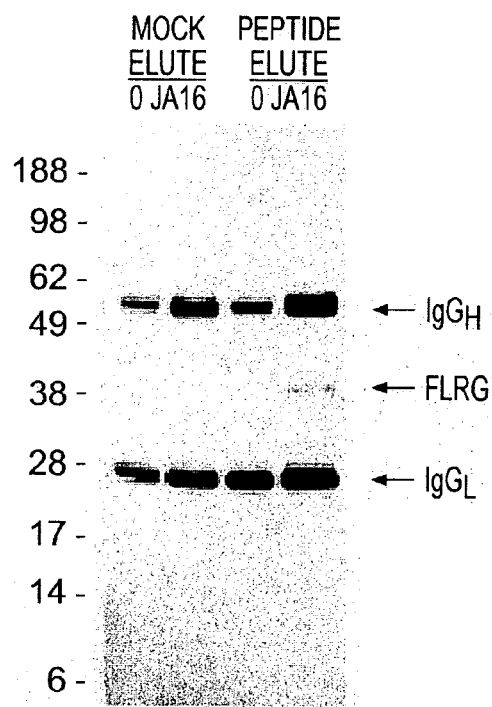

Once it was confirmed that the affinity purification technique could successfully isolate GDF-8 from normal mouse serum, we proceeded to identify proteins that bind to GDF-8 under native conditions. The 36 kDa band on the silver-stained gel shown in FIG. 1 was analyzed as described above. Mass spectrometry identified two proteins in this region of the gel that were specific to the JA16-immunopurified sample. These were determined to be the GDF-8 propeptide and follistatin-like related gene (FLRG). The peptides identified from each of these proteins are shown in Table 1 (SEQ ID NO:13–27). High quality MS/MS spectra were found for six unique peptides from GDF-8 propeptide and three unique peptides from FLRG; representative peptides are shown in FIGS. 3A and 3C. Furthermore, the presence of both of these proteins was confirmed by western blotting with polyclonal antibodies specific to GDF-8 propeptide and FLRG respectively (FIGS. 3B and 3D). Thus, circulating GDF-8 appears to bind to the GDF-8 propeptide and to FLRG in vivo.

Example 7

Isolation of Novel Proteins that Bind GDF-8

Figure 4:
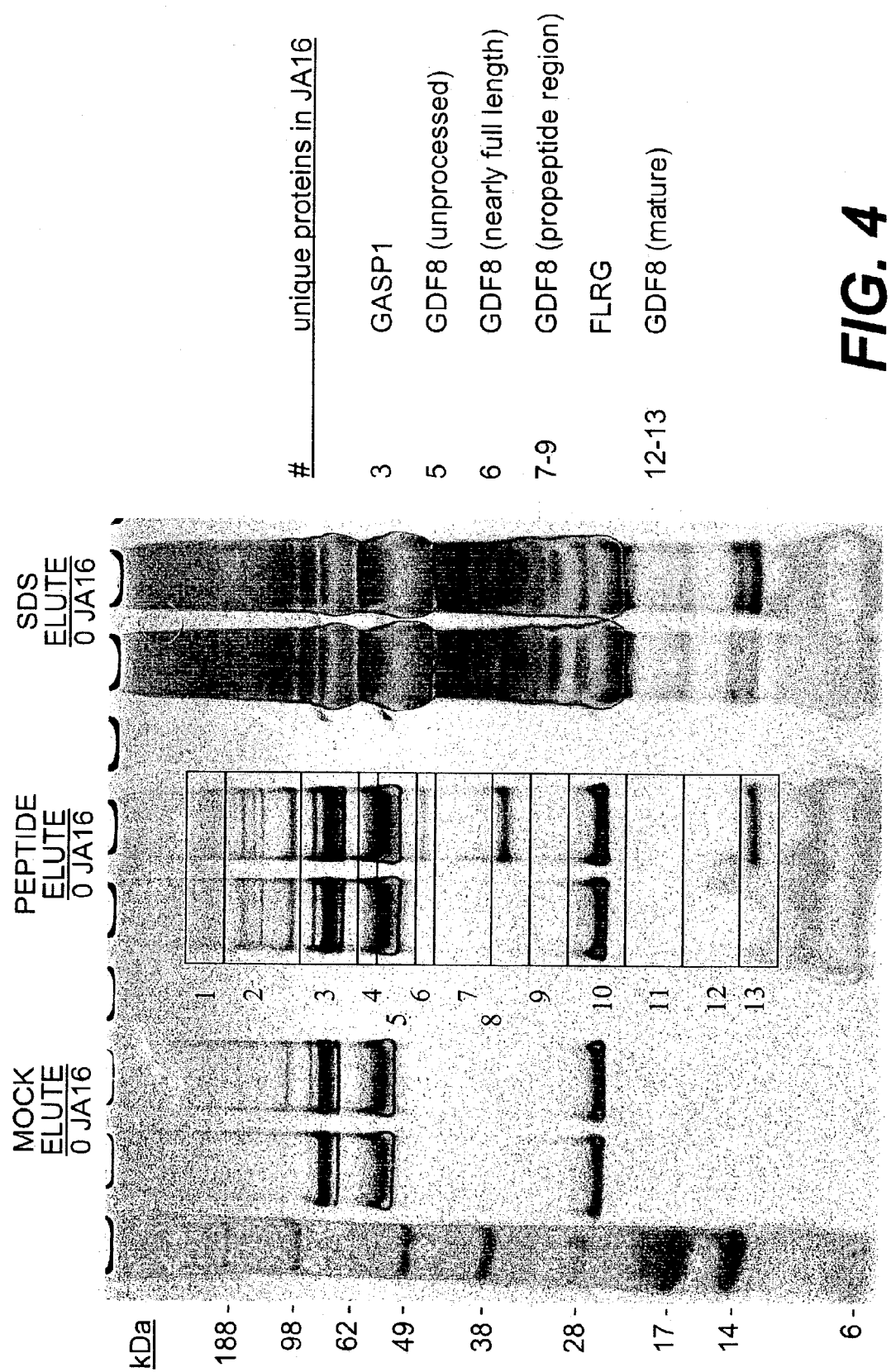
FIG. 4 shows results from a thorough analysis of a large scale GDF-8 purification that identified GDF-8 propeptide, FLRG, and a novel protein as the major GDF-8 binding proteins in serum. A silver stained gel was dissected into 13 slices from the peptide eluted sample of both negative control and JA16 immunoprecipitates. The proteins in each slice were digested with trypsin and identified using nano-flow-LC-MS/MS and database searching. Proteins unique to the JA16 sample included only unprocessed and mature GDF-8, GDF-8 propeptide, FLRG, and a novel multidomain protease inhibitor (GDF-associated serum protein 1, GASP1). These proteins were identified from the noted regions of the gel.

To characterize the major components of the circulating GDF-8 complex in vivo, native GDF-8 and its associated proteins from wild-type mouse serum were isolated by affinity purification with an agarose-conjugated anti-GDF-8 monoclonal antibody, JA16. JA16-bound proteins were subjected to subsequent elution steps with PBS buffer alone (mock elution), a peptide that could compete with GDF-8 for JA16 binding, and SDS detergent. These samples were concentrated, run on a one-dimensional SDS-PAGE gel, and visualized by silver stain (FIG. 4). Two bands unique to the JA16 purified samples are visible—a 12 kDa band identified as GDF-8, and a 36 kDa band containing both GDF-8 propeptide and FLRG.

In order to determine if one could identify other proteins that were bound to GDF-8 in vivo, we scaled up the purification approximately five-fold and used mass spectrometry to search for proteins that were present in the JA16 immunocomplex, but not in the negative control. To achieve this goal, we excised regions of the silver stained gel corresponding to molecular weights between 10 and 200 kDa into 13 gel slices, as shown in FIG. 4. Each of these slices was subjected to in-gel trypsin digestion and LC-MS/MS. Comparison of the resulting MS/MS spectra to the non-redundant NCBI database of known proteins did not reveal any additional proteins specific to the JA16 immunoprecipitate, although the proteins previously described (mature GDF-8, GDF-8 propeptide, unprocessed GDF-8, and FLRG) were all identified in these samples (FIG. 4). Background proteins that were found both in the JA16 immunocomplex and in the negative control sample included abundant serum proteins, such as albumin, immunoglobulins, and complement proteins. There was no evidence of other TGF-β superfamily members, including the highly related protein BMP-11/GDF-11, in the JA16 samples. Thus, the JA16 antibody specifically purified GDF-8 in these experiments.

Interestingly, we found no evidence of follistatin in our GDF-8 immunocomplexes, despite the fact that JA16 is capable of immunoprecipitating a GDF-8/follistatin complex in vitro (data not shown). Follistatin has been shown to inhibit GDF-8 activity by antagonizing the association of GDF-8 with the ActRIIB receptor (Lee and McPherron (2001) *Proc. Natl. Acad. Sci. U.S.A.*, 98: 9306–9311). Our results suggest that follistatin does not play a major role in the regulation of the activity of the circulating GDF-8 complex under normal conditions.

Since the identification of proteins by this MS/MS procedure is dependent on the content of the database being searched, we further analyzed the data from FIG. 4 by comparing the MS/MS spectra collected from the 13 samples to a database of proteins predicted from the Celera mouse genomic sequence. This analysis identified an additional protein specific to the JA16-purified sample, and is hereby referred to as GDF-associated serum protein 1 (GASP1). Since the initial identification of this protein, this sequence has been added to the NCBI nr database by the public genome sequencing effort under the accession number gi|20914039.

Figure 5A:
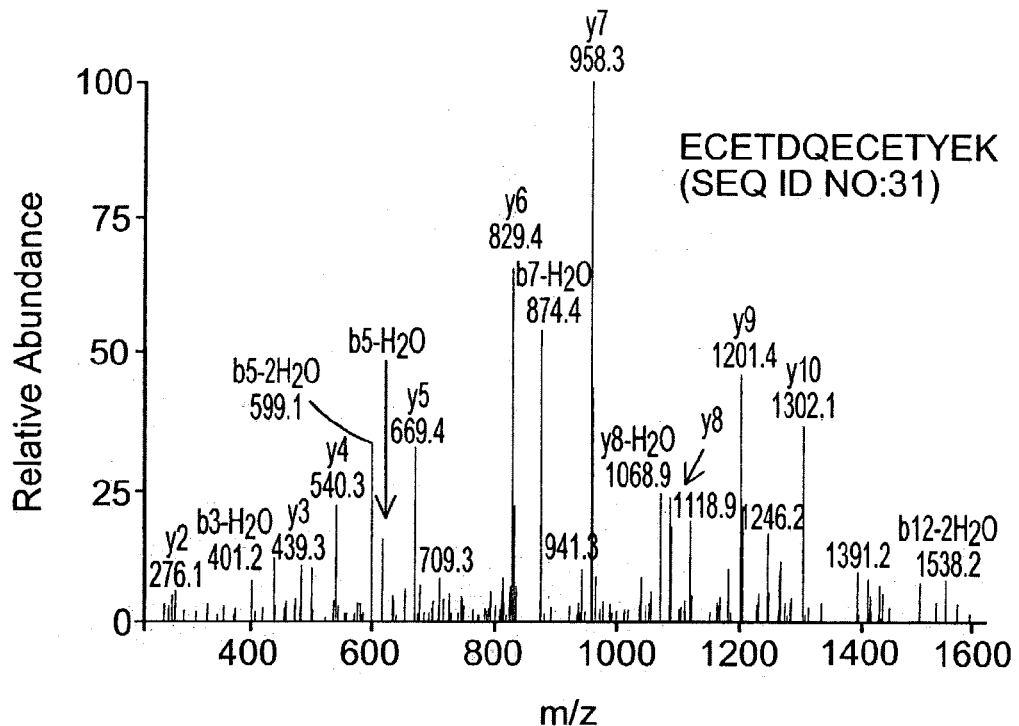
FIGS. 5A (peptide assigned SEQ ID NO:31) and 5B (peptide assigned SEQ ID NO:33) show representative MS/MS spectra from two GASP1 peptides, identified in band 3 of the silver stained gel of FIG. 4.
Figure 5B:
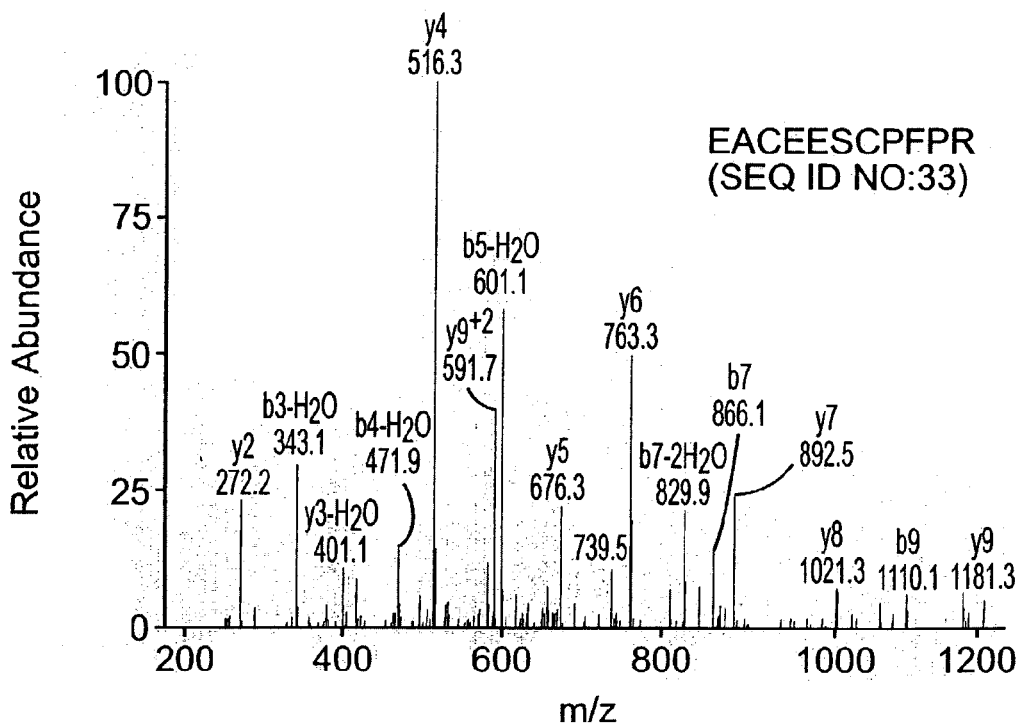
FIG. 5 shows that a novel multidomain protease inhibitor, GASP1, is bound to GDF-8 in serum.

Five peptides corresponding to the sequence of GASP1 were identified on the basis of high-quality MS/MS spectra (Table 1 (SEQ ID NO:31–35); FIGS. 5A and B). The spectra corresponding to GASP1 peptides were found in band 3, which contains 70–80 kDa proteins. However, a specific band corresponding to this protein was not visible, probably due to the abundance of background immunoglobulins and albumin at this area (see FIG. 4). Sequest $X_{corr}$ scores above 2.3 are generally considered significant for 2+ions. Fortuitously, one of the peptides identified in our experiments (sequence=ECETDQECETYEK (SEQ ID NO:31)) spans the junction between the two exons that code for this protein, verifying the accuracy of Celera's gene prediction algorithm in this instance.

Figures 14A, 14B:
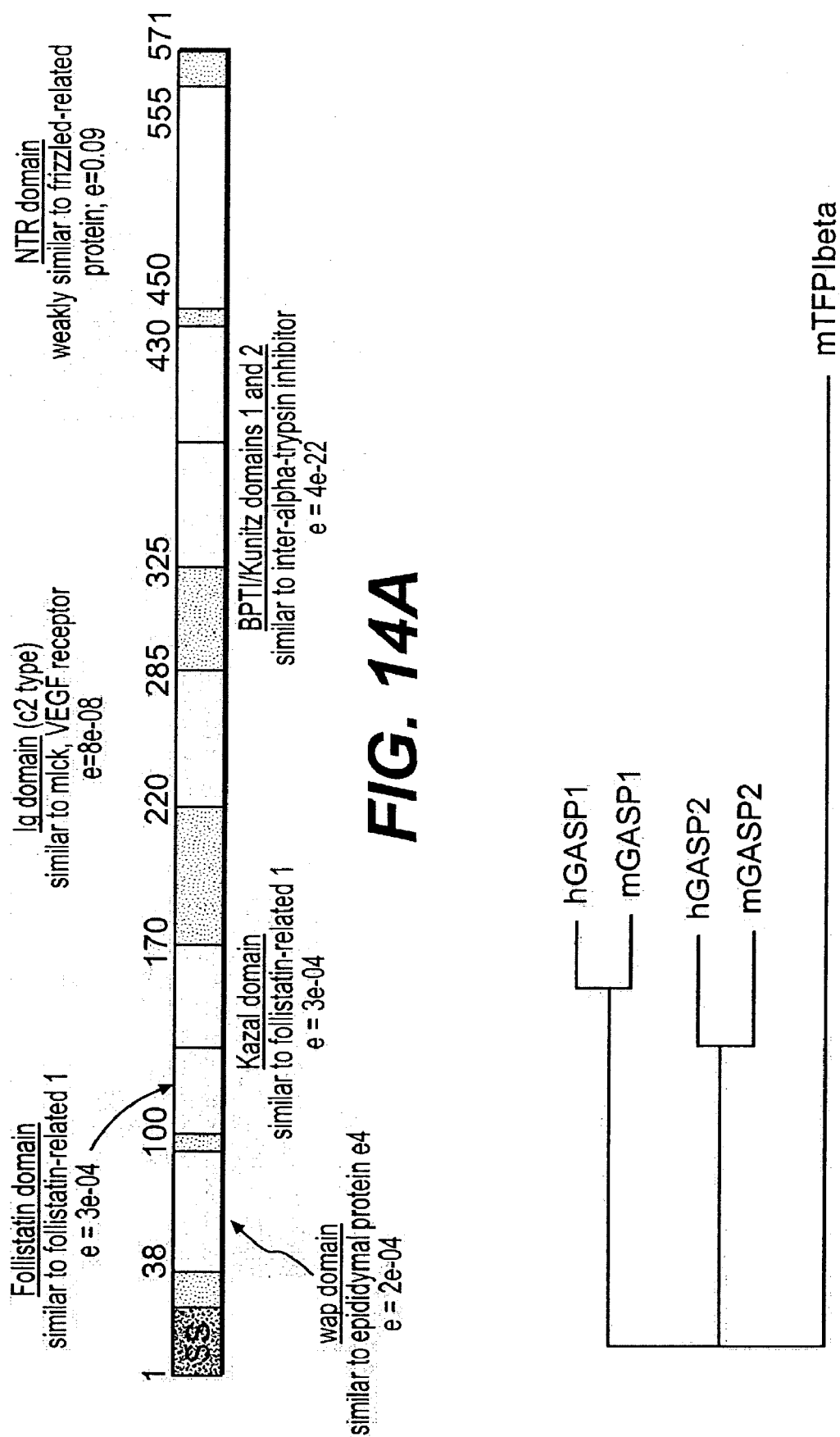
FIG. 14A shows the domain structure of GASP1. GASP1 has a signal sequence/cleavage site after amino acid 29. In addition, GASP1 contains two Kunitz/BPTI serine protease inhibitor domains, a follistatin domain (including a Kazal serine protease inhibitor motif) and a netrin domain, which may inhibit metalloproteases.
FIG. 14B shows the phylogenetic tree of GASP1 and GASP2 predicted from the mouse and human genomic sequences. Mouse and human GASP1 are 90% identical. GASP1 and GASP2 are 54% identical.

The sequences of the GASP1 transcript and protein were predicted prior to the actual cloning of GASP1 (FIG. 6). GASP1 was predicted to be a 571 amino acid protein with a predicted molecular mass of 63 kDa. It has a putative signal sequence/cleavage site at its N-terminus and two possible sites for N-glycosylation at amino acids 314 and 514. Analysis of the GASP1 protein sequence by Pfam and BLAST (according to the techniques in Altschul et al.(1990) *J. Mol. Biol.*, 215: 403–410; Bateman et al. (2002) *Nucleic Acids Res.*, 30: 276–280) revealed that GASP1 contains many conserved domains, including a WAP domain, a follistatin/Kazal domain, an immunoglobulin domain, two tandem Kunitz domains, and a netrin domain (FIG. 14A). WAP domains, originally identified in whey acidic protein, contain 8 cysteines that form a four-disulfide core and are often found in proteins with anti-protease activity (Hennighausen and Sippel (1982) *Nucleic Acids Res.*, 10: 2677–2684; Seemuller et al. (1986) *FEBS Lett.*, 199: 43–48). It is believed that the follistatin domain mediates the interaction between GDF-8 and GASP1. The C-terminal region of follistatin domains contains a similarity to Kazal serine protease inhibitor domains. In the case of GASP1, this region is even more closely related to Kazal domains than in follistatin or FLRG, suggesting the possibility that this region may have an additional protease inhibitor function. Kunitz domains, originally identified in bovine pancreatic trypsin inhibitor, also inhibit serine proteases, thus establishing a likely role for GASP1 in the regulation of this class of proteins. Furthermore, netrin domains have been implicated in the inhibition of metalloproteases (Banyai and Pafthy, 1999; Mott et al., 2000). Thus, based on the presence of these conserved regions, GASP1 is likely to inhibit the activity of proteases, perhaps regulating GDF-8 processing or activation of the latent GDF-8 complex.

BLAST searches against the mouse Celera transcript database revealed a protein that has >50% identity with GASP1, referred to here as GASP2. GASP2 contains the same domain structure as GASP1, suggesting that these proteins define a two member family of multivalent protease inhibitors (FIG. 14B). Interestingly, only peptides corresponding to GASP1, not GASP2, were found in our JA16 purified samples. This result suggests that GASP1 and GASP2 likely have different biological specificity. Both GASP1 and GASP2 are conserved in humans (>90% identity with mouse). The sequence for human GASP1 is now available in the NCBI nr database under the accession number gi|18652308. Although, the concentration of GDF-8 in human serum is considerably lower than that found in mouse serum (Hill et al. (2002) *J. Biol. Chem.*, 277: 40735–40741), the sensitivity of mass spectrometric analysis of proteins allowed us to identify 3 peptides corresponding to the human homolog of GASP1 from JA16 immunoprecipitations from human serum (Table 1). None of these peptides were found in the corresponding negative control. Again, there was no evidence of human GASP2 in these experiments. Thus, the interaction between GASP1 and GDF-8 is conserved between mouse and human.

Figure 10:
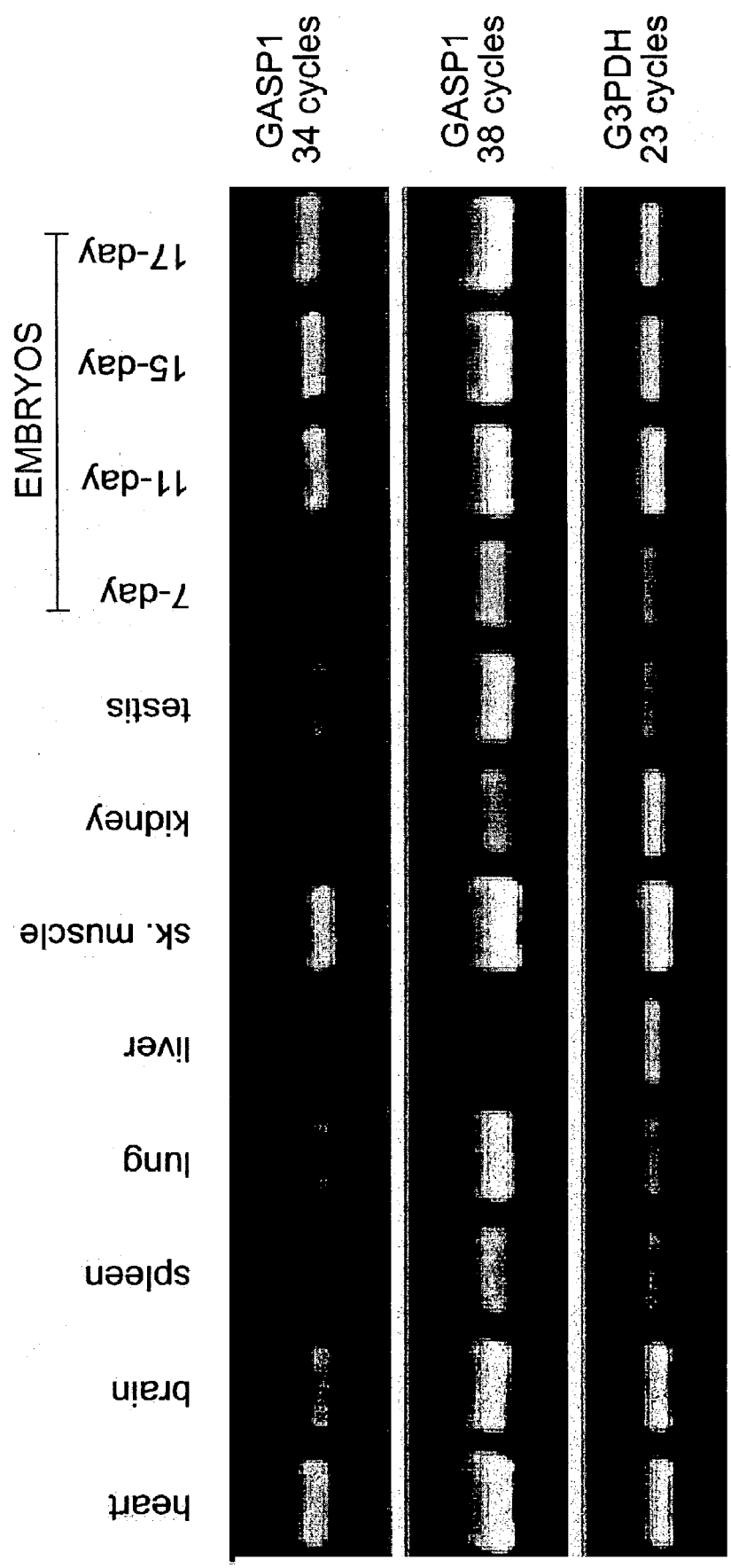
FIG. 10 shows that mouse GASP1 is expressed in many adult tissues and during development. The figure shows tissue expression profiles of mouse GASP1. A 551 bp fragment of GASP1 was amplified from normalized first-strand cDNA panels from Clontech (Palo Alto, Calif.). A portion of glyceraldehyde-3-phosphate dehydrogenase (G3PDH) was amplified as a control. G3PDH expression is known to be high in skeletal muscle and low in testis. The cDNA panels were normalized against β-actin, phospholipase A2, and ribosomal protein S29, in addition to G3PDH.

GDF-8 is produced nearly exclusively in skeletal muscle. In order to determine the tissue distribution of GASP1 mRNA, a 551 bp fragment of GASP1 was amplified from first-strand cDNA produced from a variety of mouse tissues and staged embryos (FIG. 10). A mouse GASP1 fragment was amplified from normalized mouse first-strand cDNA panels (Clontech, Palo Alto Calif.) using the Advantage cDNA PCR kit (Clontech) according to the manufacturer's recommendations (forward primer: 5' TTGGCCACTGC-CACCACMTCTCMCCACTT 3' (SEQ ID NO:46); reverse primer: 5' TCTCAGCATGGCCATGCCGCCGTCGA 3' (SEQ ID NO:47)). GASP1 appears to be fairly widely-expressed, with particularly high expression in skeletal muscle and heart. Significant expression is also seen in brain, lung, and testis. In contrast, liver and kidney express relatively low levels of GASP1 mRNA. Developmentally, the level of GASP1 mRNA remains fairly constant, perhaps increasing slightly between day 7 and day 11 of mouse embryogenesis.

Example 8

GDF-8 in Human and Mouse Serum

Figures 11A, 11B:
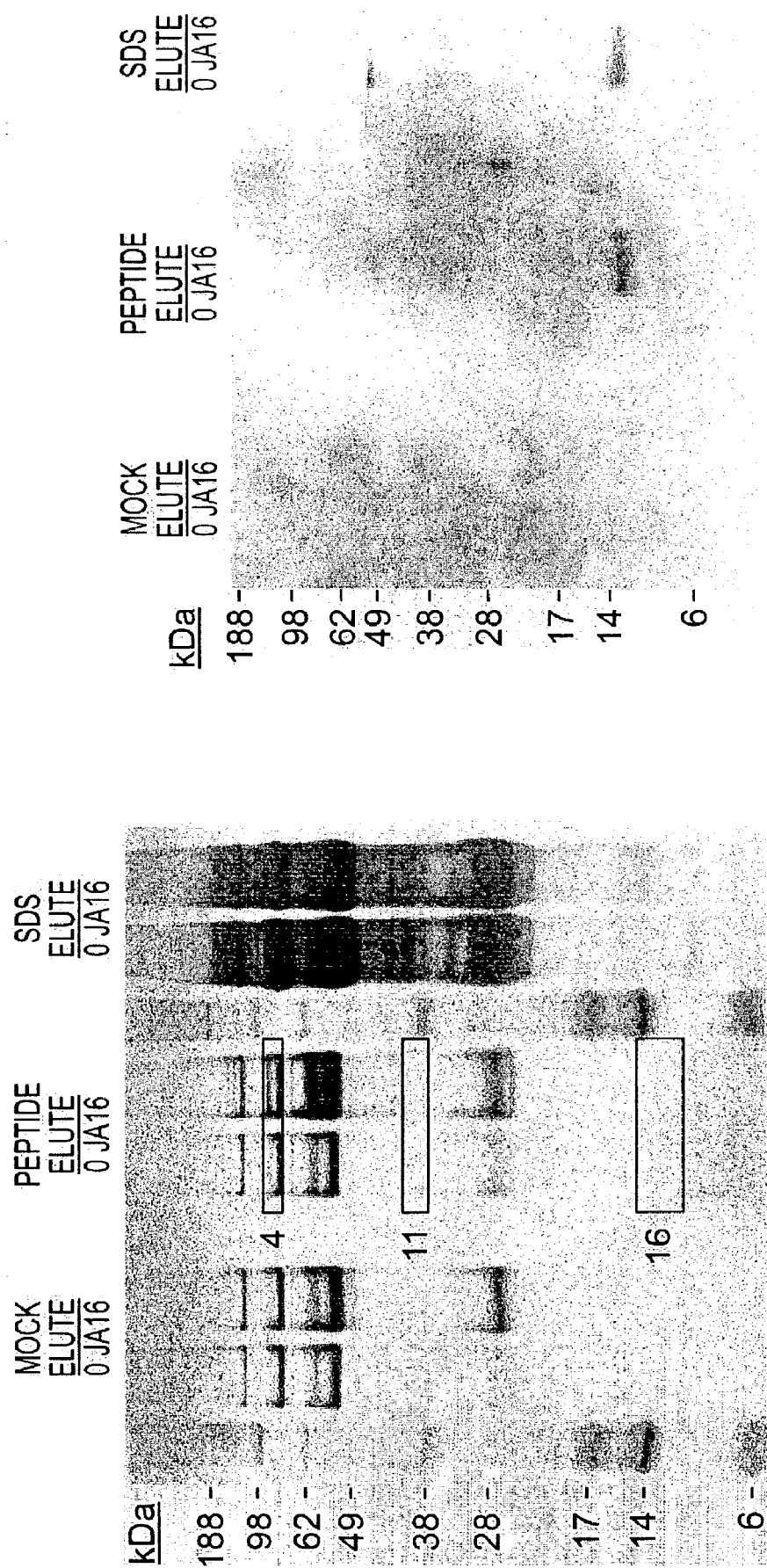
FIG. 11B shows a western blot of an identical JA16 immunoprecipitate probed with an antibody that recognizes mature GDF-8. Bands corresponding to mature and unprocessed GDF-8 isolated from human serum are visible.
Figure 12A:
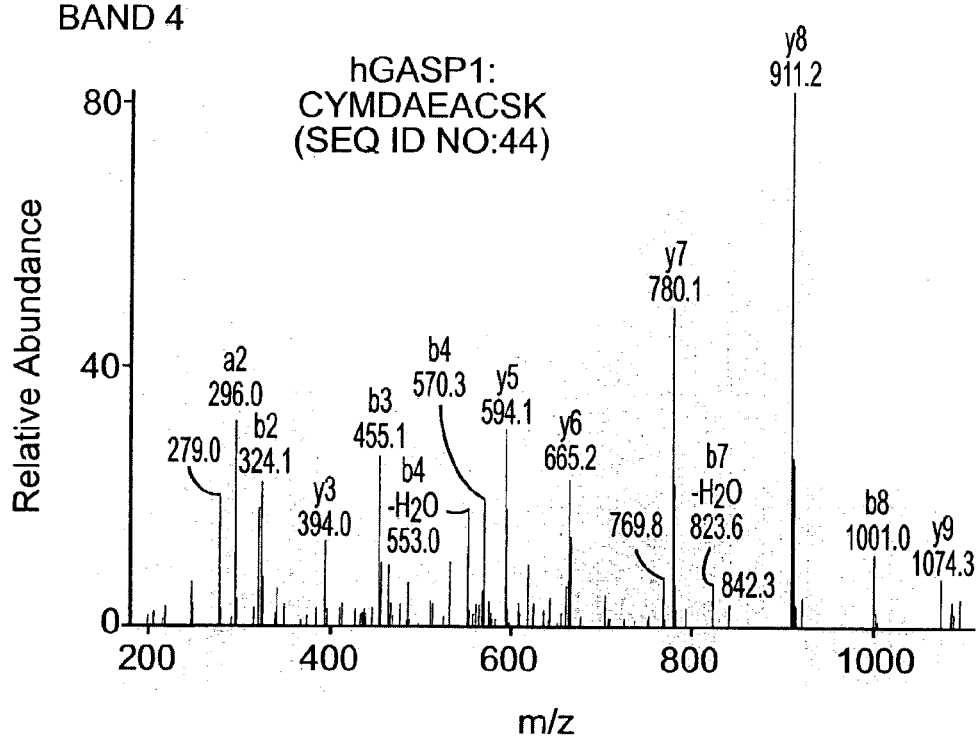
FIG. 12 shows representative mass spectra of a peptide derived from GDF-8 and associated proteins isolated from bands 4, 11, and 16 (FIG. 11). The peptide sequence and N-terminal (b ions) and C-terminal (y ions) are shown. A complete listing of identified peptides is provided in Table 1. Spectra are shown from a GASP1 peptide (SEQ ID NO:44) (FIG. 12A), a FLRG peptide (SEQ ID NO:41) (FIG. 12B), a GDF-8 propeptide peptide (SEQ ID NO:24) (FIG. 12C), and a mature GDF-8 peptide (SEQ ID NO:13) (FIG. 12D).
Figure 12B:
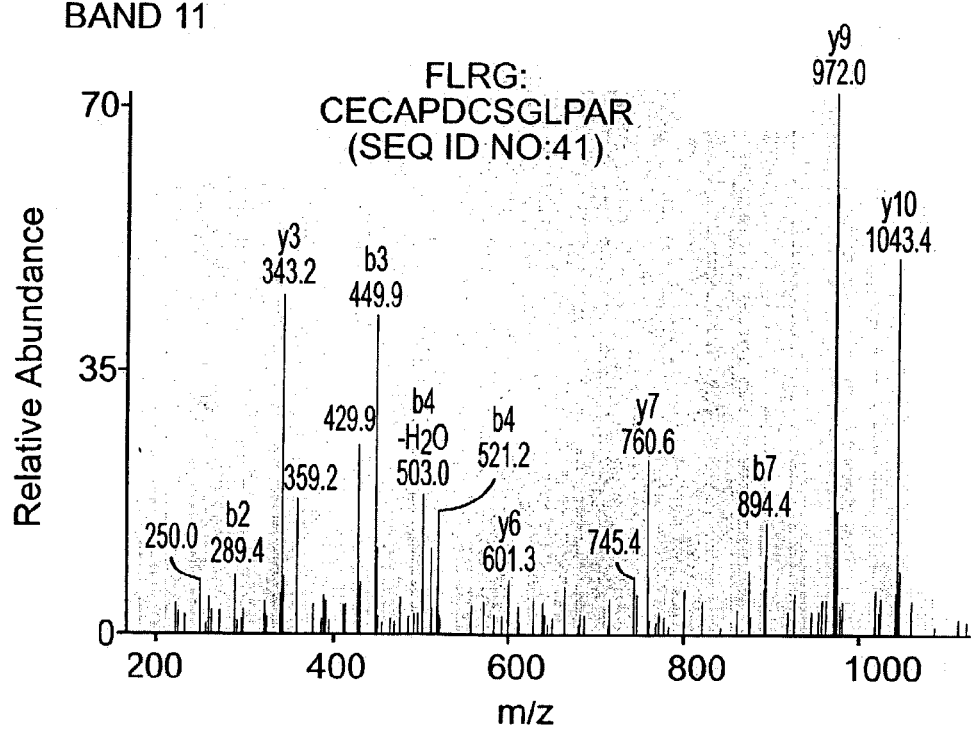
Figure 12C:
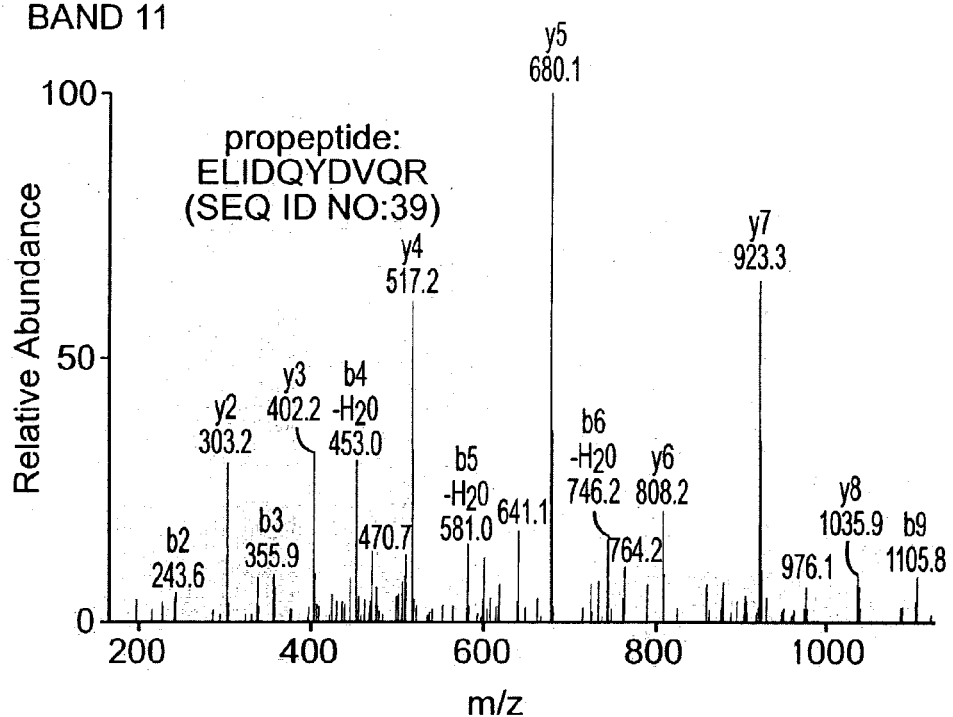
Figure 12D:
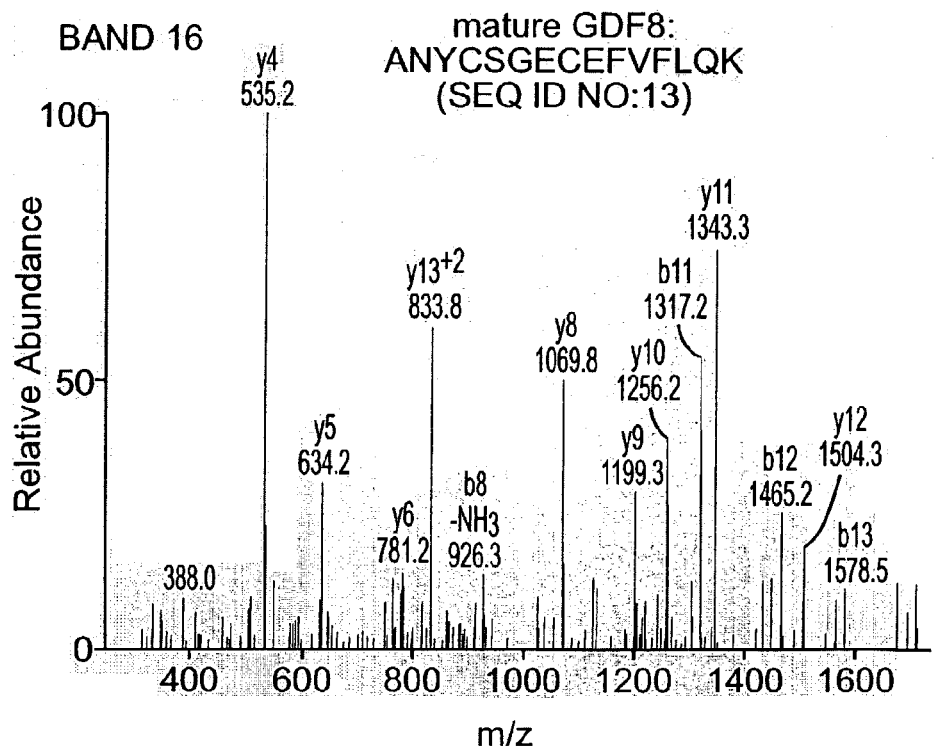

The concentration of GDF-8 in human serum is considerably lower than that found in mouse serum. Since GDF-8 has potential as a therapeutic target, it was a goal to determine the composition of the circulating GDF-8 complex in humans. This knowledge would determine the validity of the mouse model and potentially identify alternative therapeutic targets. Thus, the JA16-based affinity purification of GDF-8 was repeated using human serum. Due to the lower level of GDF-8 in human serum compared with mouse, no bands corresponding to mature GDF-8 and GDF-8 propeptide/FLRG were visualized (FIG. 11A). However, western blotting with a polyclonal antibody that recognizes the mature region of GDF-8 revealed the presence of mature and unprocessed GDF-8 in the JA16-purified samples (FIG. 11B).

We took advantage of the high sensitivity of mass spectrometry to identify proteins that co-purified with mature GDF8. The lanes corresponding to peptide eluted samples from both negative control and JA16-conjugated beads were sliced into 16 pieces. These gel slices were subjected to in-gel trypsin digestion, nanoflow LC-MS/MS, and analysis with Sequest as before.

Interestingly, the only proteins that were identified specifically in the JA16 samples and not the negative control were mature GDF-8, GDF-8 propeptide, human FLRG, and the human homolog of GASP1. The peptides found from each of these proteins are listed in Table 1 (SEQ ID NO:36–45) and representative MS/MS spectra are shown in FIG. 12. Thus the in vivo GDF-8 complex appears to be conserved between mouse and human.

Example 9

Cloning and Characterization of Mouse GASP1

After identifying the predicted GASP1 sequence, it was a goal to determine the actual sequence of mouse GASP1. Based on the Celera predicted sequence, the GASP1 coding sequence was amplified from mouse heart QUICKCLONE cDNA (Clontech) by PCR with PfuTurbo polymerase (Stratagene) using the following primers (fp: 5' CACCATGTGT-GCCCCAGGGTATCATCGGTTCTGG 3' (SEQ ID NO:50);

rp: 5' TTGCMGCCCAGGMGTCCTTGAGGAC 3' (SEQ ID NO:51)). The PCR product from this reaction ran as a single major band of approximately 1700 base pairs on a 1% agarose gel. The amplified DNA was then cloned into the TOPO sites of the pcDNA3.1 DN5-His-TOPO vector (Invitrogen) so as to include an in-frame C-terminal V5-His tag according to manufacturers' recommendations. The full-length cDNA insert was sequenced on both strands. The nucleotide sequence of the mouse GASP1 clone is shown in FIG. 13. This clone matched the predicted Celera sequence, with the exception of some base substitutions in wobble codons that did not change the predicted amino acid sequence (i.e., 288C:G; 294G:A; 615G:A; 738A:G; 768C:T; 1407A:G; 1419A:G; and 1584C:G, where the first base at the indicated position is that reported by Celera and the second base is that obtained from sequencing of the clone; see FIGS. 6A and B).

To determine the N-terminal processing of the GASP1 protein, we transfected COS1 cells with a mammalian expression vector encoding mouse GASP1 cloned with a C-terminal V5-His tag (GASP1-V5-His). Serum-free conditioned media was harvested 48 hours later and analyzed by western blot analysis with an anti-V5 polyclonal antibody (Sigma). More specifically, conditioned media was collected 48 hours after transfection of COS1 cells with GASP1-V5-His/pcDNA3.1 D-V5-His-TOPO or empty vector using the FuGENE 6 reagent (Roche) in serum-free Dulbecco's modified Eagle's medium.

A single band, running at approximately 80 kDa was seen, confirming that GASP1 is secreted into the conditioned media (data not shown). Approximately 10 ml of this conditioned media was run over a His-affinity column and further purified by reverse phase chromatography. This purification scheme yielded a band the expected size of full-length GASP1 on a Coomassie stained SDS-PAGE gel. Edman sequencing of this band determined an N-terminal sequence of L-P-P-I-R-Y-S-H-A-G-I (SEQ ID NO:52). Thus, amino acids 1–29 of GASP1 constitute the signal sequence that is removed during processing and secretion.

Example 10

Binding of Recombinantly-Produced GASP1 to GDF-8 Propeptide and Mature GDF-8

Next, it was determined that recombinantly-produced GASP1 had the same binding pattern to GDF-8 as GASP1 isolated from mouse serum. For immunoprecipitations with recombinant proteins, 400 µl conditioned media from vector- or GASP1-transfected cells was combined with 1.2 µg of recombinant purified GDF-8 and/or GDF-8 propeptide protein (Thies et al., 2001). JA16 (10 µl packed volume) or anti-V5 (30 µl) conjugated agarose beads were incubated with the supplemented conditioned media for two hours at 4° C. and washed twice in cold 1% Triton in phosphate-buffered saline (PBS) and twice in PBS. Beads were resuspended in 50 µl 1×LDS buffer with DTT. Western blots were performed as previously described (Hill et al., 2002).

Figures 15A, 15B:
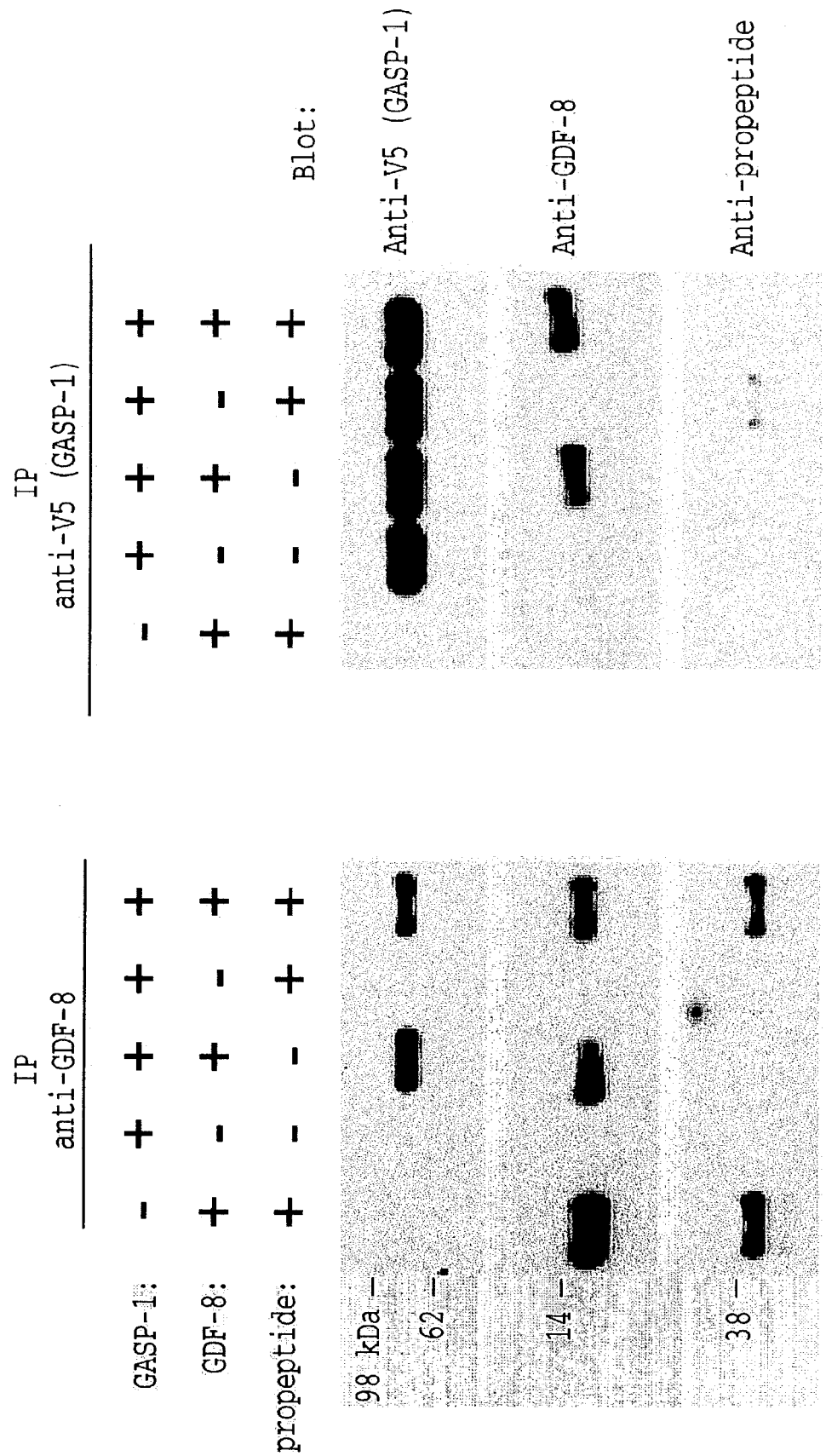
FIG. 15 shows that recombinantly-produced GASP1 binds separately to both GDF-8 and GDF-8 propeptide. (A) JA16 was used to immunoprecipitate GDF-8 from mock- or GASP1-V5-His transfected COS cell conditioned media supplemented with recombinant purified GDF-8 and/or propeptide. Western blots with anti-V5 (top panel), anti-GDF-8 (middle panel), or anti-propeptide polyclonal antibodies were used to determine whether these proteins were present in the immunoprecipitate. (B) Recombinantly-produced GASP1 protein was immunoprecipitated by anti-V5 tag antibodies from mock- or GASP1-V5-His conditioned media supplemented with recombinant purified GDF-8 and/or propeptide. The immunoprecipitate was analyzed by western blotting as in (A).

To confirm and further characterize the interaction between GDF-8 and GASP1, we incubated purified recombinant GDF-8 and purified recombinant GDF-8 propeptide with conditioned media from COS1 cells transfected with either a vector control or GASP1-V5-His. We then immunoprecipitated GDF-8 with JA16-conjugated agarose beads and looked for co-purification of GASP1 and GDF-8 propeptide using western blots (FIG. 15A). Both GASP1 (lane 3) and GDF-8 propeptide (lane 1) co-immunoprecipitated with GDF-8, proving that GDF-8 can interact with both of these proteins. Neither GASP1 nor propeptide were detected in JA16 immunoprecipitates in the absence of GDF-8 (lane 4), eliminating the possibility of non-specific binding in these experiments. When all three proteins were present, both GASP1 and GDF-8 propeptide were pulled down with GDF-8, suggesting the possibility that these proteins may form a tertiary complex (lane 5). However, this experiment does not eliminate the possibility that GASP1 and propeptide are bound to the same epitope on separate GDF-8 molecules.

To further confirm the interaction between GASP1 and GDF-8, we performed the reverse immunoprecipitation by pulling down GASP1 from conditioned media supplemented with GDF-8 and/or GDF-8 propeptide recombinant protein. To achieve this, we used an agarose-conjugated monoclonal antibody directed against the V5 epitope of the C-terminal V5-His tag on GASP1. As expected, GDF-8 co-immunoprecipitated with GASP1 (FIG. 15B, lanes 3 and 5), further confirming a direct interaction between these proteins. Surprisingly, GDF-8 propeptide also co-purified with GASP1, even in the absence of GDF-8 (lane 4), suggesting that GDF-8 propeptide can bind directly to GASP1. Thus, GASP1 binds to both GDF-8 and GDF-8 propeptide independently. This is in contrast to FLRG, another follistatin-domain protein, that binds exclusively to mature GDF-8 (Hill et al. (2002) *J. Biol. Chem.*, 277: 40735–40741). Addition of both GDF-8 and propeptide consistently showed less propeptide binding to GASP1 than when propeptide was added alone. This observation suggests that GASP1 may not bind to the GDF-8 small latent complex.

Example 11

GASP1-Mediated Inhibition of GDF-8 and BMP-11, But Not Activin or TGF-β1, Activity A luciferase reporter construct, pGL3-(CAGA)$_{12}$ (SEQ ID NO:53) (Dennler et al. (1998) *EMBO J.*, 17: 3091–3100) was transiently transfected into A204 or RD rhabdomyosarcoma cells. Dilutions of conditioned media from vector or GASP1 transfected cells were incubated for 30 minutes at 37° C. with 10 ng/ml GDF-8, 10 ng/ml BMP-11,10 ng/ml rh activin A (R&D Systems), or 0.5 ng/ml rh TGF-β1 (R&D Systems). Luciferase activity was measured according to Thies et al. (2001) *Growth Factors*, 18: 251–259 and Zimmers et al. (2002) *Science*, 296: 1486–1488. In this assay, A204 cells respond to GDF-8, BMP-11, and activin, but do not respond well to TGF-β1. RD cells respond to both GDF-8 and TGF-β1. Thus, we used A204 cells to test for the ability of GASP1 to inhibit GDF-8, BMP-11, and activin and RD cells to monitor the activity of TGF-β and GDF-8. Results for GDF-8 are shown from A204 cells, but were similar in RD cells. A standard curve measuring the concentration dependence of the luciferase activity induced by each of these growth factors was generated for each experiment (data not shown). The growth factor concentrations used fall in the linear region of this curve such that small changes in concentration result in measurable changes in luciferase activity.

Two follistatin-domain proteins, follistatin and FLRG inhibit GDF-8 activity in a (CAGA)$_{12}$ (SEQ ID NO:53) luciferase transcriptional reporter assay, but also inhibit the biological activity of the related proteins, activin and BMP-11. The ability of GASP1 to inhibit GDF-8, BMP-11, activin, and TGF-β1 activity in the (CAGA)$_{12}$ (SEQ ID NO:53) reporter assay was also tested.

Figure 16A:
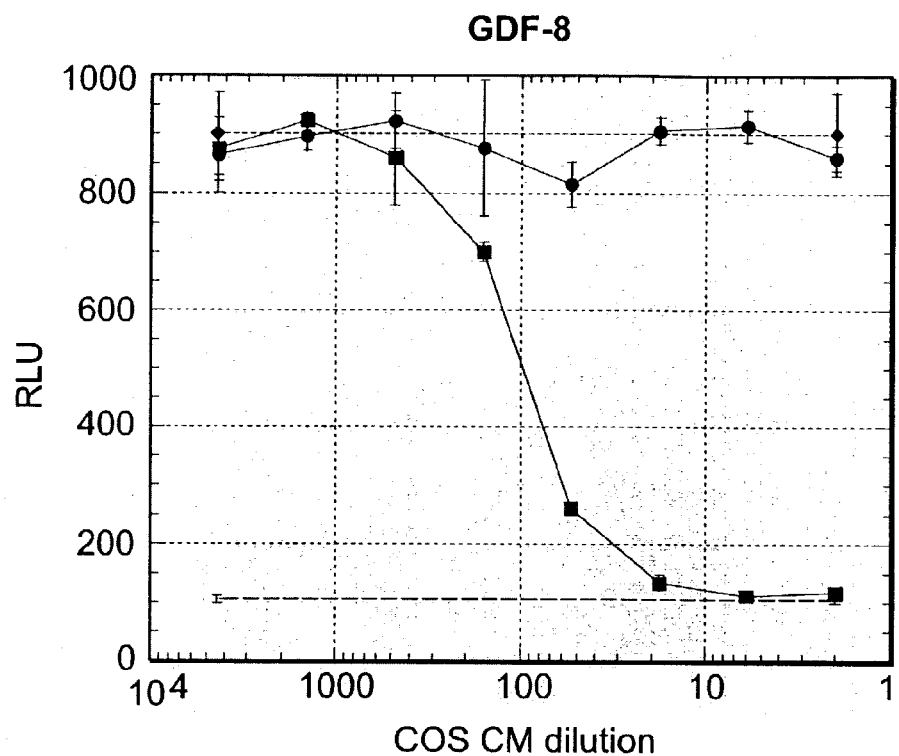
FIG. 16 shows that GASP1 inhibits the biological activity of GDF-8 and the highly related BMP-11, but not activin or TGF-β. Various dilutions of conditioned media from mock (open circles) or GASP1-V5-His (filled squares) transfectants were incubated with (A) 10 ng/ml GDF-8, (B) 10 ng/ml BMP-11, (C) 10 ng/ml activin, or (D) 0.5 ng/ml TGF-β. These samples were then subjected to a luciferase reporter activity assay in A204 (A–C) or RD (D) cells to determine the activity of the added growth factors. Luciferase activity is shown in relative luciferase units. The activity resulting from each of the growth factors alone is shown by the filled diamonds and short dashed line. Without addition of any growth factor, the background activity in the assay is low, as shown by the long dashed line with no symbols.
Figure 16B:
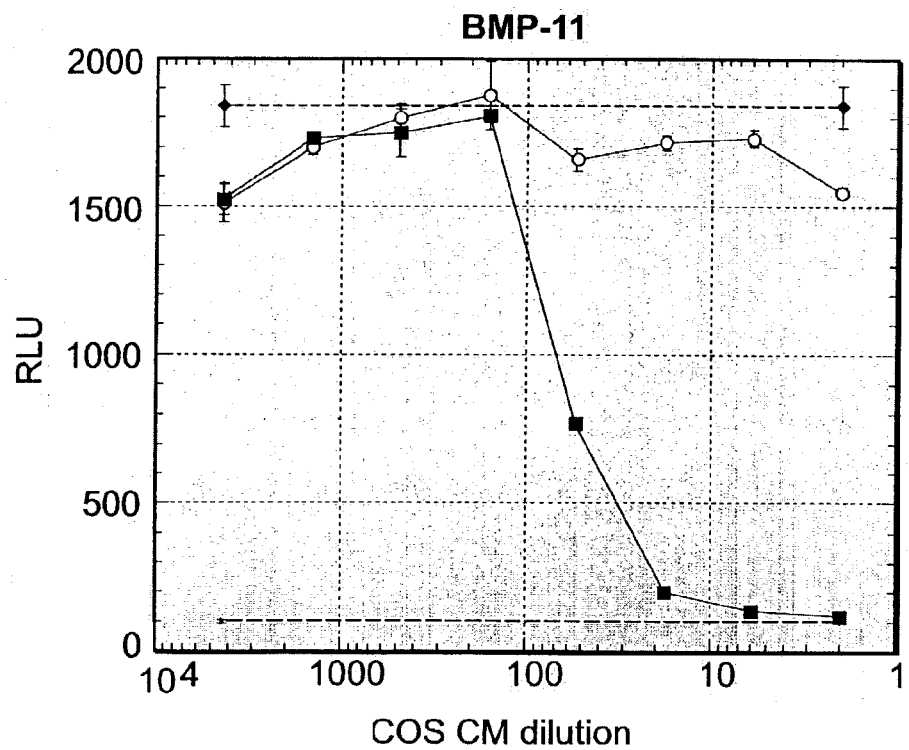
Figure 16C:
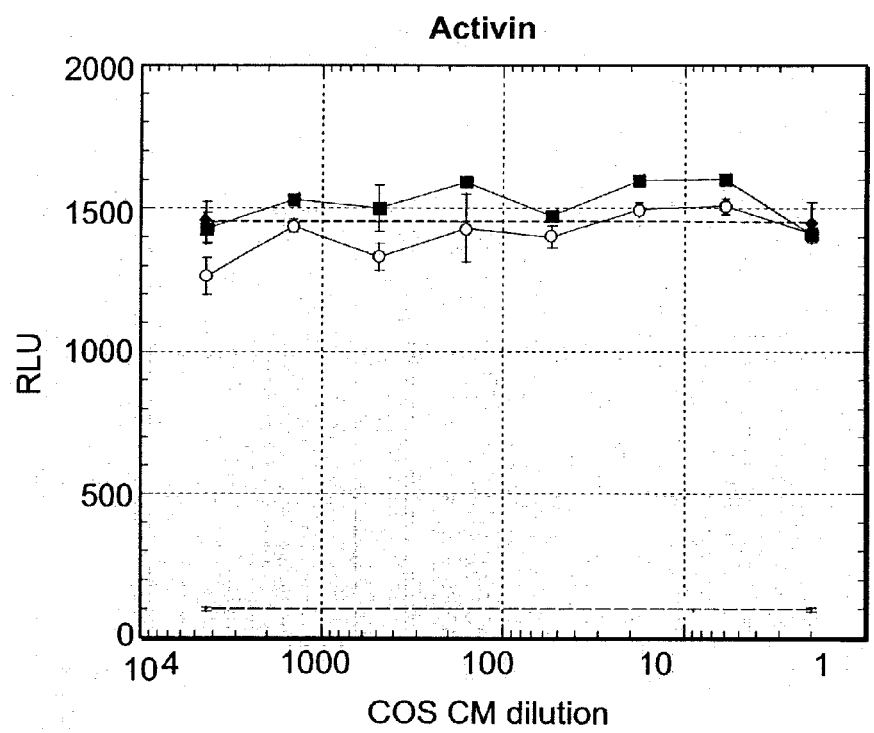
Figure 16D:
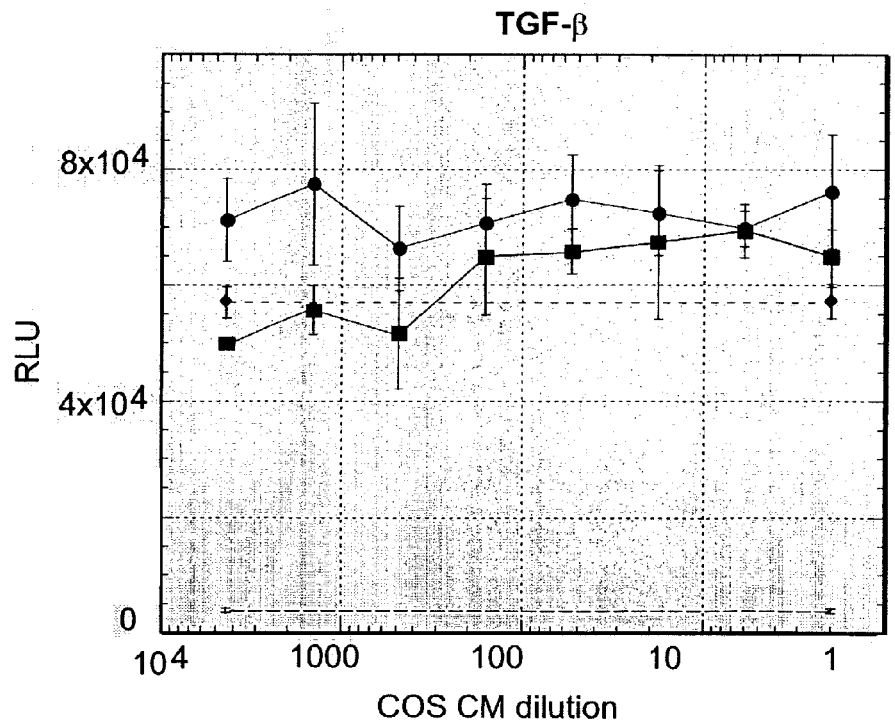

Various dilutions of conditioned media from COS cells transfected with V5-His tagged GASP1 or a vector control were incubated with purified recombinant GDF-8 (10 ng/ml), BMP-11 (10 ng/ml), activin (10 ng/ml), or TGF-β1 (0.5 ng/ml) and assayed for growth factor activity in rhabdomyosarcoma cells expressing the (CAGA)$_{12}$ (SEQ ID NO:53) reporter construct. GASP1 potently inhibited GDF-8 activity in a concentration dependent manner (FIG. 16A). GASP1 similarly inhibited the activity of BMP-11 in this assay (FIG. 16B), as might be expected since mature GDF-8 and BMP-11 are highly conserved and differ by only 11 amino acids. Surprisingly, GASP1 did not inhibit the activity of activin or TGF-β1 (FIGS. 16C and D), suggesting a very high level of specificity, which is not demonstrated by follistatin itself. Thus, GASP1 exhibits specificity in its inhibition of GDF-8 and BMP-11.

Figure 17:
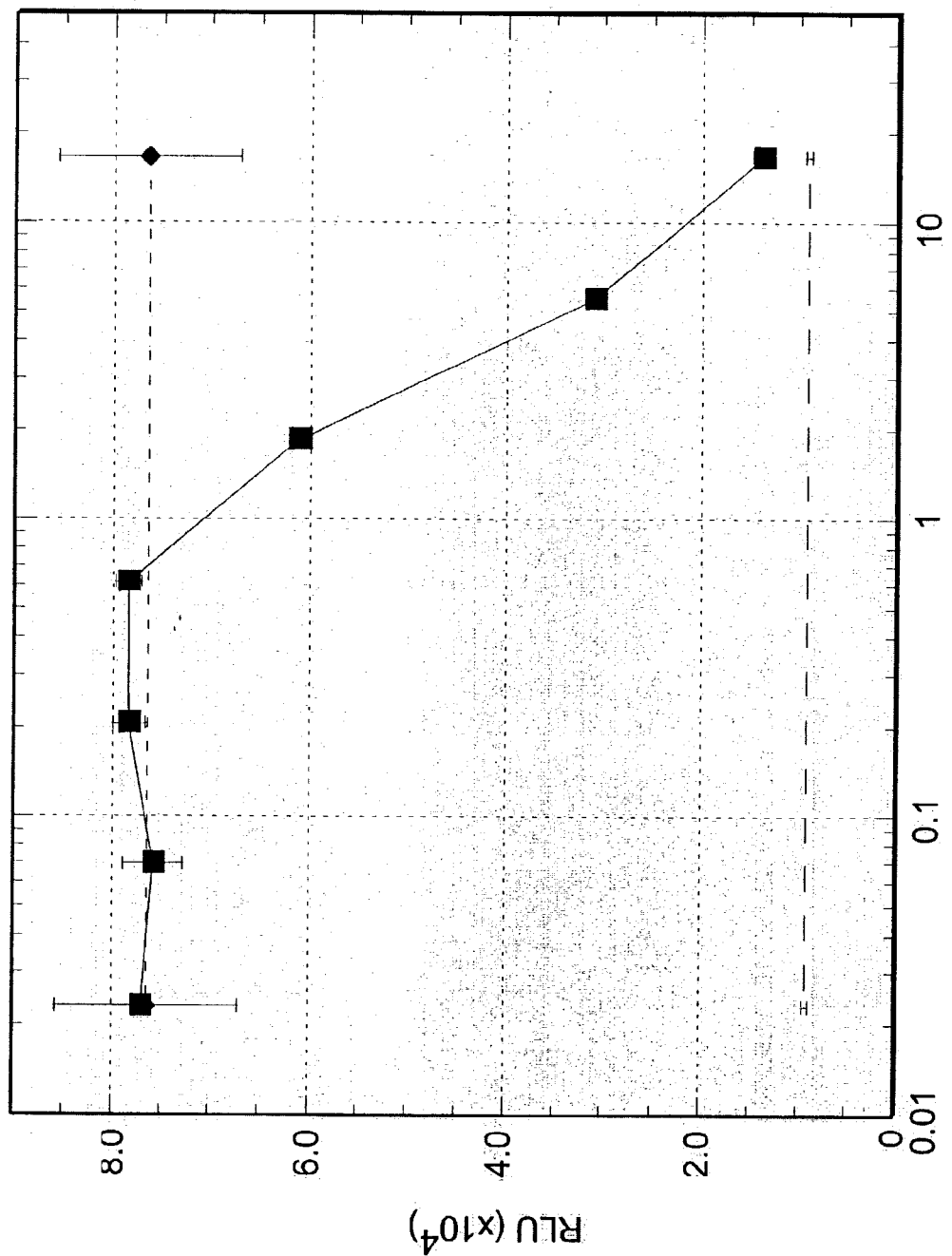
FIG. 17 shows the potency of GASP1 inhibition of GDF-8. Purified GASP1 was tested for its ability to inhibit 20 ng/ml of myostatin in the $(CAGA)_{12}$ (SEQ ID NO:53) luciferase reporter assay in RD cells (filled squares). The activity resulting from GDF-8 alone is shown by the filled diamonds and short dashed line. The activity present when no growth factors are added is shown by the long dashed line.

The affinity of GASP1 for GDF-8 was evaluated by determining the IC50 for inhibition of GDF-8 in the reporter gene assay. GASP1-V5-His protein was purified from conditioned media on a cobalt affinity column and eluted as described above. Fractions containing GASP1 were further purified by size exclusion chromatography in PBS using a BioSepS3000 column (Phenomenex). As shown in FIG. 17, GASP1 inhibited GDF-8 with an IC50 of approximately 3 nM.

Example 12

Treatment of Muscle Disorders

GASP1 may be administered to patients suffering from a disease or disorder related to the functioning of GDF-8 according to Table 2. Patients take the composition one time or at intervals, such as once daily, and the symptoms of their disease or disorder improve. For example, symptoms related to a muscle disorder are improved, as measured by muscle mass, muscle activity, and or muscle tone. This shows that the composition of the invention is useful for the treatment of diseases or disorders related to the functioning of GDF-8, such as muscle disorders.

TABLE 2

Administration of GASP1

| Patient | Disease | Route of Administration | Dosage | Dosage Frequency | Predicted Results |
|---|---|---|---|---|---|
| 1 | muscular dystrophy | subcutaneous | 25 mg | once daily | increase in muscle mass and improvement in muscle activity |
| 2 | muscular dystrophy | " | 50 mg | " | increase in muscle mass and improvement in muscle activity |
| 3 | muscular dystrophy | " | 50 mg | once weekly | increase in muscle mass and improvement in muscle activity |
| 4 | muscular dystrophy | " | 50 mg | once monthly | increase in muscle mass and improvement in muscle activity |
| 5 | muscular dystrophy | intramuscular | 25 mg | once daily | increase in muscle mass and improvement in muscle activity |
| 6 | muscular dystrophy | " | 50 mg | " | increase in muscle mass and improvement in muscle activity |
| 7 | muscular dystrophy | " | 50 mg | once weekly | increase in muscle mass and improvement in muscle activity |
| 8 | muscular dystrophy | " | 50 mg | once monthly | increase in muscle mass and improvement in muscle activity |
| 9 | muscular dystrophy | intravenous | 25 mg | once daily | increase in muscle mass and improvement in muscle activity |
| 10 | muscular dystrophy | " | 50 mg | " | increase in muscle mass and improvement in muscle activity |
| 11 | muscular dystrophy | " | 50 mg | once weekly | increase in muscle mass and improvement in muscle activity |
| 12 | muscular dystrophy | " | 50 mg | once monthly | increase in muscle mass and improvement in muscle activity |
| 13 | diabetes | subcutaneous | 50 mg | once daily | improvement in the management of blood sugar levels |
| 14 | " | " | 50 mg | once weekly | improvement in the management of blood sugar levels |
| 15 | " | intramuscular | 50 mg | " | improvement in the management of blood sugar levels |
| 16 | " | intravenous | 50 mg | " | improvement in the management of blood sugar levels |
| 17 | obesity | subcutaneous | 50 mg | once daily | weight loss and increase in muscle mass |
| 18 | " | intramuscular | 50 mg | once weekly | weight loss and increase in muscle mass |
| 19 | " | intravenous | 50 mg | " | weight loss and increase in muscle mass |

The entire contents of all references, patents and published patent applications cited throughout this application are herein incorporated by reference. The foregoing detailed description has been given for illustration purposes only. A wide range of changes and modifications can be made to the embodiments described above. It should therefore be understood that it is the following claims, including all equivalents, are intended to define the scope of the invention.

We claim:

1. A diagnostic kit for a GDF-8-associated disorder comprising the following separate components:
   (a) a GASP-1 protein having GDF-8 binding activity, wherein the GASP1 protein comprises an amino acid sequence encoded by a nucleic acid sequence chosen from:
      i. nucleotides 520–717 of SEQ ID NO:4;
      ii. a nucleotide sequence that is at least 95% identical to (i) and encodes a polypeptide having GDF-8 binding activity; and
   (b) a buffer or solution; and
   (c) a detectable label for detecting the GASP1 protein chosen from a fluorophore, chromophore, radioactive molecule, electron-dense molecule and an enzyme; and
   d. a GDF-8 protein.

2. The kit of claim 1, wherein the GDF-8 protein is unprocessed GDF-8.

3. The kit of claim 1, wherein the GDF-8 protein is mature GDF-8.

4. The kit of claim 1, wherein the GDF-8 protein is GDF-8 propeptide.

5. The kit of claim 1, wherein the GASP1 protein comprises a detectable label for detecting GASP1.

6. The kit of claim 5, wherein the detectable label is an enzyme.

7. The kit of claim 5, wherein the GASP1 protein comprises a moiety chosen from a His-tag, V5-tag, V5-His tag, horseradish peroxidase, biotin, avidin, streptavidin, IgG, and protein A.

8. A kit for detecting GDF-8 protein, wherein the kit comprises the following separate components:
   (a) a GASP-1 polpypeptide comprising an amino acid sequence encoded by a nucleic acid sequence chosen from.
      i. nucleotides 520–717 of SEQ ID NO:4;
      ii. a nucleotide sequence that is at least 95% identical to (i) and encodes a polpeptide having GDF-8 binding activity; and
   (b) a buffer or solution; and
   (c) a GDF-8 protein.

9. A kit for detecting GDF-8 protein, wherein the kit comprises the following separate components:
   (a) a GASP-1 polypeptide comprising an amino acid sequence chosen from:
      (i) amino acids 174 to 239 of SEQ ID NO:5;
      (ii). SEQ. ID NO:5;
      (ii) SEQ ID NO:7; and
   (b) a buffer or solution; and
   (c) a GDF-8 protein.

10. The kit of claim 8 wherein the GASP1 protein comprises an amino acid sequence encoded by a nucleic acid sequence encoded by a nucleic acid sequence chosen from:
   (a) SEQ ID NO:4;
   (b) SEQ ID NO:6;
   (c) a nucleotide sequence that is at least 95% identical to (a) or (b) and encodes a polypeptide having GDF-8 binding activity.

11. The kit of claim 8, wherein the GASP1 protein consists of an amino acid sequence encoded by a nucleic acid sequence encoded by a nucleic acid sequence chosen from:
   (a) nucleotides 520–717 of SEQ ID NO:4;
   (b) SEQ ID NO:4;
   (c) SEQ ID NO:6
   (d) a nucleotide sequence that is at least 95% identical to (a), (b) or (c) and encodes a polypeptide having GDF-8 binding activity.

12. The kit of claim 8, wherein nucleic acid sequence is at least 96% identical to:
   (a) nucleotides 520–717 of SEQ ID NO:4;
   (b) SEQ ID NO:4; or
   (c) SEQ ID NO:6.

13. The kit of claim 8, wherein the nucleic acid sequence comprises
   (a) nucleotides 520–717 of SEQ ID NO:4;
   (b) SEQ ID NO:4; or
   (c) SEQ ID NO:6.

14. The kit of claim 8, wherein the GASP1 protein comprises a GASP1 moiety having GDF-8 binding activity and an optional heterologous sequence, wherein the GASP1 moiety is encoded by a nucleotide sequence chosen from:
   (a) nucleotides 520–717 of SEQ ID No. 4;
   (b) SEQ ID NO:4;
   (c) SEQ ID NO:6; and
   (d) a nucleotide sequence that is at least 95% identical to (a), (b), or (c) and encodes a polypeptide having GDF-8 binding activity.

15. The kit of claim 8, wherein the GDF-8 binding activity is specific binding to a GDF-8 latent complex.

16. The kit of claim 8, wherein the GDF-8 binding activity is specific binding to mature GDF-8.

17. The kit of claim 16, wherein the mature GDF-8 is in monomeric form, in dimeric form, or in a GDF-8 latent complex.

18. The kit of claim 8, wherein the GDF-8 binding activity is specific binding to GDF-8 propeptide.

19. The kit of claim 18, wherein the GDF-8 propeptide is in monomeric form or in a GDF-8 latent complex.

20. The kit of claim 8, wherein the GDF-8 protein is unprocessed GDF-8.

21. The kit of claim 8, wherein the GDF-8 protein is mature GDF-8.

22. The kit of claim 8, wherein the GDF-8 protein is GDF-8 propeptide.

23. The kit of claim 8, wherein the kit further comprises a detectable label chosen from a fluorophore, chromophore, and radioactive molecule.

24. The kit of claim 8, wherein the kit further comprises an enzyme detectable marker.

25. The kit of claim 8, wherein the GASP1 protein comprises a moiety chosen from a His-tag, V5-tag, V5-His tag, horseradish peroxidase, biotin, avidin, streptavidin, IgG, or protein A.

* * * * *

UNITED STATES PATENT AND TRADEMARK OFFICE
CERTIFICATE OF CORRECTION

PATENT NO.         : 7,192,717 B2
APPLICATION NO. : 10/369736
DATED                 : March 20, 2007
INVENTOR(S)       : Jennifer J. Hill and Neil M. Wolfman It is certified that error appears in the above-identified patent and that said Letters Patent is hereby corrected as shown below:

IN THE CLAIMS:

In claim 1, column 77, line 12, change "GASP-1" to --GASP1--

In claim 1, column 77, line 20, delete "and"

In claim 1, column 77, line 25, change "d." to --(d)--

In claim 8, column 77, line 42, change "GASP-1 polpypeptide" to --GASP1 polypeptide--

In claim 8, column 77, line 44, change "." following "from", to --:--

In claim 8, column 77, line 47, change "polpeptide" to --polypeptide--

In claim 9, column 77, line 53, change "GASP-1" to --GASP1--

In claim 9, column 77, line 56, delete "." following "(ii)" and "SEQ" and insert --and-- following "NO:5";

In claim 9, column 77, line 57, change "(ii)" to --(iii)-- and delete "and" following "NO:7";

In claim 10, column 77, line 62, delete "encoded by a nucleic acid sequence"

In claim 10, column 77, line 64, following "NO:6"; insert --and--

In claim 11, column 78, line 12, delete "encoded by a nucleic acid sequence"

In claim 11, column 78, line 16, add --; and-- following "SEQ ID NO. 6"

In claim 13, column 78, line 26, add --:-- following "comprises"

In claim 14, column 78, line 34, change "No." to --NO:--

UNITED STATES PATENT AND TRADEMARK OFFICE
CERTIFICATE OF CORRECTION

PATENT NO. : 7,192,717 B2
APPLICATION NO. : 10/369736
DATED : March 20, 2007
INVENTOR(S) : Jennifer J. Hill and Neil M. Wolfman It is certified that error appears in the above-identified patent and that said Letters Patent is hereby corrected as shown below:

In claim 25, column 78, line 65, replace "or" with --and--

Signed and Sealed this

Twenty-first Day of August, 2007

JON W. DUDAS
*Director of the United States Patent and Trademark Office*

SEQUENCE LISTING

<160> NUMBER OF SEQ ID NOS: 53

<210> SEQ ID NO 1
<211> LENGTH: 1716
<212> TYPE: DNA
<213> ORGANISM: Mus sp.

<400> SEQUENCE: 1

| | | | | | |
|---|---|---|---|---|---|
| atgtgtgccc | cagggtatca | tcggttctgg | tttcactggg | ggctgctgtt | gctgctgctc | 60 |
| ctcgaggctc | cccttcgagg | cctagcactg | ccacccatcc | gatactccca | tgcgggcatc | 120 |
| tgccccaacg | acatgaaccc | caacctctgg | gtggatgccc | agagcacctg | caagcgagag | 180 |
| tgtgaaacag | accaggaatg | tgagacctat | gagaaatgct | gccccaatgt | gtgtgggacc | 240 |
| aagagctgtg | tggcagcccg | ctacatggat | gtgaaggga | agaagggccc | tgtgggcatg | 300 |
| cccaaggagg | ccacatgtga | ccatttcatg | tgcctgcagc | agggctctga | gtgtgacatc | 360 |
| tgggacggcc | agcccgtgtg | taagtgcaaa | gatcgctgtg | agaaggagcc | cagcttcacc | 420 |
| tgtgcctctg | atggccttac | ctactacaac | cgttgcttca | tggacgccga | agcctgctcc | 480 |
| aagggcatca | cactgtctgt | ggtcacctgt | cgttatcact | tcacctggcc | taacaccagc | 540 |
| cctccaccgc | ctgagaccac | ggtgcatccc | accaccgcct | ctccggagac | tctcgggctg | 600 |
| gacatggcag | ccccggccct | gctcaaccac | cctgtccatc | agtcagtcac | cgtgggtgag | 660 |
| actgtgagtt | tcctctgtga | cgtggtaggc | cggcctcggc | cagagctcac | ttgggagaaa | 720 |
| cagctggagg | accgagaaaa | tgttgtcatg | aggcccaacc | acgtgcgcgg | taatgtggtg | 780 |
| gtcactaaca | ttgcccagct | ggtcatctac | aacgtccagc | cccaggatgc | tggcatatac | 840 |
| acctgtacag | ctcgaaatgt | cgctggtgtc | ctgagggctg | acttcccgtt | gtcggtggtc | 900 |
| aggggtggtc | aggccagggc | cacttcagag | agcagtctca | atggcacagc | ttttccagca | 960 |
| acagagtgcc | tgaagccccc | agacagtgag | gactgtggag | aggagcagac | acgctggcac | 1020 |
| ttcgacgccc | aggctaacaa | ctgcctcact | ttcacctttg | gccactgcca | ccacaatctc | 1080 |
| aaccactttg | agacctacga | ggcctgtatg | ctggcttgta | tgagtgggcc | attggccacc | 1140 |
| tgcagcctgc | ctgccctgca | agggccttgc | aaagcttatg | tcccacgctg | ggcctacaac | 1200 |
| agccagacag | gcctatgcca | gtccttcgtc | tatggcggct | gtgagggcaa | cggtaacaac | 1260 |
| tttgaaagcc | gtgaggcttg | tgaggagtcg | tgtccccttcc | cgagggtaa | ccagcactgc | 1320 |
| cgggcctgca | agccccggca | aaaacttgtt | accagcttct | gtcggagtga | ctttgtcatc | 1380 |
| ctgggcaggg | tctctgagct | gaccgaagag | caagactcag | gccgtgccct | ggtgaccgtg | 1440 |
| gatgaggtct | taaagatga | gaagatgggc | ctcaagtttc | tgggccggga | gcctctggaa | 1500 |
| gtcaccctgc | ttcatgtaga | ctggacctgt | ccttgcccca | acgtgacagt | gggtgagaca | 1560 |
| ccactcatca | tcatggggga | ggtcgacggc | ggcatggcca | tgctgagacc | cgatagcttt | 1620 |
| gtgggggcat | cgagcacacg | gcgggtcagg | aagctccgtg | aggtcatgta | caagaaaacc | 1680 |
| tgtgacgtcc | tcaaggactt | cctgggcttg | caatga | | 1716 |

<210> SEQ ID NO 2
<211> LENGTH: 1716

```
<212> TYPE: DNA
<213> ORGANISM: Mus sp.

<400> SEQUENCE: 2
atgtgtgccc cagggtatca tcggttctgg tttcactggg ggctgctgtt gctgctgctc      60
ctcgaggctc cccttcgagg cctagcactg ccacccatcc gatactccca tgcgggcatc     120
tgccccaacg acatgaaccc caacctctgg gtggatgccc agagcacctg caagcgagag     180
tgtgaaacag accaggaatg tgagacctat gagaaatgct gccccaatgt gtgtgggacc     240
aagagctgtg tggcagcccg ctacatggat gtgaaaggga agaaggggcc tgtaggcatg     300
cccaaggagg ccacatgtga ccatttcatg tgcctgcagc agggctctga gtgtgacatc     360
tgggacggcc agcccgtgtg taagtgcaaa gatcgctgtg agaaggagcc cagcttcacc     420
tgtgcctctg atggccttac ctactacaac cgttgcttca tggacgccga gcctgctcc      480
aagggcatca cactgtctgt ggtcacctgt cgttatcact tcacctggcc taacaccagc     540
cctccaccgc ctgagaccac ggtgcatccc accaccgcct ctccggagac tctcgggctg     600
gacatggcag ccccagccct gctcaaccac cctgtccatc agtcagtcac cgtgggtgag     660
actgtgagtt tcctctgtga cgtggtaggc cggcctcggc cagagctcac ttgggagaaa     720
cagctggagg accgagagaa tgttgtcatg aggcccaacc acgtgcgtgg taatgtggtg     780
gtcactaaca ttgcccagct ggtcatctac aacgtccagc ccaggatgc  tggcatatac     840
acctgtacag ctcgaaatgt cgctggtgtc ctgagggctg acttcccgtt gtcggtggtc     900
aggggtggtc aggccagggc cacttcagag agcagtctca atggcacagc ttttccagca     960
acagagtgcc tgaagccccc agacagtgag gactgtggag aggagcagac acgctggcac    1020
ttcgacgccc aggctaacaa ctgcctcact ttcacctttg ccactgcca ccacaatctc     1080
aaccactttg agacctacga ggcctgtatg ctggcttgta tgagtgggcc attggccacc    1140
tgcagcctgc ctgccctgca agggccttgc aaagcttatg tcccacgctg gcctacaac     1200
agccagacag gcctatgcca gtccttcgtc tatggcggct gtgagggcaa cggtaacaac    1260
tttgaaagcc gtgaggcttg tgaggagtcg tgtcccttcc cgagggtaa ccagcactgc     1320
cgggcctgca agccccggca aaaacttgtt accagcttct gtcggagtga ctttgtcatc    1380
ctgggcaggg tctctgagct gaccgaggag caagactcgg gccgtgccct ggtgaccgtg    1440
gatgaggtct aaaagatga aagatgggc ctcaagtttc tgggccggga gcctctggaa      1500
gtcaccctgc ttcatgtaga ctggacctgt ccttgcccca acgtgacagt gggtgagaca    1560
ccactcatca tcatgggga ggtggacggc ggcatggcca tgctgagacc cgatagcttt     1620
gtgggggcat cgagcacacg gcgggtcagg aagctccgtg aggtcatgta caagaaaacc    1680
tgtgacgtcc tcaaggactt cctgggcttg caatga                             1716

<210> SEQ ID NO 3
<211> LENGTH: 571
<212> TYPE: PRT
<213> ORGANISM: Mus sp.

<400> SEQUENCE: 3

Met Cys Ala Pro Gly Tyr His Arg Phe Trp Phe His Trp Gly Leu Leu
  1               5                  10                  15

Leu Leu Leu Leu Leu Glu Ala Pro Leu Arg Gly Leu Ala Leu Pro Pro
                 20                  25                  30

Ile Arg Tyr Ser His Ala Gly Ile Cys Pro Asn Asp Met Asn Pro Asn
             35                  40                  45
```

-continued

```
Leu Trp Val Asp Ala Gln Ser Thr Cys Lys Arg Glu Cys Glu Thr Asp
     50                  55                  60
Gln Glu Cys Glu Thr Tyr Lys Cys Cys Pro Asn Val Cys Gly Thr
 65                  70                  75                  80
Lys Ser Cys Val Ala Ala Arg Tyr Met Asp Val Lys Gly Lys Lys Gly
                 85                  90                  95
Pro Val Gly Met Pro Lys Glu Ala Thr Cys Asp His Phe Met Cys Leu
                100                 105                 110
Gln Gln Gly Ser Glu Cys Asp Ile Trp Asp Gly Gln Pro Val Cys Lys
             115                 120                 125
Cys Lys Asp Arg Cys Glu Lys Glu Pro Ser Phe Thr Cys Ala Ser Asp
         130                 135                 140
Gly Leu Thr Tyr Tyr Asn Arg Cys Phe Met Asp Ala Glu Ala Cys Ser
145                 150                 155                 160
Lys Gly Ile Thr Leu Ser Val Val Thr Cys Arg Tyr His Phe Thr Trp
                165                 170                 175
Pro Asn Thr Ser Pro Pro Pro Glu Thr Thr Val His Pro Thr Thr
                180                 185                 190
Ala Ser Pro Glu Thr Leu Gly Leu Asp Met Ala Ala Pro Ala Leu Leu
        195                 200                 205
Asn His Pro Val His Gln Ser Val Thr Val Gly Glu Thr Val Ser Phe
210                 215                 220
Leu Cys Asp Val Val Gly Arg Pro Arg Pro Glu Leu Thr Trp Glu Lys
225                 230                 235                 240
Gln Leu Glu Asp Arg Glu Asn Val Val Met Arg Pro Asn His Val Arg
                245                 250                 255
Gly Asn Val Val Val Thr Asn Ile Ala Gln Leu Val Ile Tyr Asn Val
                260                 265                 270
Gln Pro Gln Asp Ala Gly Ile Tyr Thr Cys Thr Ala Arg Asn Val Ala
        275                 280                 285
Gly Val Leu Arg Ala Asp Phe Pro Leu Ser Val Val Arg Gly Gly Gln
    290                 295                 300
Ala Arg Ala Thr Ser Glu Ser Ser Leu Asn Gly Thr Ala Phe Pro Ala
305                 310                 315                 320
Thr Glu Cys Leu Lys Pro Pro Asp Ser Glu Asp Cys Gly Glu Glu Gln
                325                 330                 335
Thr Arg Trp His Phe Asp Ala Gln Ala Asn Asn Cys Leu Thr Phe Thr
                340                 345                 350
Phe Gly His Cys His His Asn Leu Asn His Phe Glu Thr Tyr Glu Ala
            355                 360                 365
Cys Met Leu Ala Cys Met Ser Gly Pro Leu Ala Thr Cys Ser Leu Pro
        370                 375                 380
Ala Leu Gln Gly Pro Cys Lys Ala Tyr Val Pro Arg Trp Ala Tyr Asn
385                 390                 395                 400
Ser Gln Thr Gly Leu Cys Gln Ser Phe Val Tyr Gly Gly Cys Glu Gly
                405                 410                 415
Asn Gly Asn Asn Phe Glu Ser Arg Glu Ala Cys Glu Glu Ser Cys Pro
                420                 425                 430
Phe Pro Arg Gly Asn Gln His Cys Arg Ala Cys Lys Pro Arg Gln Lys
            435                 440                 445
Leu Val Thr Ser Phe Cys Arg Ser Asp Phe Val Ile Leu Gly Arg Val
450                 455                 460
```

| | | | | | | | | | | | | |
|---|---|---|---|---|---|---|---|---|---|---|---|---|
|Ser|Glu|Leu|Thr|Glu|Glu|Gln|Asp|Ser|Gly|Arg|Ala|Leu|Val|Thr|Val|
|465| | | | |470| | | | |475| | | | |480|

Ser Glu Leu Thr Glu Glu Gln Asp Ser Gly Arg Ala Leu Val Thr Val
465                 470                 475                 480

Asp Glu Val Leu Lys Asp Glu Lys Met Gly Leu Lys Phe Leu Gly Arg
                485                 490                 495

Glu Pro Leu Glu Val Thr Leu Leu His Val Asp Trp Thr Cys Pro Cys
            500                 505                 510

Pro Asn Val Thr Val Gly Glu Thr Pro Leu Ile Ile Met Gly Glu Val
        515                 520                 525

Asp Gly Gly Met Ala Met Leu Arg Pro Asp Ser Phe Val Gly Ala Ser
    530                 535                 540

Ser Thr Arg Arg Val Arg Lys Leu Arg Glu Val Met Tyr Lys Lys Thr
545                 550                 555                 560

Cys Asp Val Leu Lys Asp Phe Leu Gly Leu Gln
                565                 570

<210> SEQ ID NO 4
<211> LENGTH: 1923
<212> TYPE: DNA
<213> ORGANISM: Homo sapiens
<220> FEATURE:
<221> NAME/KEY: modified_base
<222> LOCATION: (732)
<223> OTHER INFORMATION: a, t, c or g

<400> SEQUENCE: 4

```
atgaatccca acctctgggt ggacgcacag agcacctgca ggcgggagtg tgagacggac      60
caggagtgtg agatggacca ggtgagtggg atccagaagc cacagtgtga ggcagaccag     120
gtgaatgggg tccagaagcc gcaatgtgag atggaccaga agtgggagtg tgaggttgac     180
caggtgagtg gggtccagaa gccggtgtgt gaggcggacc aggtgagtgg ggtccagaag     240
ccacagtgtg agatggacca ggtgagtggg atccagaagc tggagtgtga ggcggaccag     300
aagtgggagt gtgaggtgga ccaggtgagt ggggtccaga agccacagtg tgagatggac     360
caggtgagtg ggatccagaa gctggagtgt gaggcggacc aggagtgtga gacctatgag     420
aagtgctgcc ccaacgtatg tgggaccaag agctgcgtgg cggcccgcta catgacgtg      480
aaagggaaga agggcccagt gggcatgccc aaggaggcca catgtgacca cttcatgtgt     540
ctgcagcagg gctctgagtg tgacatctgg gatggccagc ccgtgtgtaa gtgcaaagac     600
cgctgtgaga aggagcccag ctttacctgc gcctcggacg gcctcaccta ctataaccgc     660
tgctacatgg atgccgaggc tgctccaaaa ggcatcacac tggccgttgt aacctgccgc     720
tatcacttca cntggcccaa caccagcccc ccaccacctg agaccaccat gcaccccacc     780
acagcctccc cagagacccc tgagctggac atggcggccc ctgcgctgct caacaaccct     840
gtgcaccagt cggtcaccat gggtgagaca gtgagcttcc tctgtgatgt ggtgggccgg     900
ccccggcctg agatcacctg ggagaagcag ttggaggatc gggagaatgt ggtcatgcgg     960
cccaaccatg tgcgtggcaa cgtggtggtc accaacattg cccagctggt catctataac    1020
gcccagctgc aggatgctgg gatctacacc tgcacggccc ggaacgtggc tggggtcctg    1080
agggctgatt tcccgctgtc ggtggtcagg ggtcatcagg ctgcagccac ctcagagagc    1140
agccccaatg gcacggcttt ccggcggcc gagtgcctga gcccccaga cagtgaggac    1200
tgtggcgaag agcagacccg ctggcacttc gatgcccagg ccaacaactg cctgaccttc    1260
accttcggcc actgccaccg taacctcaac cactttgaga cctatgaggc ctgcatgctg    1320
gcctgcatga gcgggccgct ggccgcgtgc agcctgcccg ccctgcaggg gccctgcaaa    1380
```

-continued

```
gcctacgcgc tcgctgggc ttacaacagc cagacgggcc agtgccagtc ctttgtctat    1440
ggtggctgcg agggcaatgg caacaacttt gagagccgtg aggcctgtga ggagtcgtgc    1500
cccttcccca gggggaacca gcgctgtcgg gcctgcaagc ctcggcagaa gctcgttacc    1560
agcttctgtc gcagcgactt tgtcatcctg ggccgagtct ctgagctgac cgaggagcct    1620
gactcgggcc gcgccctggt gactgtggat gaggtcctaa aggatgagaa aatgggcctc    1680
aagttcctgg gccaggagcc attggaggtc actctgcttc acgtgactg ggcatgcccc     1740 tgccccaacg tgaccgtgag cgagatgccg ctcatcatca tggggaggt ggacggcggc     1800 atggccatgc tgcgccccga tagctttgtg gcgcatcga gtgcccgccg ggtcaggaag     1860
cttcgtgagg tcatgcacaa gaagacctgt gacgtcctca aggagtttct tggcttgcac    1920
tga                                                                   1923
```

<210> SEQ ID NO 5
<211> LENGTH: 640
<212> TYPE: PRT
<213> ORGANISM: Homo sapiens

<400> SEQUENCE: 5

```
Met Asn Pro Asn Leu Trp Val Asp Ala Gln Ser Thr Cys Arg Arg Glu
 1               5                  10                  15

Cys Glu Thr Asp Gln Glu Cys Glu Met Asp Gln Val Ser Gly Ile Gln
            20                  25                  30

Lys Pro Gln Cys Glu Ala Asp Gln Val Asn Gly Val Gln Lys Pro Gln
        35                  40                  45

Cys Glu Met Asp Gln Lys Trp Glu Cys Glu Val Asp Gln Val Ser Gly
    50                  55                  60

Val Gln Lys Pro Val Cys Glu Ala Asp Gln Val Ser Gly Val Gln Lys
65                  70                  75                  80

Pro Gln Cys Glu Met Asp Gln Val Ser Gly Ile Gln Lys Leu Glu Cys
                85                  90                  95

Glu Ala Asp Gln Lys Trp Glu Tyr Glu Val Asp Gln Val Ser Gly Val
            100                 105                 110

Gln Lys Pro Gln Cys Glu Met Asp Gln Val Ser Gly Ile Gln Lys Leu
        115                 120                 125

Glu Cys Glu Ala Asp Gln Glu Cys Glu Thr Tyr Glu Lys Cys Cys Pro
    130                 135                 140

Asn Val Cys Gly Thr Lys Ser Cys Val Ala Ala Arg Tyr Met Asp Val
145                 150                 155                 160

Lys Gly Lys Lys Gly Pro Val Gly Met Pro Lys Glu Ala Thr Cys Asp
                165                 170                 175

His Phe Met Cys Leu Gln Gly Ser Glu Cys Asp Ile Trp Asp Gly
            180                 185                 190

Gln Pro Val Cys Lys Cys Lys Asp Arg Cys Glu Lys Glu Pro Ser Phe
        195                 200                 205

Thr Cys Ala Ser Asp Gly Leu Thr Tyr Tyr Asn Arg Cys Tyr Met Asp
    210                 215                 220

Ala Glu Ala Cys Ser Lys Gly Ile Thr Leu Ala Val Val Thr Cys Arg
225                 230                 235                 240

Tyr His Phe Thr Trp Pro Asn Thr Ser Pro Pro Pro Glu Thr Thr
                245                 250                 255

Met His Pro Thr Thr Ala Ser Pro Glu Thr Pro Glu Leu Asp Met Ala
            260                 265                 270
```

```
Ala Pro Ala Leu Leu Asn Asn Pro Val His Gln Ser Val Thr Met Gly
        275                 280                 285
Glu Thr Val Ser Phe Leu Cys Asp Val Val Gly Arg Pro Arg Pro Glu
    290                 295                 300
Ile Thr Trp Glu Lys Gln Leu Glu Asp Arg Glu Asn Val Val Met Arg
305                 310                 315                 320
Pro Asn His Val Arg Gly Asn Val Val Thr Asn Ile Ala Gln Leu
            325                 330                 335
Val Ile Tyr Asn Ala Gln Leu Gln Asp Ala Gly Ile Tyr Thr Cys Thr
        340                 345                 350
Ala Arg Asn Val Ala Gly Val Leu Arg Ala Asp Phe Pro Leu Ser Val
        355                 360                 365
Val Arg Gly His Gln Ala Ala Thr Ser Glu Ser Ser Pro Asn Gly
        370                 375                 380
Thr Ala Phe Pro Ala Ala Glu Cys Leu Lys Pro Pro Asp Ser Glu Asp
385                 390                 395                 400
Cys Gly Glu Glu Gln Thr Arg Trp His Phe Asp Ala Gln Ala Asn Asn
                405                 410                 415
Cys Leu Thr Phe Thr Phe Gly His Cys His Arg Asn Leu Asn His Phe
            420                 425                 430
Glu Thr Tyr Glu Ala Cys Met Leu Ala Cys Met Ser Gly Pro Leu Ala
        435                 440                 445
Ala Cys Ser Leu Pro Ala Leu Gln Gly Pro Cys Lys Ala Tyr Ala Pro
    450                 455                 460
Arg Trp Ala Tyr Asn Ser Gln Thr Gly Gln Cys Gln Ser Phe Val Tyr
465                 470                 475                 480
Gly Gly Cys Glu Gly Asn Gly Asn Asn Phe Glu Ser Arg Glu Ala Cys
                485                 490                 495
Glu Glu Ser Cys Pro Phe Pro Arg Gly Asn Gln Arg Cys Arg Ala Cys
            500                 505                 510
Lys Pro Arg Gln Lys Leu Val Thr Ser Phe Cys Arg Ser Asp Phe Val
        515                 520                 525
Ile Leu Gly Arg Val Ser Glu Leu Thr Glu Pro Asp Ser Gly Arg
        530                 535                 540
Ala Leu Val Thr Val Asp Glu Val Leu Lys Asp Glu Lys Met Gly Leu
545                 550                 555                 560
Lys Phe Leu Gly Gln Glu Pro Leu Glu Val Thr Leu Leu His Val Asp
                565                 570                 575
Trp Ala Cys Pro Cys Pro Asn Val Thr Val Ser Glu Met Pro Leu Ile
            580                 585                 590
Ile Met Gly Glu Val Asp Gly Gly Met Ala Met Leu Arg Pro Asp Ser
        595                 600                 605
Phe Val Gly Ala Ser Ser Ala Arg Arg Val Arg Lys Leu Arg Glu Val
    610                 615                 620
Met His Lys Lys Thr Cys Asp Val Leu Lys Glu Phe Leu Gly Leu His
625                 630                 635                 640

<210> SEQ ID NO 6
<211> LENGTH: 1731
<212> TYPE: DNA
<213> ORGANISM: Homo sapiens

<400> SEQUENCE: 6
atgtgggccc caaggtgtcg ccggttctgg tctcgctggg agcaggtggc agcgctgctg    60
```

-continued

```
ctgctgctgc tactgctcgg ggtgcccccg cgaagcctgg cgctgccgcc catccgctat    120
tcccacgccg gcatctgccc caacgacatg aatcccaacc tctgggtgga cgcacagagc    180
acctgcaggc gggagtgtga gacgaccag gagtgtgaga cctatgagaa gtgctgcccc     240
aacgtatgtg ggaccaagag ctgcgtggcg gcccgctaca tggacgtgaa agggaagaag    300
ggcccagtgg gcatgcccaa ggaggccaca tgtgaccact tcatgtgtct gcagcagggc    360
tctgagtgtg acatctggga tggccagccc gtgtgtaagt gcaaagaccg ctgtgagaag    420
gagcccagct ttacctgcgc ctcggacggc ctcacctact ataaccgctg ctacatggat    480
gccgaggcct gctccaaagg catcacactg gccgttgtaa cctgccgcta tcacttcacc    540
tggcccaaca ccagccccc accacctgag accaccatgc ccccaccac agcctcccca     600
gagacccctg agctggacat ggcggcccct gcgctgctca caaccctgt gcaccagtcg     660
gtcaccatgg gtgagacagt gagtttcctc tgtgatgtgg tgggccggcc ccggcctgag    720
atcacctggg agaagcagtt ggaggatcgg gagaatgtgg tcatgcggcc caaccatgtg    780
cgtggcaacg tggtggtcac caacattgcc cagctggtca tctataacgc ccagctgcag    840
gatgctggga tctacacctg cacggcccgg aacgtggctg ggtcctgag ggctgatttc      900
ccgctgtcgg tggtcagggg tcatcaggct gcagccacct cagagagcag ccccaatggc    960
acggctttcc cggcggccga gtgcctgaag cccccagaca gtgaggactg tggcgaagag    1020
cagacccgct ggcacttcga tcccaggcc aacaactgcc tgaccttcac cttcggccac     1080
tgccaccgta acctcaacca ctttgagacc tatgaggcct gcatgctggc ctgcatgagc    1140
gggccgctgg ccgcgtgcag cctgcccgcc ctgcaggggc cctgcaaagc ctacgcgcct    1200
cgctgggctt acaacagcca gacgggccag tgccagtcct ttgtctatgg tggctgcgag    1260
ggcaatggca caactttga gagccgtgag gcctgtgagg agtcgtgccc cttccccagg     1320
gggaaccagc gctgtcgggc ctgcaagcct cggcagaagc tcgttaccag cttctgtcgc    1380
agcgactttg tcatcctggg ccgagtctct gagctgaccg aggagcctga ctcgggccgc    1440
gccctggtga ctgtggatga ggtcctaaag gatgagaaaa tgggcctcaa gttcctgggc    1500
caggagccat tggaggtcac tctgcttcac gtggactggg catgccctg ccccaacgtg     1560
accgtgagcg agatgccgct catcatcatg gggaggtgg acggcggcat ggccatgctg    1620
cgccccgata gctttgtggg cgcatcgagt gcccgccggg tcaggaagct tcgtgaggtc    1680
atgcacaaga agacctgtga cgtcctcaag gagtttcttg gcttgcactg a            1731
```

<210> SEQ ID NO 7
<211> LENGTH: 576
<212> TYPE: PRT
<213> ORGANISM: Homo sapiens

<400> SEQUENCE: 7

```
Met Trp Ala Pro Arg Cys Arg Arg Phe Trp Ser Arg Trp Glu Gln Val
  1               5                  10                  15

Ala Ala Leu Leu Leu Leu Leu Leu Leu Gly Val Pro Pro Arg Ser
                 20                  25                  30

Leu Ala Leu Pro Pro Ile Arg Tyr Ser His Ala Gly Ile Cys Pro Asn
         35                  40                  45

Asp Met Asn Pro Asn Leu Trp Val Asp Ala Gln Ser Thr Cys Arg Arg
     50                  55                  60

Glu Cys Glu Thr Asp Gln Glu Cys Glu Thr Tyr Glu Lys Cys Cys Pro
 65                  70                  75                  80
```

-continued

```
Asn Val Cys Gly Thr Lys Ser Cys Val Ala Arg Tyr Met Asp Val
                 85                  90                  95
Lys Gly Lys Lys Gly Pro Val Gly Met Pro Lys Glu Ala Thr Cys Asp
            100                 105                 110
His Phe Met Cys Leu Gln Gln Gly Ser Glu Cys Asp Ile Trp Asp Gly
            115                 120                 125
Gln Pro Val Cys Lys Cys Lys Asp Arg Cys Glu Lys Glu Pro Ser Phe
130                 135                 140
Thr Cys Ala Ser Asp Gly Leu Thr Tyr Tyr Asn Arg Cys Tyr Met Asp
145                 150                 155                 160
Ala Glu Ala Cys Ser Lys Gly Ile Thr Leu Ala Val Val Thr Cys Arg
                165                 170                 175
Tyr His Phe Thr Trp Pro Asn Thr Ser Pro Pro Pro Glu Thr Thr
                180                 185                 190
Met His Pro Thr Thr Ala Ser Pro Glu Thr Pro Glu Leu Asp Met Ala
            195                 200                 205
Ala Pro Ala Leu Leu Asn Asn Pro Val His Gln Ser Val Thr Met Gly
210                 215                 220
Glu Thr Val Ser Phe Leu Cys Asp Val Val Gly Arg Pro Arg Pro Glu
225                 230                 235                 240
Ile Thr Trp Glu Lys Gln Leu Glu Asp Arg Glu Asn Val Val Met Arg
                245                 250                 255
Pro Asn His Val Arg Gly Asn Val Val Thr Asn Ile Ala Gln Leu
            260                 265                 270
Val Ile Tyr Asn Ala Gln Leu Gln Asp Ala Gly Ile Tyr Thr Cys Thr
            275                 280                 285
Ala Arg Asn Val Ala Gly Val Leu Arg Ala Asp Phe Pro Leu Ser Val
290                 295                 300
Val Arg Gly His Gln Ala Ala Thr Ser Glu Ser Ser Pro Asn Gly
305                 310                 315                 320
Thr Ala Phe Pro Ala Ala Glu Cys Leu Lys Pro Pro Asp Ser Glu Asp
                325                 330                 335
Cys Gly Glu Glu Gln Thr Arg Trp His Phe Asp Ala Gln Ala Asn Asn
            340                 345                 350
Cys Leu Thr Phe Thr Phe Gly His Cys His Arg Asn Leu Asn His Phe
            355                 360                 365
Glu Thr Tyr Glu Ala Cys Met Leu Ala Cys Met Ser Gly Pro Leu Ala
        370                 375                 380
Ala Cys Ser Leu Pro Ala Leu Gln Gly Pro Cys Lys Ala Tyr Ala Pro
385                 390                 395                 400
Arg Trp Ala Tyr Asn Ser Gln Thr Gly Gln Cys Gln Ser Phe Val Tyr
                405                 410                 415
Gly Gly Cys Glu Gly Asn Gly Asn Asn Phe Glu Ser Arg Glu Ala Cys
            420                 425                 430
Glu Glu Ser Cys Pro Phe Pro Arg Gly Asn Gln Arg Cys Arg Ala Cys
            435                 440                 445
Lys Pro Arg Gln Lys Leu Val Thr Ser Phe Cys Arg Ser Asp Phe Val
450                 455                 460
Ile Leu Gly Arg Val Ser Glu Leu Thr Glu Pro Asp Ser Gly Arg
465                 470                 475                 480
Ala Leu Val Thr Val Asp Glu Val Leu Lys Asp Glu Lys Met Gly Leu
                485                 490                 495
Lys Phe Leu Gly Gln Glu Pro Leu Glu Val Thr Leu Leu His Val Asp
```

|         |         |         |
|---------|---------|---------|
|         | 500     | 505     | 510     |
| Trp Ala Cys Pro Cys Pro Asn Val Thr Val Ser Glu Met Pro Leu Ile |
|         | 515     |         | 520     |         | 525     |
| Ile Met Gly Glu Val Asp Gly Gly Met Ala Met Leu Arg Pro Asp Ser |
|         | 530     |         | 535     |         | 540     |
| Phe Val Gly Ala Ser Ser Ala Arg Arg Val Arg Lys Leu Arg Glu Val |
| 545     |         | 550     |         | 555     |         | 560     |
| Met His Lys Lys Thr Cys Asp Val Leu Lys Glu Phe Leu Gly Leu His |
|         |         | 565     |         | 570     |         | 575     |

<210> SEQ ID NO 8
<211> LENGTH: 1659
<212> TYPE: DNA
<213> ORGANISM: Mus sp.

<400> SEQUENCE: 8

| atgcctgccc cacagccatt cctgcctctg ctctttgtct tcgtgctcat ccatctgacc | 60 |
| tcggagacca acctgctgcc agatcccgga agccatcctg gcatgtgccc aacgagctc | 120 |
| agcccccacc tgtgggtcga cgcccagagc acctgtgagc gtgagtgtac cggggaccag | 180 |
| gactgtgcgg catccgagaa gtgctgcacc aatgtgtgtg gctgcagag ctgcgtggct | 240 |
| gcccgctttc ccagtggtgg cccagctgta cctgagacag cagcctcctg tgaaggcttc | 300 |
| caatgcccac aacagggttc tgactgtgac atctgggatg gcagccagt ttgtcgctgc | 360 |
| cgtgaccgct gtgaaaaaga acccagcttc acatgtgctt ctgatggcct tacctattac | 420 |
| aaccgctgct acatggacgc agaagcctgc ctgcgggtc tccacctgca cgttgtaccc | 480 |
| tgtaagcaca ttctcagttg gccgcccagc agcccgggac acccgagac cactgctcgc | 540 |
| ccaaccctg gggctgctcc catgccacct gccctgtaca cagcccctc accacaggca | 600 |
| gtgcatgttg ggggacagc cagcctccac tgtgatgtta gtggccgtcc accacctgct | 660 |
| gtgacctggg agaagcagag ccatcagcgg gagaacctga tcatgcgccc tgaccaaatg | 720 |
| tatggcaacg tggttgtcac cagtatcgga cagctagtcc tctacaatgc tcagttggag | 780 |
| gatgcgggcc tgtatacctg cactgcacga aacgctgccg gcctgctgcg ggccgacttt | 840 |
| ccccttccg tttacagcg ggcaactact caggacaggg acccaggtat cccagccttg | 900 |
| gctgagtgcc aggccgacac acaagcctgt gttgggccac ctactcccca tcatgtcctt | 960 |
| tggcgctttg acccagagag aggcagctgc atgacattcc cagccctcag atgtgatggg | 1020 |
| gctgcccggg gctttgagac ctatgaggca tgccagcagg cctgtgttcg tggccccggg | 1080 |
| gatgtctgtg cactgcctgc agttcagggg ccctgccagg gctggagcc acgctgggcc | 1140 |
| tacagcccac tgctacagca gtgccacccc tttgtataca gtggctgtga aggaaacagc | 1200 |
| aataactttg agacccggga gagctgtgag gatgcttgcc ctgtaccacg cacaccaccc | 1260 |
| tgtcgtgcct gccgcctcaa gagcaagctg gctctgagct tgtgccgcag tgactttgcc | 1320 |
| atcgtgggga gactcacaga ggtcctggag gagcccgagg ctgcaggcgg catagctcgt | 1380 |
| gtggccttgg atgatgtgct aaaggacgac aagatgggcc tcaagttctt gggcaccaaa | 1440 |
| tacctggagg tgacattgag tggcatggac tgggcctgcc catgccccaa cgtgacagct | 1500 |
| gtcgatgggc cactggtcat catggtgag gttcgtgaag gtgtggctgt gttggacgcc | 1560 |
| aacagctatg tccgtgctgc cagcgagaag cgagtcaaga agattgtgga actgctcgag | 1620 |
| aagaaggctt gtgaactgct caaccgcttc caagactag | 1659 |

```
<210> SEQ ID NO 9
<211> LENGTH: 552
<212> TYPE: PRT
<213> ORGANISM: Mus sp.

<400> SEQUENCE: 9

Met Pro Ala Pro Gln Pro Phe Leu Pro Leu Leu Phe Val Phe Val Leu
  1               5                  10                  15

Ile His Leu Thr Ser Glu Thr Asn Leu Leu Pro Asp Pro Gly Ser His
             20                  25                  30

Pro Gly Met Cys Pro Asn Glu Leu Ser Pro His Leu Trp Val Asp Ala
         35                  40                  45

Gln Ser Thr Cys Glu Arg Glu Cys Thr Gly Asp Gln Asp Cys Ala Ala
     50                  55                  60

Ser Glu Lys Cys Cys Thr Asn Val Cys Gly Leu Gln Ser Cys Val Ala
 65                  70                  75                  80

Ala Arg Phe Pro Ser Gly Gly Pro Ala Val Pro Glu Thr Ala Ala Ser
                 85                  90                  95

Cys Glu Gly Phe Gln Cys Pro Gln Gln Gly Ser Asp Cys Asp Ile Trp
            100                 105                 110

Asp Gly Gln Pro Val Cys Arg Cys Arg Asp Arg Cys Glu Lys Glu Pro
            115                 120                 125

Ser Phe Thr Cys Ala Ser Asp Gly Leu Thr Tyr Tyr Asn Arg Cys Tyr
        130                 135                 140

Met Asp Ala Glu Ala Cys Leu Arg Gly Leu His Leu His Val Val Pro
145                 150                 155                 160

Cys Lys His Ile Leu Ser Trp Pro Pro Ser Ser Pro Gly Pro Pro Glu
                165                 170                 175

Thr Thr Ala Arg Pro Thr Pro Gly Ala Ala Pro Met Pro Pro Ala Leu
            180                 185                 190

Tyr Asn Ser Pro Ser Pro Gln Ala Val His Val Gly Gly Thr Ala Ser
        195                 200                 205

Leu His Cys Asp Val Ser Gly Arg Pro Pro Pro Ala Val Thr Trp Glu
    210                 215                 220

Lys Gln Ser His Gln Arg Glu Asn Leu Ile Met Arg Pro Asp Gln Met
225                 230                 235                 240

Tyr Gly Asn Val Val Thr Ser Ile Gly Gln Leu Val Leu Tyr Asn
                245                 250                 255

Ala Gln Leu Glu Asp Ala Gly Leu Tyr Thr Cys Thr Ala Arg Asn Ala
            260                 265                 270

Ala Gly Leu Leu Arg Ala Asp Phe Pro Leu Ser Val Leu Gln Arg Ala
        275                 280                 285

Thr Thr Gln Asp Arg Asp Pro Gly Ile Pro Ala Leu Ala Glu Cys Gln
    290                 295                 300

Ala Asp Thr Gln Ala Cys Val Gly Pro Thr Pro His His Val Leu
305                 310                 315                 320

Trp Arg Phe Asp Pro Gln Arg Gly Ser Cys Met Thr Phe Pro Ala Leu
                325                 330                 335

Arg Cys Asp Gly Ala Ala Arg Gly Phe Glu Thr Tyr Glu Ala Cys Gln
            340                 345                 350

Gln Ala Cys Val Arg Gly Pro Gly Asp Val Cys Ala Leu Pro Ala Val
        355                 360                 365

Gln Gly Pro Cys Gln Gly Trp Glu Pro Arg Trp Ala Tyr Ser Pro Leu
    370                 375                 380
```

| | | | | | | | | | | | | | | |
|---|---|---|---|---|---|---|---|---|---|---|---|---|---|---|
|Leu|Gln|Gln|Cys|His|Pro|Phe|Val|Tyr|Ser|Gly|Cys|Glu|Gly|Asn|Ser|
|385| | | | |390| | | | |395| | | | |400|

| | | | | | | | | | | | | |
|---|---|---|---|---|---|---|---|---|---|---|---|---|
|Asn|Asn|Phe|Glu|Thr|Arg|Glu|Ser|Cys|Glu|Asp|Ala|Cys|Pro|Val|Pro|
| | | | |405| | | | |410| | | | |415| |

Arg Thr Pro Pro Cys Arg Ala Cys Arg Leu Lys Ser Lys Leu Ala Leu
            420                 425                 430

Ser Leu Cys Arg Ser Asp Phe Ala Ile Val Gly Arg Leu Thr Glu Val
        435                 440                 445

Leu Glu Glu Pro Glu Ala Ala Gly Gly Ile Ala Arg Val Ala Leu Asp
    450                 455                 460

Asp Val Leu Lys Asp Asp Lys Met Gly Leu Lys Phe Leu Gly Thr Lys
465                 470                 475                 480

Tyr Leu Glu Val Thr Leu Ser Gly Met Asp Trp Ala Cys Pro Cys Pro
                485                 490                 495

Asn Val Thr Ala Val Asp Gly Pro Leu Val Ile Met Gly Glu Val Arg
            500                 505                 510

Glu Gly Val Ala Val Leu Asp Ala Asn Ser Tyr Val Arg Ala Ala Ser
        515                 520                 525

Glu Lys Arg Val Lys Lys Ile Val Glu Leu Leu Glu Lys Lys Ala Cys
    530                 535                 540

Glu Leu Leu Asn Arg Phe Gln Asp
545                 550

<210> SEQ ID NO 10
<211> LENGTH: 1695
<212> TYPE: DNA
<213> ORGANISM: Homo sapiens

<400> SEQUENCE: 10

```
atgcccgccc tacgtccact cctgccgctc ctgctcctcc tccggctgac ctcgggggct      60
ggcttgctgc agggctggg gagccacccg ggcgtgtgcc ccaaccagct cagccccaac     120
ctgtgggtgg acgcccagag cacctgtgag cgcgagtgta gcaggacca ggactgtgcg     180
gctgctgaga gtgctgcat caacgtgtgt ggactgcaca gctgcgtggc agcacgcttc     240
cccggcagcc cagctgcgcc gacgacagcg gcctcctgcg agggctttgt gtgcccacag     300
cagggctcgg actgcgacat ctgggacggg cagcccgtgt gccgctgccg cgaccgctgt     360
gagaaggagc ccagcttcac ctgcgcctcg gacggcctca cctactacaa ccgctgctat     420
atggacgccg aggcctgcct gcggggcctg cacctccaca tcgtgccctg caagcacgtg     480
ctcagctggc cgcccagcag cccggggccg ccggagacca ctgcccgccc cacacctggg     540
gccgcgcccg tgcctcctgc cctgtacagc agcccctccc cacaggcggt gcaggttggg     600
ggtacggcca gcctccactg cgacgtcagc ggccgcccgc cgcctgctgt gacctgggag     660
aagcagagtc accagcgaga gaacctgatc atgcgccctg atcagatgta tggcaacgtg     720
gtggtcacca gcatcgggca gctggtgctc tacaacgcgc ggcccgaaga cgccggcctg     780
tacacctgca ccgcgcgcaa cgctgctggg ctgctgcggg ctgacttccc actctctgtg     840
gtccagcgag agccggccag ggacgcagcc ccagcatcc cagccccggc cgagtgcctg     900
ccggatgtgc aggcctgcac gggcccacact tccccacacc ttgtcctctg cactacgac     960
ccgcagcggg gcggctgcat gaccttcccg gccgtggct gtgatgggc ggcccgcggc    1020
tttgagacct acgaggcatg ccagcaggcc tgtgcccgcg ccccggcga cgcctgcgtg    1080
ctgcctgccg tgcagggccc ctgccggggc tgggagccgc gctgggccta cagcccgctg    1140
```

-continued

```
ctgcagcagt gccatccctt cgtgtacggt ggctgcgagg gcaacggcaa caacttccac      1200
agccgcgaga gctgcgagga tgcctgcccc gtgccgcgca ccgccctg ccgcgcctgc       1260 cgcctccgga gcaagctggc gctgagcctg tgccgcagcg acttcgccat cgtggggcgg      1320
ctcacggagg tgctggagga gcccgaggcc gccggcggca tcgcccgcgt ggcgctcgag      1380
gacgtgctca aggatgacaa gatgggcctc aagttcttgg gcaccaagta cctggaggtg      1440
acgctgagtg gcatggactg gcctgcccc tgccccaaca tgacggcggg cgacgggccg       1500
ctggtcatca tgggtgaggt gcgcgatggc gtggccgtgc tggacgccgg cagctacgtc      1560
cgcgccgcca gcgagaagcg cgtcaagaag atcttggagc tgctggagaa gcaggcctgc      1620
gagctgctca accgcttcca ggactagccc ccgcaggggc ctgcgccacc ccgtcctggt      1680
gaataaacgc actcc                                                      1695
```

<210> SEQ ID NO 11
<211> LENGTH: 548
<212> TYPE: PRT
<213> ORGANISM: Homo sapiens

<400> SEQUENCE: 11

```
Met Pro Ala Leu Arg Pro Leu Pro Leu Leu Leu Leu Leu Leu Arg Leu
 1               5                  10                  15

Thr Ser Gly Ala Gly Leu Leu Pro Gly Leu Gly Ser His Pro Gly Val
            20                  25                  30

Cys Pro Asn Gln Leu Ser Pro Asn Leu Trp Val Asp Ala Gln Ser Thr
        35                  40                  45

Cys Glu Arg Glu Cys Ser Arg Asp Gln Asp Cys Ala Ala Ala Glu Lys
    50                  55                  60

Cys Cys Ile Asn Val Cys Gly Leu His Ser Cys Val Ala Ala Arg Phe
65                  70                  75                  80

Pro Gly Ser Pro Ala Ala Pro Thr Thr Ala Ala Ser Cys Glu Gly Phe
                85                  90                  95

Val Cys Pro Gln Gln Gly Ser Asp Cys Asp Ile Trp Asp Gly Gln Pro
            100                 105                 110

Val Cys Arg Cys Arg Asp Arg Cys Glu Lys Glu Pro Ser Phe Thr Cys
        115                 120                 125

Ala Ser Asp Gly Leu Thr Tyr Tyr Asn Arg Cys Tyr Met Asp Ala Glu
    130                 135                 140

Ala Cys Leu Arg Gly Leu His Leu His Ile Val Pro Cys Lys His Val
145                 150                 155                 160

Leu Ser Trp Pro Pro Ser Ser Pro Gly Pro Pro Glu Thr Thr Ala Arg
                165                 170                 175

Pro Thr Pro Gly Ala Ala Pro Val Pro Pro Ala Leu Tyr Ser Ser Pro
            180                 185                 190

Ser Pro Gln Ala Val Gln Val Gly Gly Thr Ala Ser Leu His Cys Asp
        195                 200                 205

Val Ser Gly Arg Pro Pro Pro Ala Val Thr Trp Glu Lys Gln Ser His
    210                 215                 220

Gln Arg Glu Asn Leu Ile Met Arg Pro Asp Gln Met Tyr Gly Asn Val
225                 230                 235                 240

Val Val Thr Ser Ile Gly Gln Leu Val Leu Tyr Asn Ala Arg Pro Glu
                245                 250                 255

Asp Ala Gly Leu Tyr Thr Cys Thr Ala Arg Asn Ala Ala Gly Leu Leu
            260                 265                 270
```

-continued

```
Arg Ala Asp Phe Pro Leu Ser Val Val Gln Arg Glu Pro Ala Arg Asp
        275                 280                 285

Ala Ala Pro Ser Ile Pro Ala Pro Ala Glu Cys Leu Pro Asp Val Gln
    290                 295                 300

Ala Cys Thr Gly Pro Thr Ser Pro His Leu Val Leu Trp His Tyr Asp
305                 310                 315                 320

Pro Gln Arg Gly Gly Cys Met Thr Phe Pro Arg Gly Cys Asp Gly
                325                 330                 335

Ala Ala Arg Gly Phe Glu Thr Tyr Glu Ala Cys Gln Gln Ala Cys Ala
                340                 345                 350

Arg Gly Pro Gly Asp Ala Cys Val Leu Pro Ala Val Gln Gly Pro Cys
            355                 360                 365

Arg Gly Trp Glu Pro Arg Trp Ala Tyr Ser Pro Leu Leu Gln Gln Cys
        370                 375                 380

His Pro Phe Val Tyr Gly Gly Cys Glu Gly Asn Gly Asn Asn Phe His
385                 390                 395                 400

Ser Arg Glu Ser Cys Glu Asp Ala Cys Pro Val Arg Thr Pro Pro
            405                 410                 415

Cys Arg Ala Cys Arg Leu Arg Ser Lys Leu Ala Leu Ser Leu Cys Arg
                420                 425                 430

Ser Asp Phe Ala Ile Val Gly Arg Leu Thr Glu Val Leu Glu Glu Pro
            435                 440                 445

Glu Ala Ala Gly Gly Ile Ala Arg Val Ala Leu Glu Asp Val Leu Lys
    450                 455                 460

Asp Asp Lys Met Gly Leu Lys Phe Leu Gly Thr Lys Tyr Leu Glu Val
465                 470                 475                 480

Thr Leu Ser Gly Met Asp Trp Ala Cys Pro Cys Pro Asn Met Thr Ala
                485                 490                 495

Gly Asp Gly Pro Leu Val Ile Met Gly Glu Val Arg Asp Gly Val Ala
                500                 505                 510

Val Leu Asp Ala Gly Ser Tyr Val Arg Ala Ala Ser Glu Lys Arg Val
            515                 520                 525

Lys Lys Ile Leu Glu Leu Leu Glu Lys Gln Ala Cys Glu Leu Leu Asn
    530                 535                 540

Arg Phe Gln Asp
545
```

<210> SEQ ID NO 12
<211> LENGTH: 30
<212> TYPE: PRT
<213> ORGANISM: Artificial Sequence
<220> FEATURE:
<223> OTHER INFORMATION: Description of Artificial Sequence:
      Illustrative competing peptide

<400> SEQUENCE: 12

```
Asp Phe Gly Leu Asp Ser Asp Glu His Ser Thr Glu Ser Arg Ser Ser
 1               5                  10                  15

Arg Tyr Pro Leu Thr Val Asp Phe Glu Ala Phe Gly Trp Asp
            20                  25                  30
```

<210> SEQ ID NO 13
<211> LENGTH: 15
<212> TYPE: PRT
<213> ORGANISM: Mus sp.

<400> SEQUENCE: 13

Ala Asn Tyr Cys Ser Gly Glu Cys Glu Phe Val Phe Leu Gln Lys
1               5                   10                  15

<210> SEQ ID NO 14
<211> LENGTH: 12
<212> TYPE: PRT
<213> ORGANISM: Mus sp.

<400> SEQUENCE: 14

Met Ser Pro Ile Asn Met Leu Tyr Phe Asn Gly Lys
1               5                   10

<210> SEQ ID NO 15
<211> LENGTH: 14
<212> TYPE: PRT
<213> ORGANISM: Mus sp.

<400> SEQUENCE: 15

Asp Phe Gly Leu Asp Cys Asp Glu His Ser Thr Glu Ser Arg
1               5                   10

<210> SEQ ID NO 16
<211> LENGTH: 15
<212> TYPE: PRT
<213> ORGANISM: Mus sp.

<400> SEQUENCE: 16

Ala Asn Tyr Cys Ser Gly Glu Cys Glu Phe Val Phe Leu Gln Lys
1               5                   10                  15

<210> SEQ ID NO 17
<211> LENGTH: 12
<212> TYPE: PRT
<213> ORGANISM: Mus sp.

<400> SEQUENCE: 17

Met Ser Pro Ile Asn Met Leu Tyr Phe Asn Gly Lys
1               5                   10

<210> SEQ ID NO 18
<211> LENGTH: 19
<212> TYPE: PRT
<213> ORGANISM: Mus sp.

<400> SEQUENCE: 18

Tyr Pro Leu Thr Val Asp Phe Glu Ala Phe Gly Trp Asp Trp Ile Ile
1               5                   10                  15

Ala Pro Lys

<210> SEQ ID NO 19
<211> LENGTH: 12
<212> TYPE: PRT
<213> ORGANISM: Mus sp.

<400> SEQUENCE: 19

Met Ser Pro Ile Asn Met Leu Tyr Phe Asn Gly Lys
1               5                   10

<210> SEQ ID NO 20
<211> LENGTH: 11
<212> TYPE: PRT
<213> ORGANISM: Mus sp.

<400> SEQUENCE: 20

```
Gly Ser Ala Gly Pro Cys Cys Thr Pro Thr Lys
  1               5                  10
```

<210> SEQ ID NO 21
<211> LENGTH: 16
<212> TYPE: PRT
<213> ORGANISM: Mus sp.

<400> SEQUENCE: 21

```
Leu Asp Met Ser Pro Gly Thr Gly Ile Trp Gln Ser Ile Asp Val Lys
  1               5                  10                  15
```

<210> SEQ ID NO 22
<211> LENGTH: 28
<212> TYPE: PRT
<213> ORGANISM: Mus sp.

<400> SEQUENCE: 22

```
Ala Leu Asp Glu Asn Gly His Asp Leu Ala Val Thr Phe Pro Gly Pro
  1               5                  10                  15

Gly Glu Asp Gly Leu Asn Pro Phe Leu Glu Val Lys
              20                  25
```

<210> SEQ ID NO 23
<211> LENGTH: 16
<212> TYPE: PRT
<213> ORGANISM: Mus sp.

<400> SEQUENCE: 23

```
Leu Asp Met Ser Pro Gly Thr Gly Ile Trp Gln Ser Ile Asp Val Lys
  1               5                  10                  15
```

<210> SEQ ID NO 24
<211> LENGTH: 10
<212> TYPE: PRT
<213> ORGANISM: Mus sp.

<400> SEQUENCE: 24

```
Glu Leu Ile Asp Gln Tyr Asp Val Gln Arg
  1               5                  10
```

<210> SEQ ID NO 25
<211> LENGTH: 11
<212> TYPE: PRT
<213> ORGANISM: Mus sp.

<400> SEQUENCE: 25

```
Thr Pro Thr Thr Val Phe Val Gln Ile Leu Arg
  1               5                  10
```

<210> SEQ ID NO 26
<211> LENGTH: 11
<212> TYPE: PRT
<213> ORGANISM: Mus sp.

<400> SEQUENCE: 26

```
Ala Gln Leu Trp Ile Tyr Leu Arg Pro Val Lys
  1               5                  10
```

<210> SEQ ID NO 27
<211> LENGTH: 10
<212> TYPE: PRT
<213> ORGANISM: Mus sp.

<400> SEQUENCE: 27

```
Glu Gly Leu Cys Asn Ala Cys Ala Trp Arg
  1               5                  10
```

<210> SEQ ID NO 28
<211> LENGTH: 18
<212> TYPE: PRT
<213> ORGANISM: Mus sp.

<400> SEQUENCE: 28

```
Pro Gln Ser Cys Leu Val Asp Gln Thr Gly Ser Ala His Cys Val Val
  1               5                  10                  15

Cys Arg
```

<210> SEQ ID NO 29
<211> LENGTH: 12
<212> TYPE: PRT
<213> ORGANISM: Mus sp.

<400> SEQUENCE: 29

```
Asp Ser Cys Asp Gly Val Glu Cys Gly Pro Gly Lys
  1               5                  10
```

<210> SEQ ID NO 30
<211> LENGTH: 9
<212> TYPE: PRT
<213> ORGANISM: Mus sp.

<400> SEQUENCE: 30

```
Ser Cys Ala Gln Val Val Cys Pro Arg
  1               5
```

<210> SEQ ID NO 31
<211> LENGTH: 13
<212> TYPE: PRT
<213> ORGANISM: Mus sp.

<400> SEQUENCE: 31

```
Glu Cys Glu Thr Asp Gln Glu Cys Glu Thr Tyr Glu Lys
  1               5                  10
```

<210> SEQ ID NO 32
<211> LENGTH: 9
<212> TYPE: PRT
<213> ORGANISM: Mus sp.

<400> SEQUENCE: 32

```
Ala Asp Phe Pro Leu Ser Val Val Arg
  1               5
```

<210> SEQ ID NO 33
<211> LENGTH: 11
<212> TYPE: PRT
<213> ORGANISM: Mus sp.

<400> SEQUENCE: 33

```
Glu Ala Cys Glu Glu Ser Cys Pro Phe Pro Arg
  1               5                  10
```

<210> SEQ ID NO 34
<211> LENGTH: 8
<212> TYPE: PRT
<213> ORGANISM: Mus sp.

<400> SEQUENCE: 34

-continued

Ser Asp Phe Val Ile Leu Gly Arg
 1               5

<210> SEQ ID NO 35
<211> LENGTH: 12
<212> TYPE: PRT
<213> ORGANISM: Mus sp.

<400> SEQUENCE: 35

Val Ser Glu Leu Thr Glu Glu Gln Asp Ser Gly Arg
 1               5                  10

<210> SEQ ID NO 36
<211> LENGTH: 15
<212> TYPE: PRT
<213> ORGANISM: Homo sapiens

<400> SEQUENCE: 36

Ala Asn Tyr Cys Ser Gly Glu Cys Glu Phe Val Phe Leu Gln Lys
 1               5                  10                  15

<210> SEQ ID NO 37
<211> LENGTH: 14
<212> TYPE: PRT
<213> ORGANISM: Homo sapiens

<400> SEQUENCE: 37

Asp Phe Gly Leu Asp Cys Asp Glu His Ser Thr Glu Ser Arg
 1               5                  10

<210> SEQ ID NO 38
<211> LENGTH: 28
<212> TYPE: PRT
<213> ORGANISM: Homo sapiens

<400> SEQUENCE: 38

Ala Leu Asp Glu Asn Gly His Asp Leu Ala Val Thr Phe Pro Gly Pro
 1               5                  10                  15

Gly Glu Asp Gly Leu Asn Pro Phe Leu Glu Val Lys
            20                  25

<210> SEQ ID NO 39
<211> LENGTH: 10
<212> TYPE: PRT
<213> ORGANISM: Homo sapiens

<400> SEQUENCE: 39

Glu Leu Ile Asp Gln Tyr Asp Val Gln Arg
 1               5                  10

<210> SEQ ID NO 40
<211> LENGTH: 18
<212> TYPE: PRT
<213> ORGANISM: Homo sapiens

<400> SEQUENCE: 40

Pro Gln Ser Cys Val Val Asp Gln Thr Gly Ser Ala His Cys Val Val
 1               5                  10                  15

Cys Arg

<210> SEQ ID NO 41
<211> LENGTH: 13
<212> TYPE: PRT

<213> ORGANISM: Homo sapiens

<400> SEQUENCE: 41

Cys Glu Cys Ala Pro Asp Cys Ser Gly Leu Pro Ala Arg
 1               5                  10

<210> SEQ ID NO 42
<211> LENGTH: 12
<212> TYPE: PRT
<213> ORGANISM: Homo sapiens

<400> SEQUENCE: 42

Leu Gln Val Cys Gly Ser Asp Gly Ala Thr Tyr Arg
 1               5                  10

<210> SEQ ID NO 43
<211> LENGTH: 12
<212> TYPE: PRT
<213> ORGANISM: Homo sapiens

<400> SEQUENCE: 43

Val Ser Glu Leu Thr Glu Glu Pro Asp Ser Gly Arg
 1               5                  10

<210> SEQ ID NO 44
<211> LENGTH: 10
<212> TYPE: PRT
<213> ORGANISM: Homo sapiens

<400> SEQUENCE: 44

Cys Tyr Met Asp Ala Glu Ala Cys Ser Lys
 1               5                  10

<210> SEQ ID NO 45
<211> LENGTH: 10
<212> TYPE: PRT
<213> ORGANISM: Homo sapiens

<400> SEQUENCE: 45

Gly Ile Thr Leu Ala Val Val Thr Cys Arg
 1               5                  10

<210> SEQ ID NO 46
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 46
ttggccactg ccaccacaat ctcaaccact t                               31

<210> SEQ ID NO 47
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 47
tctcagcatg gccatgccgc cgtcga                                     26

<210> SEQ ID NO 48
<211> LENGTH: 1716
<212> TYPE: DNA

<213> ORGANISM: Mus sp.
<220> FEATURE:
<221> NAME/KEY: CDS
<222> LOCATION: (1)..(1713)

<400> SEQUENCE: 48

| | | | | | | | | | | | | | | | | |
|---|---|---|---|---|---|---|---|---|---|---|---|---|---|---|---|---|
| atg | tgt | gcc | cca | ggg | tat | cat | cgg | ttc | tgg | ttt | cac | tgg | ggg | ctg | ctg | 48 |
| Met | Cys | Ala | Pro | Gly | Tyr | His | Arg | Phe | Trp | Phe | His | Trp | Gly | Leu | Leu | |
| 1 | | | | 5 | | | | | 10 | | | | | 15 | | |
| ttg | ctg | ctg | ctc | ctc | gag | gct | ccc | ctt | cga | ggc | cta | gca | ctg | cca | ccc | 96 |
| Leu | Leu | Leu | Leu | Leu | Glu | Ala | Pro | Leu | Arg | Gly | Leu | Ala | Leu | Pro | Pro | |
| | | | | 20 | | | | | 25 | | | | | 30 | | |
| atc | cga | tac | tcc | cat | gcg | ggc | atc | tgc | ccc | aac | gac | atg | aac | ccc | aac | 144 |
| Ile | Arg | Tyr | Ser | His | Ala | Gly | Ile | Cys | Pro | Asn | Asp | Met | Asn | Pro | Asn | |
| | | | 35 | | | | | 40 | | | | | 45 | | | |
| ctc | tgg | gtg | gat | gcc | cag | agc | acc | tgc | aag | cga | gag | tgt | gaa | aca | gac | 192 |
| Leu | Trp | Val | Asp | Ala | Gln | Ser | Thr | Cys | Lys | Arg | Glu | Cys | Glu | Thr | Asp | |
| | 50 | | | | | 55 | | | | | 60 | | | | | |
| cag | gaa | tgt | gag | acc | tat | gag | aaa | tgc | tgc | ccc | aat | gtg | tgt | ggg | acc | 240 |
| Gln | Glu | Cys | Glu | Thr | Tyr | Glu | Lys | Cys | Cys | Pro | Asn | Val | Cys | Gly | Thr | |
| 65 | | | | | 70 | | | | | 75 | | | | | 80 | |
| aag | agc | tgt | gtg | gca | gcc | cgc | tac | atg | gat | gtg | aaa | ggg | aag | aag | ggg | 288 |
| Lys | Ser | Cys | Val | Ala | Ala | Arg | Tyr | Met | Asp | Val | Lys | Gly | Lys | Lys | Gly | |
| | | | | 85 | | | | | 90 | | | | | 95 | | |
| cct | gta | ggc | atg | ccc | aag | gag | gcc | aca | tgt | gac | cat | ttc | atg | tgc | ctg | 336 |
| Pro | Val | Gly | Met | Pro | Lys | Glu | Ala | Thr | Cys | Asp | His | Phe | Met | Cys | Leu | |
| | | | 100 | | | | | 105 | | | | | 110 | | | |
| cag | cag | ggc | tct | gag | tgt | gac | atc | tgg | gac | ggc | cag | ccc | gtg | tgt | aag | 384 |
| Gln | Gln | Gly | Ser | Glu | Cys | Asp | Ile | Trp | Asp | Gly | Gln | Pro | Val | Cys | Lys | |
| | | 115 | | | | | 120 | | | | | 125 | | | | |
| tgc | aaa | gat | cgc | tgt | gag | aag | gag | ccc | agc | ttc | acc | tgt | gcc | tct | gat | 432 |
| Cys | Lys | Asp | Arg | Cys | Glu | Lys | Glu | Pro | Ser | Phe | Thr | Cys | Ala | Ser | Asp | |
| | 130 | | | | | 135 | | | | | 140 | | | | | |
| ggc | ctt | acc | tac | tac | aac | cgt | tgc | ttc | atg | gac | gcc | gaa | gcc | tgc | tcc | 480 |
| Gly | Leu | Thr | Tyr | Tyr | Asn | Arg | Cys | Phe | Met | Asp | Ala | Glu | Ala | Cys | Ser | |
| 145 | | | | | 150 | | | | | 155 | | | | | 160 | |
| aag | ggc | atc | aca | ctg | tct | gtg | gtc | acc | tgt | cgt | tat | cac | ttc | acc | tgg | 528 |
| Lys | Gly | Ile | Thr | Leu | Ser | Val | Val | Thr | Cys | Arg | Tyr | His | Phe | Thr | Trp | |
| | | | | 165 | | | | | 170 | | | | | 175 | | |
| cct | aac | acc | agc | cct | cca | ccg | cct | gag | acc | acg | gtg | cat | ccc | acc | acc | 576 |
| Pro | Asn | Thr | Ser | Pro | Pro | Pro | Pro | Glu | Thr | Thr | Val | His | Pro | Thr | Thr | |
| | | | 180 | | | | | 185 | | | | | 190 | | | |
| gcc | tct | ccg | gag | act | ctc | ggg | ctg | gac | atg | gca | gcc | cca | gcc | ctg | ctc | 624 |
| Ala | Ser | Pro | Glu | Thr | Leu | Gly | Leu | Asp | Met | Ala | Ala | Pro | Ala | Leu | Leu | |
| | | 195 | | | | | 200 | | | | | 205 | | | | |
| aac | cac | cct | gtc | cat | cag | tca | gtc | acc | gtg | ggt | gag | act | gtg | agt | ttc | 672 |
| Asn | His | Pro | Val | His | Gln | Ser | Val | Thr | Val | Gly | Glu | Thr | Val | Ser | Phe | |
| | 210 | | | | | 215 | | | | | 220 | | | | | |
| ctc | tgt | gac | gtg | gta | ggc | cgg | cct | cgg | cca | gag | ctc | act | tgg | gag | aaa | 720 |
| Leu | Cys | Asp | Val | Val | Gly | Arg | Pro | Arg | Pro | Glu | Leu | Thr | Trp | Glu | Lys | |
| 225 | | | | | 230 | | | | | 235 | | | | | 240 | |
| cag | ctg | gag | gac | cga | gag | aat | gtt | gtc | atg | agg | ccc | aac | cac | gtg | cgt | 768 |
| Gln | Leu | Glu | Asp | Arg | Glu | Asn | Val | Val | Met | Arg | Pro | Asn | His | Val | Arg | |
| | | | | 245 | | | | | 250 | | | | | 255 | | |
| ggt | aat | gtg | gtg | gtc | act | aac | att | gcc | cag | ctg | gtc | atc | tac | aac | gtc | 816 |
| Gly | Asn | Val | Val | Val | Thr | Asn | Ile | Ala | Gln | Leu | Val | Ile | Tyr | Asn | Val | |
| | | | 260 | | | | | 265 | | | | | 270 | | | |
| cag | ccc | cag | gat | gct | ggc | ata | tac | acc | tgt | aca | gct | cga | aat | gtc | gct | 864 |
| Gln | Pro | Gln | Asp | Ala | Gly | Ile | Tyr | Thr | Cys | Thr | Ala | Arg | Asn | Val | Ala | |
| | 275 | | | | | 280 | | | | | 285 | | | | | |

```
ggt gtc ctg agg gct gac ttc ccg ttg tcg gtg gtc agg ggt ggt cag    912
Gly Val Leu Arg Ala Asp Phe Pro Leu Ser Val Val Arg Gly Gly Gln
290                 295                 300 gcc agg gcc act tca gag agc agt ctc aat ggc aca gct ttt cca gca    960
Ala Arg Ala Thr Ser Glu Ser Ser Leu Asn Gly Thr Ala Phe Pro Ala
305                 310                 315                 320 aca gag tgc ctg aag ccc cca gac agt gag gac tgt gga gag gag cag   1008
Thr Glu Cys Leu Lys Pro Pro Asp Ser Glu Asp Cys Gly Glu Glu Gln
            325                 330                 335 aca cgc tgg cac ttc gac gcc cag gct aac aac tgc ctc act ttc acc   1056
Thr Arg Trp His Phe Asp Ala Gln Ala Asn Asn Cys Leu Thr Phe Thr
        340                 345                 350 ttt ggc cac tgc cac cac aat ctc aac cac ttt gag acc tac gag gcc   1104
Phe Gly His Cys His His Asn Leu Asn His Phe Glu Thr Tyr Glu Ala
            355                 360                 365 tgt atg ctg gct tgt atg agt ggg cca ttg gcc acc tgc agc ctg cct   1152
Cys Met Leu Ala Cys Met Ser Gly Pro Leu Ala Thr Cys Ser Leu Pro
370                 375                 380 gcc ctg caa ggg cct tgc aaa gct tat gtc cca cgc tgg gcc tac aac   1200
Ala Leu Gln Gly Pro Cys Lys Ala Tyr Val Pro Arg Trp Ala Tyr Asn
385                 390                 395                 400 agc cag aca ggc cta tgc cag tcc ttc gtc tat ggc ggc tgt gag ggc   1248
Ser Gln Thr Gly Leu Cys Gln Ser Phe Val Tyr Gly Gly Cys Glu Gly
            405                 410                 415 aac ggt aac aac ttt gaa agc cgt gag gct tgt gag gag tcg tgt ccc   1296
Asn Gly Asn Asn Phe Glu Ser Arg Glu Ala Cys Glu Glu Ser Cys Pro
        420                 425                 430 ttc ccg agg ggt aac cag cac tgc cgg gcc tgc aag ccc cgg caa aaa   1344
Phe Pro Arg Gly Asn Gln His Cys Arg Ala Cys Lys Pro Arg Gln Lys
            435                 440                 445 ctt gtt acc agc ttc tgt cgg agt gac ttt gtc atc ctg ggc agg gtc   1392
Leu Val Thr Ser Phe Cys Arg Ser Asp Phe Val Ile Leu Gly Arg Val
450                 455                 460 tct gag ctg acc gag gag caa gac tcg ggc cgt gcc ctg gtg acc gtg   1440
Ser Glu Leu Thr Glu Glu Gln Asp Ser Gly Arg Ala Leu Val Thr Val
465                 470                 475                 480 gat gag gtc tta aaa gat gag aag atg ggc ctc aag ttt ctg ggc cgg   1488
Asp Glu Val Leu Lys Asp Glu Lys Met Gly Leu Lys Phe Leu Gly Arg
            485                 490                 495 gag cct ctg gaa gtc acc ctg ctt cat gta gac tgg acc tgt cct tgc   1536
Glu Pro Leu Glu Val Thr Leu Leu His Val Asp Trp Thr Cys Pro Cys
            500                 505                 510 ccc aac gtg aca gtg ggt gag aca cca ctc atc atc atg ggg gag gtg   1584
Pro Asn Val Thr Val Gly Glu Thr Pro Leu Ile Ile Met Gly Glu Val
        515                 520                 525 gac ggc ggc atg gcc atg ctg aga ccc gat agc ttt gtg ggg gca tcg   1632
Asp Gly Gly Met Ala Met Leu Arg Pro Asp Ser Phe Val Gly Ala Ser
530                 535                 540 agc aca cgg cgg gtc agg aag ctc cgt gag gtc atg tac aag aaa acc   1680
Ser Thr Arg Arg Val Arg Lys Leu Arg Glu Val Met Tyr Lys Lys Thr
545                 550                 555                 560 tgt gac gtc ctc aag gac ttc ctg ggc ttg caa tga                   1716
Cys Asp Val Leu Lys Asp Phe Leu Gly Leu Gln
            565                 570
```

<210> SEQ ID NO 49
<211> LENGTH: 571
<212> TYPE: PRT
<213> ORGANISM: Mus sp.

```
<400> SEQUENCE: 49

Met Cys Ala Pro Gly Tyr His Arg Phe Trp Phe His Trp Gly Leu Leu
 1               5                  10                  15

Leu Leu Leu Leu Leu Glu Ala Pro Leu Arg Gly Leu Ala Leu Pro Pro
                 20                  25                  30

Ile Arg Tyr Ser His Ala Gly Ile Cys Pro Asn Asp Met Asn Pro Asn
             35                  40                  45

Leu Trp Val Asp Ala Gln Ser Thr Cys Lys Arg Glu Cys Glu Thr Asp
         50                  55                  60

Gln Glu Cys Glu Thr Tyr Glu Lys Cys Pro Asn Val Cys Gly Thr
 65                  70                  75                  80

Lys Ser Cys Val Ala Ala Arg Tyr Met Asp Val Lys Gly Lys Lys Gly
                 85                  90                  95

Pro Val Gly Met Pro Lys Glu Ala Thr Cys Asp His Phe Met Cys Leu
             100                 105                 110

Gln Gln Gly Ser Glu Cys Asp Ile Trp Asp Gly Gln Pro Val Cys Lys
         115                 120                 125

Cys Lys Asp Arg Cys Glu Lys Glu Pro Ser Phe Thr Cys Ala Ser Asp
 130                 135                 140

Gly Leu Thr Tyr Tyr Asn Arg Cys Phe Met Asp Ala Glu Ala Cys Ser
145                 150                 155                 160

Lys Gly Ile Thr Leu Ser Val Val Thr Cys Arg Tyr His Phe Thr Trp
                 165                 170                 175

Pro Asn Thr Ser Pro Pro Pro Glu Thr Thr Val His Pro Thr Thr
             180                 185                 190

Ala Ser Pro Glu Thr Leu Gly Leu Asp Met Ala Ala Pro Ala Leu Leu
         195                 200                 205

Asn His Pro Val His Gln Ser Val Thr Val Gly Glu Thr Val Ser Phe
 210                 215                 220

Leu Cys Asp Val Val Gly Arg Pro Arg Pro Glu Leu Thr Trp Glu Lys
225                 230                 235                 240

Gln Leu Glu Asp Arg Glu Asn Val Val Met Arg Pro Asn His Val Arg
                 245                 250                 255

Gly Asn Val Val Val Thr Asn Ile Ala Gln Leu Val Ile Tyr Asn Val
             260                 265                 270

Gln Pro Gln Asp Ala Gly Ile Tyr Thr Cys Thr Ala Arg Asn Val Ala
         275                 280                 285

Gly Val Leu Arg Ala Asp Phe Pro Leu Ser Val Arg Gly Gly Gln
 290                 295                 300

Ala Arg Ala Thr Ser Glu Ser Ser Leu Asn Gly Thr Ala Phe Pro Ala
305                 310                 315                 320

Thr Glu Cys Leu Lys Pro Pro Asp Ser Glu Asp Cys Gly Glu Glu Gln
                 325                 330                 335

Thr Arg Trp His Phe Asp Ala Gln Ala Asn Asn Cys Leu Thr Phe Thr
             340                 345                 350

Phe Gly His Cys His His Asn Leu Asn His Phe Glu Thr Tyr Glu Ala
         355                 360                 365

Cys Met Leu Ala Cys Met Ser Gly Pro Leu Ala Thr Cys Ser Leu Pro
 370                 375                 380

Ala Leu Gln Gly Pro Cys Lys Ala Tyr Val Pro Arg Trp Ala Tyr Asn
385                 390                 395                 400

Ser Gln Thr Gly Leu Cys Gln Ser Phe Val Tyr Gly Gly Cys Glu Gly
                 405                 410                 415
```

```
Asn Gly Asn Asn Phe Glu Ser Arg Glu Ala Cys Glu Ser Cys Pro
            420                 425                 430
Phe Pro Arg Gly Asn Gln His Cys Arg Ala Cys Lys Pro Arg Gln Lys
            435                 440                 445
Leu Val Thr Ser Phe Cys Arg Ser Asp Phe Val Ile Leu Gly Arg Val
            450                 455                 460
Ser Glu Leu Thr Glu Gln Asp Ser Gly Arg Ala Leu Val Thr Val
465                 470                 475                 480
Asp Glu Val Leu Lys Asp Glu Lys Met Gly Leu Lys Phe Leu Gly Arg
                485                 490                 495
Glu Pro Leu Glu Val Thr Leu Leu His Val Asp Trp Thr Cys Pro Cys
            500                 505                 510
Pro Asn Val Thr Val Gly Glu Thr Pro Leu Ile Ile Met Gly Glu Val
            515                 520                 525
Asp Gly Gly Met Ala Met Leu Arg Pro Asp Ser Phe Val Gly Ala Ser
530                 535                 540
Ser Thr Arg Arg Val Arg Lys Leu Arg Glu Val Met Tyr Lys Lys Thr
545                 550                 555                 560
Cys Asp Val Leu Lys Asp Phe Leu Gly Leu Gln
                565                 570

<210> SEQ ID NO 50
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 50
caccatgtgt gccccagggt atcatcggtt ctgg                              34

<210> SEQ ID NO 51
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 51
ttgcaagccc aggaagtcct tgaggac                                      27

<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence:
      Illustrative N-terminal peptide sequence

<400> SEQUENCE: 52

Leu Pro Pro Ile Arg Tyr Ser His Ala Gly Ile
 1               5                  10

<210> SEQ ID NO 53
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 53
cagacagaca gacagacaga cagacagaca gacagacaga cagacaga                    48
```